United States Patent
Wang

(10) Patent No.: US 10,557,149 B1
(45) Date of Patent: Feb. 11, 2020

(54) RECOMBINANTLY-MODIFIED ADENO-ASSOCIATED VIRUS HELPER VECTORS AND THEIR USE TO IMPROVE THE PACKAGING EFFICIENCY OF RECOMBINANTLY-MODIFIED ADENO-ASSOCIATED VIRUS

(71) Applicant: Vigene Biosciences Inc., Rockville, MD (US)

(72) Inventor: Qizhao Wang, Rockville, MD (US)

(73) Assignee: Vigene Biosciences, Inc., Rockville, MD (US)

( * ) Notice: Subject to any disclaimer, the term of this patent is extended or adjusted under 35 U.S.C. 154(b) by 0 days.

(21) Appl. No.: 16/512,194

(22) Filed: Jul. 15, 2019

(51) Int. Cl.
C12N 15/86 (2006.01)
C12N 5/071 (2010.01)
C12N 5/07 (2010.01)

(52) U.S. Cl.
CPC .......... *C12N 15/86* (2013.01); *C12N 5/0601* (2013.01); *C12N 5/0686* (2013.01)

(58) Field of Classification Search
None
See application file for complete search history.

(56) References Cited

U.S. PATENT DOCUMENTS

| | | |
|---|---|---|
| 6,566,118 B1 | 5/2003 | Atkinson et al. |
| 6,723,551 B2 | 4/2004 | Kotin et al. |
| 6,733,757 B2 | 5/2004 | Patel et al. |
| 6,753,419 B1 | 6/2004 | Toniatti et al. |
| 6,759,050 B1 | 7/2004 | Sista et al. |
| 6,764,845 B2 | 7/2004 | Sista et al. |
| 6,821,511 B2 | 11/2004 | Kotin et al. |
| 6,841,357 B1 | 1/2005 | Vaillancourt et al. |
| 6,846,665 B1 | 1/2005 | Horer et al. |
| 6,962,815 B2 | 11/2005 | Bartlett |
| 6,984,517 B1 | 1/2006 | Chiorini et al. |
| 6,989,264 B2 | 1/2006 | Atkinson et al. |
| 6,995,006 B2 | 2/2006 | Atkinson et al. |
| 7,105,345 B2 | 9/2006 | Wilson et al. |
| 7,115,391 B1 | 10/2006 | Chen et al. |
| 7,122,348 B2 | 10/2006 | Wong et al. |
| 7,186,552 B2 | 3/2007 | Wilson et al. |
| 7,208,315 B2 | 4/2007 | Miller et al. |
| 7,271,002 B2 | 9/2007 | Kotin et al. |
| 7,419,817 B2 | 9/2008 | Chiorini et al. |
| 7,439,065 B2 | 10/2008 | Ferrari et al. |
| 7,479,554 B2 | 1/2009 | Chiorini et al. |
| 7,598,070 B2 | 10/2009 | Sista et al. |
| 7,625,570 B1 | 12/2009 | Schaffer et al. |
| 7,906,111 B2 | 3/2011 | Wilson et al. |
| 8,163,543 B2 | 4/2012 | Urabe et al. |
| 8,192,975 B2 | 6/2012 | Sista et al. |
| 8,507,267 B2 | 8/2013 | Chiorini et al. |
| 8,697,359 B1 | 4/2014 | Zhang |
| 8,846,389 B2 | 9/2014 | Chiorini et al. |
| 8,852,607 B2 | 10/2014 | Sista et al. |
| 8,945,918 B2 | 2/2015 | Chen |
| 9,193,956 B2 | 11/2015 | Schaffer et al. |
| 9,441,206 B2 | 9/2016 | Grieger et al. |
| 9,441,244 B2 | 9/2016 | Schaffer et al. |
| 9,457,103 B2 | 10/2016 | Schaffer et al. |
| 9,458,517 B2 | 10/2016 | Schaffer et al. |
| 9,598,703 B2 | 3/2017 | Garcia et al. |
| 9,677,089 B2 | 6/2017 | Gao et al. |
| 9,737,618 B2 | 8/2017 | Wilson et al. |
| 9,856,539 B2 | 1/2018 | Schaffer et al. |
| 9,879,279 B2 | 1/2018 | Chen |
| 9,879,282 B2 | 1/2018 | Chen |
| 9,884,071 B2 | 2/2018 | Wilson et al. |
| 10,000,772 B2 | 6/2018 | Doudna et al. |
| 10,017,746 B2 | 7/2018 | Sheldon et al. |
| 10,046,016 B2 | 8/2018 | Schaffer et al. |
| 10,113,167 B2 | 10/2018 | Doudna et al. |
| 10,161,011 B2 | 12/2018 | Akashika et al. |
| 10,202,657 B2 | 2/2019 | Schaffer et al. |
| 10,214,566 B2 | 2/2019 | Schaffer et al. |
| 10,214,730 B2 | 2/2019 | Bahou et al. |

(Continued)

FOREIGN PATENT DOCUMENTS

WO WO 2017/112948 6/2017

OTHER PUBLICATIONS

Adamson-Small, L. et al. (2017) "*Sodium Chloride Enhances Recombinant Adeno-Associated Virus Production in a Serum-Free Suspension Manufacturing Platform Using the Herpes Simplex Virus System*," Hum. Gene Ther. Meth. 28(1):1-14.

Auricchio, A. et al. (2001) "*Isolation of Highly Infectious and Pure Adeno-Associated Virus Type 2 Vectors With a Single-Step Gravity-Flow Column*," Hum. Gene Ther. 12:71-76.

Ayuso, E. (2016) "*Manufacturing of Recombinant Adeno-Associated Viral Vectors: New Technologies Are Welcome*," Methods & Clinical Development 3: 15049 (pp. 1-3).

(Continued)

*Primary Examiner* — Stacy B Chen
(74) *Attorney, Agent, or Firm* — AuerbachSchrot LLC; Jeffrey I. Auerbach

(57) ABSTRACT

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

16 Claims, 16 Drawing Sheets
Specification includes a Sequence Listing.

(56) References Cited

U.S. PATENT DOCUMENTS

| | | | |
|---|---|---|---|
| 10,214,785 | B2 | 2/2019 | Schaffer et al. |
| 10,227,611 | B2 | 3/2019 | Doudna et al. |
| 10,265,417 | B2 | 4/2019 | Wilson et al. |
| 10,266,846 | B2 | 4/2019 | Gao et al. |
| 10,294,452 | B2 | 5/2019 | He |
| 10,301,650 | B2 | 5/2019 | Gao et al. |
| 2005/0266567 | A1 | 12/2005 | Atkinson et al. |

OTHER PUBLICATIONS

Balakrishnan, B. et al. (2014) "*Basic Biology of Adeno-Associated Virus (AAV) Vectors Used in Gene Therapy,*" Curr. Gene Ther. 14(2):86-100.
Ben-Israel, H. et al. (2002) "*Adenovirus and Cell Cycle Control,*" Front. Biosci. 7:d1369-d1395.
Berns, K. I. et al. (2017) "*AAV: An Overview of Unanswered Questions,*" Human Gene Ther. 28(4):308-313.
Berry, G.E. et al. (2016) "*Cellular Transduction Mechanisms of Adeno-Associated Viral Vectors,*" Curr. Opin. Virol. 21:54-60.
Blessing, D. et al. (2016) "*Adeno Associated Virus and Lentivirus Vectors: A Refined Toolkit for the Central Nervous System,*" 21:61-66.
Brument, N. et al. (2002) "*A Versatile and Scalable Two-Step Ion-Exchange Chromatography Process for the Purification of Recombinant Adeno-Associated Virus Serotypes-2 and -5,*" Mol. Ther. 6:678-686.
Büning, H. et al. (2019) "*Capsid Modifications for Targeting and Improving the Efficacy of AAV Vectors,*" Mol. Ther. Meth. Clin. Devel. 12:p. 248-p. 265.
Cao, M. et al. (2014) "*The X Gene of Adeno-Associated Virus 2 (AAV2) Is Involved in Viral DNA Replication,*" PLoS One 9, e104596:1-10.
Chiorini, J.A. et al. (1997) "*Cloning of Adeno-Associated Virus Type 4 (AAV4) and Generation of Recombinant AAV4 Particles,*" J. Virol. 71(9):6823-6833.
Chopra, A. (2007) "*Recombinant Adenovirus With Enhanced Green Fluorescent Protein,*" In: Molecular Imaging and Contrast Agent Database (MICAD) [Internet]. Bethesda (MD): National Center for Biotechnology Information (pp. 1-5).
Cinelli, R.A. et al. (2000) "*The Enhanced Green Fluorescent Protein As a Tool for the Analysis of Protein Dynamics and Localization: Local Fluorescence Study At the Single Molecule Level,*" Photochem. Photobiol. 71(6):771-776.
Clément, N. et al. (2016) "*Manufacturing of Recombinant Adeno-Associated Viral Vectors for Clinical Trials,*" Meth. Clin. Develop. 3:16002:1-7.
Colella, P. et al. (2018) "*Emerging Issues in AAV-Mediated in Vivo Gene Therapy,*" Molec. Ther. Meth. Clin. Develop. 8:87-104.
Davidoff, A.M. et al. (2004) "*Purification of Recombinant Adeno-Associated Virus Type 8 Vectors by Ion Exchange Chromatography Generates Clinical Grade Vector Stock,*" J. Virol. Methods 121:209-215.
Duan, D. (2016) "*Systemic Delivery of Adeno-Associated Viral Vectors,*" Curr. Opin. Virol. 21:16-25.
During, M.J. et al. (1998) "*In Vivo Expression of Therapeutic Human Genes for Dopamine Production in the Caudates of MPTP-Treated Monkeys Using an AAV Vector,*" Gene The. 5:820-827.
Durocher, Y. et al. (2007) "*Scalable Serum-Free Production of Recombinant Adeno-Associated Virus Type 2 by Transfection of 293 Suspension Cells,*" J. Virol. Meth. 144:32-40.
Eddy, J. et al. (2006) "*Gene Function Correlates With Potential for G4 DNA Formation in the Human Genome,*" Nucleic Acids Res. 34:3887-3896.
Egelie, K.J. et al. (2016) "*The Emerging Patent Landscape of CRISPR—Cas Gene Editing Technology,*" Nature Biotechnol. 34(10):1025-1031.
Ferreira, V. et al. (2014) "*Immune Responses to AAV-Vectors, The Glybera Example From Bench to Bedside*" Front. Immunol. 5(82):1-15.

François, A. et al. (2018) "*Accurate Titration of Infectious AAV Particles Requires Measurement of Biologically Active Vector Genomes and Suitable Controls,*" Molec. Ther. Meth. Clin. Develop. 10:223-236.
Gambotto, A. et al. (2000) "*Immunogenicity of Enhanced Green Fluorescent Protein (EGFP) in BALB/C Mice: Identification of an H2-Kd-Resfricted CTL Epitope,*" Gene Ther. 7(23):2036-2040.
Gao, G.P. et al. (2002) "*Novel Adeno Associated Viruses From Rhesus Monkeys As Vectors for Human Gene Therapy,*" Proc. Natl. Acad. Sci. (U.S.A.) 99(18):11854-11859.
Ghosh, A. et al. (2007) "*Expanding Adeno-Associated Viral Vector Capacity: A Tale of Two Vectors,*" Biotechnol. Genet. Eng. Rev. 24:165-177.
Grieger, J.C. et al. (2012) "*Adeno-Associated Virus Vectorology, Manufacturing, and Clinical Applications,*" Meth. Enzymol. 507:229-254.
Grimm, D. et al. (1998) "*Novel Tools for Production and Purification of Recombinant Adeno-Associated Virus Vectors,*" Hum. Gene Ther. 9:2745-2760.
Guggino, W.B. et al. (2017) "*AAV Gene Therapy for Cystic Fibrosis: Current Barriers and Recent Developments,*" Expert Opin Biol Ther. 17(10): 1265-1273.
Hastie, E. et al. (2015) "*Adeno Associated Virus at 50: A Golden Anniversary of Discovery, Research, and Gene Therapy Success—A Personal Perspective,*" Human Gene Ther. 26:257-265.
Hauck, B. et al. (2003) "*Generation and Characterization of Chimeric Recombinant AAV Vectors,*" Mol. Ther. 7:419-425.
Hocquemiller, M. et al. (2016) "*Adeno-Associated Virus-Based Gene Therapy for CNS Diseases,*" Hum. Gene Ther. 27(7):478-496.
Hoeben, R.C. et al. (2013) "*Adenovirus DNA Replication,*" Cold Spring Harb. Perspect. Biol. 5:a013003 (pp. 1-11).
Johnson, F.B. et al. (1972) "*Immunological Reactivity of Antisera Prepared Against the Sodium Dodecyl Sulfate-Treated Structural Polypeptides of Adenovirus-Associated Virus,*" J. Virol. 9(6):1017-1026.
Kay, M. et al. (2017) "*Future of rAAV Gene Therapy: Platform for RNAi, Gene Editing and Beyond,*" Human Gene Ther. 28:361-372.
Kotterman, M.A. et al. (2014) "*Engineering Adeno-Associated Viruses for Clinical Gene Therapy,*" Nat. Rev. Genet. 15(7):445-451.
Kwon, I. et al. (2007) "*Designer Gene Delivery Vectors: Molecular Engineering and Evolution of Adeno-Associated Viral Vectors for Enhanced Gene Transfer,*" Pharm. Res. 25(3):489-499.
Lackner, D.F. et al. (2002) "*Studies of the Mechanism of Transactivation of the Adeno-Associated Virus p19 Promoter by Rep Protein,*" J. Virol. 76(16):8225-8235.
Le, H.T. et al. (2005) "Utility of Pegylated Recombinant Adeno-Associated Viruses for Gene Transfer," J. Control. Release 108:161-177.
Lee, G.K. et al. (2005) "*PEG Conjugation Moderately Protects Adeno-Associated Viral Vectors Against Antibody Neutralization,*" Biotechnol. Bioeng. 92:24-34.
Lino, C.A. et al. (2018) "*Delivering CRISPR: A Review of the Challenges and Approaches,*" Drug Deliv. 25(1):1234-1237.
Lisowski, L. et al. (2015) "*Adeno-Associated Virus Serotypes for Gene Therapeutics,*" 24:59-67.
Liu, Q. et al. (2014) "*Neutralizing Antibodies Against AAV2, AAV5 and AAV8 in Healthy and HIV-1-Infected Subjects in China: Implications for Gene Therapy Using AAV Vectors,*" Gene Ther. 21:732-738.
Lock, M. et al. (2010) "*Rapid, Simple, and Versatile Manufacturing of Recombinant Adeno-Associated Viral Vectors at Scale,*" Hum. Gene Ther. 21:1259-1271.
Lykken, E.A. et al. (2018) "*Recent Progress and Considerations for AAV Gene Therapies Targeting the Central Nervous System,*" J. Neurodevelop. Dis. 10:16:1-10.
Matsushita, T. et al. (1998) "*Adeno-Associated Virus Vectors Can Be Efficiently Produced Without Helper Virus,*" Gene Ther. 5:938-945.
McClements, M.E. et a. (2017) "*Adeno-associated Virus (AAV) Dual Vector Strategies for Gene Therapy Encoding Large Transgenes,*" Yale J. Biol. Med. 90:611-623.
Monahan, P.E. et al. (2000) "*AAV Vectors: Is Clinical Success on the Horizon?,*" Gene Ther. 7:24-30.

(56) References Cited

OTHER PUBLICATIONS

Murphy, M. et al. (2007) "*Adeno-Associated Virus Type 2 p5 Promoter: a Rep-Regulated DNA Switch Element Functioning in Transcription, Replication, and Site-Specific Integration*," J. Virol. 81(8):3721-3730.

Nash, K. et al. (2009) "*Identification of Cellular Proteins That Interact With the Adeno-Associated Virus Rep Protein*," J. Virol. 83(1):454-469.

Naso, M.F. et al. (2017) "*Adeno-Associated Virus (AAV) as a Vector for Gene Therapy*," BioDrugs 31:317-334.

Ni, T.H. et al.(1998) "*Cellular Proteins Required for Adeno-Associated Virus DNA Replication in the Absence of Adenovirus Coinfection*," J. Virol. 72(4):2777-2787.

Nicolas, A. et al. (2012) "*Factors Influencing Helper-Independent Adeno-Associated Virus Replication*," Virology 432(1):1-9.

Ogasawara, Y. et al. (1998) "*The Use of Heterologous Promoters for Adeno-Associated Virus (AAV) Protein Expression in AAV Vector Production*," Microbiol. Immunol. 42(3):177-185.

Penaud-Budloo, M. et al. (2018) "*Pharmacology of Recombinant Adeno-associated Virus Production*," Molec. Ther. Meth. Clin. Develop. 8:166-180.

Rabinowitz, J.E. et al. (2004) "*Crossdressing the Virion: The Transcapsidation of Adeno-Associated Virus Serotypes Functionally Defines Subgroups*," J. Virol. 78:4421-4432.

Rastall, D.P.W. (2017) "*Current and Future Treatments for Lysosomal Storage Disorders*," Curr. Treat Options Neurol. 19(12):45.

Salganik, M. et al. (2015) "*Adeno-Associated Virus As a Mammalian DNA Vector*," Microbiol. Spectr. 3(4):1-32.

Santiago-Ortiz, J.L. (2016) "*Adeno Associated Virus (AAV) Vectors in Cancer Gene Therapy*," J. Control Release 240:287-301.

Satkunanathan, S. et al. (2017) "*The Function of DNA Binding Protein Nucleophosmin in AAV Replication*," Virol. 510:46-54.

Sharma, A. et al. (2010) "*Transduction Efficiency of AAV 2/6, 2/8 and 2/9 Vectors for Delivering Genes in Human Corneal Fibroblasts*," Brain Res. Bull. 81(2-3):273-278.

Smith, J.K. et al. (2018) "*Creating an Arsenal of Adeno-Associated Virus (AAV) Gene Delivery Stealth Vehicles*," PLoS Pathog. 14(5):1-6.

Smith, R.H. et al. (2009) "*A Simplified Baculovirus-AAV Expression Vector System Coupled With One-Step Affinity Purification Yields High-Titer rAAV Stocks From Insect Cells*," Mol. Ther. 17:1888-1896.

Tsien, R.Y. (1998) "*The Green Fluorescent Protein*," Annu. Rev. Biochem. 67:509-544.

Van Vliet K.M. et al. (2008) *The Role of the Adeno-Associated Virus Capsid in Gene Transfer*. In: Drug Delivery Systems, Jain, K.K. (eds.), Meth. Molec. Biol. 437:51-91.

Vandamme, C. et al. (2017) "*Unraveling the Complex Story of Immune Responses to AAV Vectors Trial After Trial*," Hum. Gene. Ther. 28(11):1061-1074.

Weitzman, M.D. (2005) "*Functions of the Adenovirus E4 Proteins and Their Impact on Viral Vectors*," Front. Biosci. 10:1106-1117.

Weitzman, M.D. (2006) "*The Parvovirus Life Cycle: An Introduction to Molecular Interactions Important for Infection*," In: Kerr, J.R. et al. (Eds.) Parvoviruses, Hodder Arnold, London, UK (pp. 143-156).

Wu, Z. et al. (2010) "*Effect of Genome Size on AAV Vector Packaging*," Molec. Ther. 18:80-86.

Yao, T et al. (2017) "*Animal-Cell Culture Media: History, Characteristics, and Current Issues*," Reproduc. Med. Biol. 16(2): 99-117.

Zen, Z. et al. (2004) "*Infectious Titer Assay for Adeno-Associated Virus Vectors With Sensitivity Sufficient to Detect Single Infectious Events*," Hum. Gene Ther. 15:709-715.

Zinn, E. et al. (2014) "*Adeno-Associated Virus: Fit to Serve*," Curr. Opin. Virol. 0:90-97.

Zolotukhin, S. et al. (1999) "*Recombinant Adeno-Associated Virus Purification Using Novel Methods Improves Infectious Titer and Yield*," Gene Ther. 6:973-985.

Zolotukhin, S. et al. (2002) "*Production and Purification of Serotype 1, 2, and 5 Recombinant Adeno-Associated Viral Vectors*," Methods 28:158-167.

RECOMBINANTLY-MODIFIED ADENO-ASSOCIATED VIRUS HELPER VECTORS AND THEIR USE TO IMPROVE THE PACKAGING EFFICIENCY OF RECOMBINANTLY-MODIFIED ADENO-ASSOCIATED VIRUS

FIELD OF THE INVENTION

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

REFERENCE TO SEQUENCE LISTING

This application includes one or more Sequence Listings pursuant to 37 C.F.R. 1.821 et seq., which are disclosed in computer-readable media (file name: 2650-0004US_ST25.txt, created on Jul. 15, 2019, and having a size of 84,101 bytes), which file is herein incorporated by reference in its entirety.

BACKGROUND OF THE INVENTION

I. Adeno-Associated Virus (AAV)

Adeno-Associated Virus (AAV) is a small, naturally-occurring, non-pathogenic virus belonging to the *Dependovirus* genus of the Parvoviridae (Balakrishnan, B. et al. (2014) "*Basic Biology of Adeno Associated Virus (AAV) Vectors Used in Gene Therapy*," Curr. Gene Ther. 14(2):86-100; Zinn, E. et al. (2014) "*Adeno-Associated Virus: Fit To Serve*," Curr. Opin. Virol. 0:90-97). Despite not causing disease, AAV is known to be able to infect humans and other primates and is prevalent in human populations (Johnson, F. B. et al. (1972) "*Immunological Reactivity of Antisera Prepared Against the Sodium Dodecyl Sulfate-Treated Structural Polypeptides of Adenovirus-Associated Virus*," J. Virol. 9(6):1017-1026). AAV infect a broad range of different cell types (e.g., cells of the central nervous system, heart, kidney, liver, lung, pancreas, retinal pigment epithelium or photoreceptor cells, or skeletal muscle cells). Twelve serotypes of the virus (e.g., AAV2, AAV5, AAV6, etc.), exhibiting different tissue infection capabilities ("tropisms"), have been identified (Colella, P. et al. (2018) "*Emerging Issues in AAV-Mediated In Vivo Gene Therapy*," Molec. Ther. Meth. Clin. Develop. 8:87-104; Hocquemiller, M. et al. (2016) "*Adeno-Associated Virus-Based Gene Therapy for CNS Diseases*," Hum. Gene Ther. 27(7):478-496; Lisowski, L. et al. (2015) "*Adeno-Associated Virus Serotypes For Gene Therapeutics,*" 24:59-67).

AAV is a single-stranded DNA virus that is composed of approximately 4,800 nucleotides. The viral genome may be described as having a 5' half and a 3' half which together comprise the genes that encode the virus' proteins (FIG. 1). The 5' half of the AAV genome comprises the AAV rep gene, which, through the use of multiple reading frames, staggered initiating promoters (P5, P19 and P40) and alternate splicing, encodes four non-structural Rep proteins (Rep40, Rep52, Rep68 and Rep78) that are required for viral transcription control and replication and for the packaging of viral genomes into the viral capsule (Lackner, D. F. et al. (2002) "*Studies of the Mechanism of Transactivation of the Adeno-Associated Virus p19 Promoter by Rep Protein*," J. Virol. 76(16):8225-8235). In the presence of viral proteins (such as Ad proteins), the P5 promoter becomes activated and mediates the transcription of the Rep68 and Rep78 proteins, which are involved in transcriptional control, in latency, in rescue, and in viral DNA replication and thus function as master controllers of the AAV life cycle (Murphy, M. et al. (2007) "*Adeno-Associated Virus Type 2 p5 Promoter: a Rep-Regulated DNA Switch Element Functioning in Transcription, Replication, and Site-Specific Integration*," J. Virol. 81(8):3721-3730). Expression of the Rep68 and Rep78 proteins activates the P19 promoter, which is responsible for the transcription of the Rep40 and Rep52 proteins (Lackner, D. F. et al. (2002) "*Studies of the Mechanism of Transactivation of the Adeno-Associated Virus p19 Promoter by Rep Protein*," J. Virol. 76(16):8225-8235; Ogasawara, Y. et al. (1998) "*The Use of Heterologous Promoters for Adeno Associated Virus (AAV) Protein Expression in AAV Vector Production*," Microbiol. Immunol. 42(3):177-185). The 3' half the AAV genome comprises the AAV capsid gene (cap), which encodes three capsid proteins (VP): VP1, VP2 and VP3. The three capsid proteins are translated from a single mRNA transcript that is controlled by a single promoter (P40 in case of AAV2). The 3' half of the AAV genome also comprises the AAP gene, which encodes the AAV assembly-activating protein (AAP). Sixty VP monomers (comprising approximately 5 copies of VP1, 5 copies of VP2, and 50 copies of VP3) self-assemble around the AAV genome to form the icosahedral protein shell (capsid) of the mature viral particle (Büning, H. et al. (2019) "*Capsid Modifications for Targeting and Improving the Efficacy of AAV Vectors*," Mol. Ther. Meth. Clin. Devel. 12:P248-P265; Van Vliet K. M. et al. (2008) *The Role of the Adeno-Associated Virus Capsid in Gene Transfer*. In: DRUG DELIVERY SYSTEMS, Jain, K. K. (eds.), Meth. Molec. Biol. 437:51-91). The AAV AAP protein is believed to be required for stabilizing and transporting newly produced VP proteins from the cytoplasm into the cell nucleus. The 3' half of the AAV genome also comprises the AAV X gene, which is believed to encode a protein that supports genome replication (Colella, P. et al. (2018) "*Emerging Issues in AAV-Mediated In Vivo Gene Therapy*," Molec. Ther. Meth. Clin. Develop. 8:87-104; Büning, H. et al. (2019) "*Capsid Modifications for Targeting and Improving the Efficacy of AAV Vectors*," Mol. Ther. Meth. Clin. Devel. 12:P248-P265; Cao, M. et al. (2014) "*The X Gene Of Adeno-Associated Virus 2 (AAV2) Is Involved In Viral DNA Replication*," PLoS ONE 9, e104596:1-10).

The above-described AAV gene-coding sequences are flanked by two AAV-specific palindromic inverted terminal repeated sequences (ITR) of 145 nucleotides (Balakrishnan, B. et al. (2014) "*Basic Biology of Adeno-Associated Virus (AAV) Vectors Used in Gene Therapy*," Curr. Gene Ther. 14(2):86-100; Colella, P. et al. (2018) "*Emerging Issues in AAV-Mediated In Vivo Gene Therapy*," Molec. Ther. Meth. Clin. Develop. 8:87-104).

AAV is an inherently defective virus, lacking the capacity to perform at least two critical functions: the ability to initiate the synthesis of viral-specific products and the ability to assemble such products to form the icosahedral protein shell (capsid) of the mature infectious viral particle. It thus requires a co-infecting "helper" virus, such as adenovirus (Ad), herpes simplex virus (HSV), cytomegalovirus (CMV), vaccinia virus or human papillomavirus to provide the viral-associated (VA) RNA that is not encoded by the genes of the AAV genome. Such VA RNA is not translated, but plays a role in regulating the translation of other viral genes. Similarly, the AAV genome does not include genes that encode the viral proteins E1a, E1b, E2a, and E4; thus, these proteins must also be provided by a co-infecting "helper" virus. The E1a protein greatly stimulate viral gene transcription during the productive infection. The E1b protein block apoptosis in adenovirus-infected cells, and thus allow productive infection to proceed. The E2a protein plays a role in the elongation phase of viral strand displacement replication by unwinding the template and enhancing the initiation of transcription. The E4 protein has been shown to affect transgene persistence, vector toxicity and immunogenicity (see, Grieger, J. C. et al. (2012) "*Adeno-Associated Virus Vectorology, Manufacturing, and Clinical Applications*," Meth. Enzymol. 507:229-254; Dyson, N. et al. (1992) "*Adenovirus E1A Targets Key Regulators Of Cell Proliferation*," Canc. Surv. 12:161-195; Jones N. C. (1990) "*Transformation By The Human Adenoviruses*," Semin. Cancer Biol. 1(6):425-435; Ben-Israel, H. et al. (2002) "*Adenovirus and Cell Cycle Control*," Front. Biosci. 7:d1369-d1395; Hoeben, R. C. et al. (2013) "*Adenovirus DNA Replication*," Cold Spring Harb. Perspect. Biol. 5:a013003 (pages 1-11); Berk, A. J. (2013) "*Adenoviridae: The Viruses And Their Replication*, In: FIELDS VIROLOGY, 6*th* Edition (Knipe, D. M. et al., Eds.), Vol. 2., Lippincott Williams & Wilkins, Philadelphia, pages 1704-1731; Weitzman, M. D. (2005) "*Functions Of The Adenovirus E4 Proteins And Their Impact On Viral Vectors*," Front. Biosci. 10:1106-1117).

AAV viruses infect both dividing and non-dividing cells, and persist as circular episomal molecules or can be integrated into the DNA of a host cell at specific chromosomic loci (Adeno-Associated Virus Integration Sites or AAV5) (Duan, D. (2016) "*Systemic Delivery Of Adeno-Associated Viral Vectors*," Curr. Opin. Virol. 21:16-25; Grieger, J. C. et al. (2012) "*Adeno-Associated Virus Vectorology, Manufacturing, and Clinical Applications*," Meth. Enzymol. 507: 229-254). AAV remains latent in such infected cells unless a helper virus is present to provide the functions needed for AAV replication and maturation.

II. rAAV and their Use in Gene Therapy

In light of AAV's properties, recombinantly-modified versions of AAV (rAAV) have found substantial utility as vectors for gene therapy (see, Naso, M. F. et al. (2017) "*Adeno-Associated Virus (AAV) as a Vector for Gene Therapy*," BioDrugs 31:317-334; Berns, K. I. et al. (2017) "*AAV: An Overview of Unanswered Questions*," Human Gene Ther. 28(4):308-313; Berry, G. E. et al. (2016) "*Cellular Transduction Mechanisms Of Adeno-Associated Viral Vectors*," Curr. Opin. Virol. 21:54-60; Blessing, D. et al. (2016) "*Adeno-Associated Virus And Lentivirus Vectors: A Refined Toolkit For The Central Nervous System,*" 21:61-66; Santiago-Ortiz, J. L. (2016) "*Adeno-Associated Virus (AAV) Vectors in Cancer Gene Therapy*," J. Control Release 240: 287-301; Salganik, M. et al. (2015) "*Adeno-Associated Virus As A Mammalian DNA Vector*," Microbiol. Spectr. 3(4):1-32; Hocquemiller, M. et al. (2016) "*Adeno-Associated Virus-Based Gene Therapy for CNS Diseases*," Hum. Gene Ther. 27(7):478-496; Lykken, E. A. et al. (2018) "*Recent Progress And Considerations For AAV Gene Therapies Targeting The Central Nervous System*," J. Neurodevelop. Dis. 10:16:1-10; Büning, H. et al. (2019) "*Capsid Modifications for Targeting and Improving the Efficacy of AAV Vectors*," Mol. Ther. Meth. Clin. Devel. 12:P248-P265; During, M. J. et al. (1998) "*In Vivo Expression Of Therapeutic Human Genes For Dopamine Production In The Caudates Of MPTP-Treated Monkeys Using An AAV Vector*," Gene The. 5:820-827; Grieger, J. C. et al. (2012) "*Adeno-Associated Virus Vectorology, Manufacturing, and Clinical Applications*," Meth. Enzymol. 507:229-254; Kotterman, M. A. et al. (2014) "*Engineering Adeno-Associated Viruses For Clinical Gene Therapy*," Nat. Rev. Genet. 15(7):445-451; Kwon, I. et al. (2007) "*Designer Gene Delivery Vectors: Molecular Engineering and Evolution of Adeno-Associated Viral Vectors for Enhanced Gene Transfer*," Pharm. Res. 25(3):489-499; U.S. Pat. Nos. 10,266,845; 10,081,659; 9,890,396; 9,840,719; 9,839,696; 9,834,789; 9,803,218; 9,783,825; 9,777,291; 9,540,659; 9,527,904; 8,236,557; 7,972,593 and 7,943,374).

rAAV are typically produced using circular plasmids ("rAAV plasmid vector"). The AAV rep and cap genes are typically deleted from such constructs and replaced with a promoter, a β-globin intron, a cloning site into which a therapeutic gene of choice (transgene) has been inserted, and a poly-adenylation ("polyA") site. The inverted terminal repeated sequences (ITR) of the rAAV are, however, retained, so that the transgene expression cassette of the rAAV plasmid vector is flanked by AAV ITR sequences (Colella, P. et al. (2018) "*Emerging Issues in AAV-Mediated In Vivo Gene Therapy*," Molec. Ther. Meth. Clin. Develop. 8:87-104; Büning, H. et al. (2019) "*Capsid Modifications for Targeting and Improving the Efficacy of AAV Vectors*," Mol. Ther. Meth. Clin. Devel. 12:P248-P265). Thus, in the 5' to 3' direction, the rAAV comprises a 5' ITR, the transgene expression cassette of the rAAV, and a 3' ITR.

rAAV have been used to deliver a transgene to patients suffering from any of a multitude of genetic diseases (e.g., hereditary lipoprotein lipase deficiency (LPLD), Leber's congenital amaurosis (LCA), aromatic L-amino acid decarboxylase deficiency (AADC), choroideremia and hemophilia), and have utility in new clinical modalities, such as in interfering RNA (RNAi) therapy and gene-modifying strategies such as Crispr/Cas9 (U.S. Pat. Nos. 8,697,359, 10,000,772, 10,113,167, 10,227,611; Lino, C. A. et al. (2018) "*Delivering CRISPR: A Review Of The Challenges And Approaches*," Drug Deliv. 25(1):1234-1237; Ferreira, V. et al. (2014) "*Immune Responses To AAV-Vectors, The Glybera Example From Bench To Bedside*" Front. Immunol. 5(82):1-15), Büning, H. et al. (2019) "*Capsid Modifications for Targeting and Improving the Efficacy of AAV Vectors*," Mol. Ther. Meth. Clin. Devel. 12:P248-P265; Rastall, D. P. W. (2017) "*Current and Future Treatments for Lysosomal Storage Disorders*," Curr. Treat Options Neurol. 19(12):45; Kay, M. et al. (2017) "*Future Of rAAV Gene Therapy: Platform For RNAi, Gene Editing And Beyond*," Human Gene Ther. 28:361-372); Berns, K. I. et al. (2017) "*AAV: An Overview of Unanswered Questions*," Human Gene Ther. 28(4):308-313). More than 150 clinical trials involving rAAV have been instituted (Büning, H. et al. (2019) "*Capsid Modifications for Targeting and Improving the Efficacy of AAV Vectors*," Mol. Ther. Meth. Clin. Devel. 12:P248-P265; Clément, N. et al. (2016) "*Manufacturing Of Recombinant Adeno Associated Viral Vectors For Clinical Trials*," Meth. Clin. Develop. 3:16002:1-7). The most commonly used AAV serotype for such recombinantly-modified AAV is AAV2, which is capable of infecting cells of the central nervous system, kidney, retinal pigment epithelium and photoreceptor cells. AAV serotype is AAV9, which infects muscle cells, also has been widely used (Duan, D. (2016)

"Systemic Delivery Of Adeno-Associated Viral Vectors," Curr. Opin. Virol. 21:16-25). AAV serotypes are described in U.S. Pat. Nos. 10,301,650; 10,266,846; 10,265,417; 10,214,785; 10,214,566; 10,202,657; 10,046,016; 9,884,071; 9,856,539; 9,737,618; 9,677,089; 9,458,517; 9,457,103; 9,441,244; 9,193,956; 8,846,389; 8,507,267; 7,906,111; 7,479,554; 7,186,552; 7,105,345; 6,984,517; 6,962,815; and 6,733,757.

III. Methods of rAAV Production rAAV containing a desired transgene expression cassette are typically produced by human cells (such as HEK293) grown in suspension. Since, as described above, rAAV are defective viruses, additional functions must be provided in order to replicate and package rAAV.

rAAV can be produced by transiently transfecting cells with an rAAV plasmid vector and a second plasmid vector that comprises an AAV helper function-providing polynucleotide that provides the Rep52 and Rep78 genes that are required for vector transcription control and replication, and for the packaging of viral genomes into the viral capsule (Rep40 and Rep68 are not required for rAAV production) and the cap genes that were excised from the AAV in order to produce the rAAV. The second plasmid vector may additionally comprise a non-AAV helper function-providing polynucleotide that encodes the viral transcription and translation factors (E1a, E1b, E2a, VA and E4) required for AAV proliferation, so as to comprise, in concert with the rAAV, a double plasmid transfection system (Grimm, D. et al. (1998) "Novel Tools For Production And Purification Of Recombinant Adeno-Associated Virus Vectors," Hum. Gene Ther. 9:2745-2760; Penaud-Budloo, M. et al. (2018) "Pharmacology of Recombinant Adeno-associated Virus Production," Molec. Ther. Meth. Clin. Develop. 8:166-180).

However, it has become increasingly common to clone the AAV helper function-providing polynucleotide (which provides the required rep and cap genes) into an AAV helper plasmid, and to clone the non-AAV helper function-providing polynucleotide (which provides the genes that encode the viral transcription and translation factors) on a different plasmid (e.g., an "Ad helper plasmid"), so that such plasmids, in concert with an rAAV plasmid vector, comprise a triple plasmid transfection system (FIG. 2). Use of the triple plasmid transfection system has the advantage of permitting one to easily switch one cap gene for another, thereby facilitating changes in the rAAV's serotype. The use of helper plasmids, rather than helper viruses, permits rAAV to be produced without additionally producing particles of the helper virus (François, A. et al. (2018) "Accurate Titration of Infectious AAV Particles Requires Measurement of Biologically Active Vector Genomes and Suitable Controls," Molec. Ther. Meth. Clin. Develop. 10:223-236; Matsushita, T. et al. (1998) "Adeno-Associated Virus Vectors Can Be Efficiently Produced Without Helper Virus," Gene Ther. 5:938-945).

The transient transfection of plasmid DNAs comprising the rAAV plasmid vector, the AAV rep and cap genes, and the trans-acting AAD helper genes into HEK293 cells by calcium phosphate coprecipitation has become the standard method to produce rAAV in the research laboratory (Grimm, D. et al. (1998) "Novel Tools For Production And Purification Of Recombinant Adeno-Associated Virus Vectors," Hum. Gene Ther. 9:2745-2760). However, the use of such a calcium phosphate-mediated transfection process with suspension-cultured transfected mammalian cells requires media exchanges, and is thus not considered ideal for the large-scale rAAV production that is required in order to produce therapeutic doses of rAAV (Lock, M. et al. (2010) "Rapid, Simple, and Versatile Manufacturing of Recombinant Adeno-Associated Viral Vectors at Scale," Hum. Gene Ther. 21:1259-1271). For this reason, polyethylenimine (PEI), has been used as a transfection reagent and has been found to provide yields of virus that are similar to those obtained using calcium phosphate-mediated transfection (Durocher, Y. et al. (2007) "Scalable Serum-Free Production Of Recombinant Adeno-Associated Virus Type 2 By Transfection Of 293 Suspension Cells," J. Virol. Meth. 144:32-40).

rAAV may alternatively be produced in insect cells (e.g., sf9 cells) using baculoviral vectors (see, e.g., U.S. Pat. Nos. 9,879,282; 9,879,279; 8,945,918; 8,163,543; 7,271,002 and 6,723,551), or in HSV-infected baby hamster kidney (BHK) cells (e.g., BHK21) (François, A. et al. (2018) "Accurate Titration of Infectious AAV Particles Requires Measurement of Biologically Active Vector Genomes and Suitable Controls," Molec. Ther. Meth. Clin. Develop. 10:223-236). Methods of rAAV production are reviewed in Grieger, J. C. et al. (2012) "Adeno-Associated Virus Vectorology, Manufacturing, and Clinical Applications," Meth. Enzymol. 507:229-254, and in Penaud-Budloo, M. et al. (2018) "Pharmacology of Recombinant Adeno-associated Virus Production," Molec. Ther. Meth. Clin. Develop. 8:166-180.

IV. Methods of rAAV Purification and Recovery

After production, rAAV are typically collected and purified by one or more overnight CsCl gradient centrifugations (Zolotukhin, S. et al. (1999) "Recombinant Adeno Associated Virus Purification Using Novel Methods Improves Infectious Titer And Yield," Gene Ther. 6:973-985), followed by desalting to form a purified rAAV production stock. Titers of $10^{12}$-$10^{13}$ infectious rAAV capsids/mL are obtainable.

Because rAAV infection does not cause a cytopathic effect, plaque assays cannot be used to determine the infectious titer of an rAAV preparation. Infectious titer is thus typically measured as the median tissue culture infective dose (TCID50). In this method, a HeLa-derived AAV2 rep- and cap-expressing cell line is grown in a 96-well plate and infected with replicate 10-fold serial dilutions of the rAAV preparation, in the presence of adenovirus of serotype 5. After infection, vector genome replication is determined by quantitative PCR (qPCR) (Zen, Z. et al. (2004) "Infectious Titer Assay For Adeno-Associated Virus Vectors With Sensitivity Sufficient To Detect Single Infectious Events," Hum. Gene Ther. 15:709-715). Alternatively, the infectious titer of an rAAV preparation can be measured using the infectious center assay (ICA). This assay uses HeLa rep-cap cells and Ad, but, after incubation, involves transferring the cells to a membrane. A labeled probe that is complementary to a portion of the employed transgene is used to detect infectious centers (representing individual infected cells) via hybridization. Although more widely used, the TCID50 assay has been reported to lead to a higher background than the ICA and to overestimate vector infectivity relative to the ICA (François, A. et al. (2018) "Accurate Titration of Infectious AAV Particles Requires Measurement of Biologically Active Vector Genomes and Suitable Controls," Molec. Ther. Meth. Clin. Develop. 10:223-236). Methods of producing and purifying rAAV are described inter alia in U.S. Pat. Nos. 10,294,452; 10,161,011; 10,017,746; 9,598,703; 7,625,570; 7,439,065; 7,419,817; 7,208,315; 6,995,006; 6,989,264; 6,846,665 and 6,841,357.

Despite all such prior advances, a need remains to develop methods capable of addressing problems that presently limit the applicability of rAAV to gene therapy (Grieger, J. C. et al. (2012) "Adeno-Associated Virus Vectorology, Manufac-

*turing, and Clinical Applications*," Meth. Enzymol. 507: 229-254; Kotterman, M. A. et al. (2014) "*Engineering Adeno-Associated Viruses For Clinical Gene Therapy*," Nat. Rev. Genet. 15(7):445-451; Kwon, I. et al. (2007) "*Designer Gene Delivery Vectors: Molecular Engineering and Evolution of Adeno-Associated Viral Vectors for Enhanced Gene Transfer*," Pharm. Res. 25(3):489-499; Naso, M. F. et al. (2017) "*Adeno-Associated Virus (AAV) as a Vector for Gene Therapy*," BioDrugs 31:317-334).

The present invention is directed to improved methods for increasing the efficiency of AAV and rAAV packaging through regulation of the expression of the AAV rep and cap genes.

SUMMARY OF THE INVENTION

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

In detail, the invention provides a recombinantly-modified adeno-associated virus (AAV) helper vector that comprises an AAV helper function-providing polynucleotide, and especially an AAV helper function-providing polynucleotide that is a plasmid vector, wherein the polynucleotide comprises a non-native AAV serotype P5 or P40 promoter sequence.

The invention particularly includes the embodiment of such recombinantly-modified adeno-associated virus (AAV) helper vector wherein the AAV helper function-providing polynucleotide vector comprises a non-native AAV serotype P5 promoter sequence and/or a non-native AAV serotype P40 promoter sequence.

The invention also particularly includes the embodiment of such recombinantly-modified adeno-associated virus (AAV) helper vector wherein the non-native AAV serotype P5 or P40 promoter sequence replaces a native AAV serotype promoter sequence.

The invention also particularly includes the embodiment of such recombinantly-modified adeno-associated virus (AAV) helper vector wherein the vector additionally comprises a non-AAV helper function-providing polynucleotide.

The invention additionally provides a method for increasing the production titer of a recombinantly-modified adeno-associated virus (rAAV) that comprises a transgene cassette, wherein the method comprises culturing cells that have been transfected with:
(1) the rAAV;
(2) the above-described recombinantly-modified adeno-associated virus (AAV) helper vector that additionally comprises a non-AAV helper function-providing polynucleotide;

wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

The invention additionally provides a method for increasing the production titer of recombinantly-modified adeno-associated virus (rAAV) that comprises a transgene cassette, wherein the method comprises culturing cells that have been transfected with:
(1) the rAAV;
(2) any of the above-described recombinantly-modified adeno-associated virus (AAV) helper vectors; and
(3) an additional vector, especially a plasmid vector, that comprises a non-AAV helper function-providing polynucleotide;

wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

The invention particularly includes the embodiment of such methods, wherein the transgene cassette encodes a protein, or comprises a transcribed nucleic acid, that is therapeutic for a genetic or heritable disease or condition.

The invention also particularly includes the embodiment of such methods, wherein:
(A) the AAV helper function-providing polynucleotide of the vector encodes an AAV1 Cap protein, and the non-native AAV serotype promoter sequence is a promoter sequence of an AAV of serotype AAV3, AAV4, AAV5, AAV6, AAV7 or AAV8, or a hybrid of one or more of the serotypes;
(B) the AAV helper function-providing polynucleotide of the vector encodes an AAV2 Cap protein, and the non-native AAV serotype promoter sequence is a promoter sequence of an AAV of serotype AAV1, AAV3, AAV4, AAV5, AAV6, AAV7 or AAV8, or a hybrid of one or more of the serotypes;
(C) the AAV helper function-providing polynucleotide of the vector encodes an AAV3 Cap protein, and the non-native AAV serotype promoter sequence is a promoter sequence of an AAV of serotype AAV1, AAV4, AAV5, AAV6, AAV7 or AAV8, or a hybrid of one or more of the serotypes;
(D) the AAV helper function-providing polynucleotide of the vector encodes an AAV4 Cap protein, and the non-native AAV serotype promoter sequence is a promoter sequence of an AAV of serotype AAV1, AAV3, AAV5, AAV6, AAV7 or AAV8, or a hybrid of one or more of the serotypes;
(E) the AAV helper function-providing polynucleotide of the vector encodes an AAV5 Cap protein, and the non-native AAV serotype promoter sequence is a promoter sequence of an AAV of serotype AAV1, AAV3, AAV4, AAV6, AAV7 or AAV8, or a hybrid of one or more of the serotypes;
(F) the AAV helper function-providing polynucleotide of the vector encodes an AAV6 Cap protein, and the non-native AAV serotype promoter sequence is a promoter sequence of an AAV of serotype AAV1, AAV3, AAV4, AAV5, AAV7 or AAV8, or a hybrid of one or more of the serotypes;
(G) the AAV helper function-providing polynucleotide of the vector encodes an AAV7 Cap protein, and the non-native AAV serotype promoter sequence is a promoter sequence of an AAV of serotype AAV1, AAV3, AAV4, AAV5, AAV6 or AAV8, or a hybrid of one or more of the serotypes;

(H) the AAV helper function-providing polynucleotide of the vector encodes an AAV8 Cap protein, and the non-native AAV serotype promoter sequence is a promoter sequence of an AAV of serotype AAV1, AAV3, AAV4, AAV5, AAV6 or AAV7, or a hybrid of one or more of the serotypes.

The invention also particularly includes the embodiment of such methods, wherein the cells are human embryonic kidney cells, baby hamster kidney cells or sf9 insect cells.

The invention additionally provides a pharmaceutical composition that comprises the recombinantly-modified adeno-associated virus (rAAV) produced by any of the above-listed methods, and a pharmaceutically acceptable carrier.

P5-RC constructs are derivatives of parental plasmid AAV RC that have been modified to direct expression of the AAV rep gene using a non-native P5 promoter (i.e., an AAV P5 promoter that is not natively present within the AAV rep gene of the vector (downward striped box)) in lieu of the native AAV serotype P5 promoter (solid black box); P5-RC constructs direct expression of the AAV rep and cap genes using the native AAV serotype P19 and P40 promoter sequences (solid black boxes) of the parent vector. P40-RC constructs are derivatives of parental plasmid AAV RC that have been modified to direct expression of the AAV cap gene using a non-native P40 promoter (i.e., an AAV P40 promoter that is not natively present within the AAV rep gene (upward striped box)) of the vector in lieu of the native AAV serotype P40 promoter (solid black box); P40-RC constructs direct expression of the AAV rep gene using the native AAV serotype P5 and P19 promoter sequences (solid black boxes) of the parent vector. P5/P40-RC constructs are derivatives of parental plasmid AAV RC that have been modified to direct expression of the AAV rep gene using a non-native P5 promoter (i.e., an AAV P5 promoter that is not natively present within the AAV rep gene of the vector (downward striped box)) in lieu of the native AAV serotype P5 promoter (solid black box). P5/P40-RC constructs have additionally been modified to direct expression to direct expression of the AAV cap gene using a non-native P40 promoter (i.e., an AAV P40 promoter that is not natively present within the AAV rep gene (upward striped box)) of the vector in lieu of the native AAV serotype P40 promoter (solid black box). P40-RC constructs direct expression of the AAV rep gene using the native AAV serotype P19 promoter sequences (solid black boxes) of the parent vector. The sequences of the promoter regions are shown in Table 1.

Figure 11:
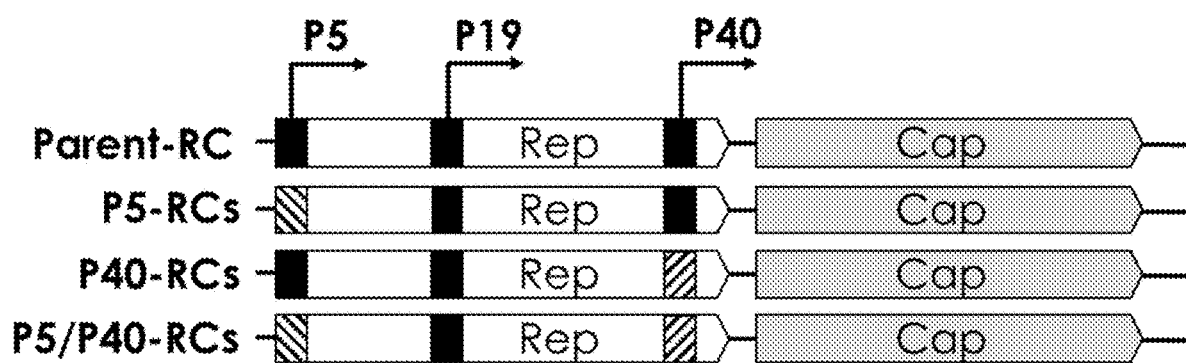
FIG. 11 shows the overall structure and approach followed for the development of the exemplary AAV helper constructs described herein. The parent construct (pAAV-RC2; Parent-RC) comprises AAV2 serotype promoter sequences for the P5 and P19 promoters (solid black boxes) that direct expression of the native AAV2 rep gene (white boxed gene), which encodes the Rep proteins, as well as the AAV2 serotype promoter sequence of the P40 promoter (solid black box) that directs expression of the native AAV2 cap gene (gray boxed gene), which encodes the Cap proteins.
Figure 12A:
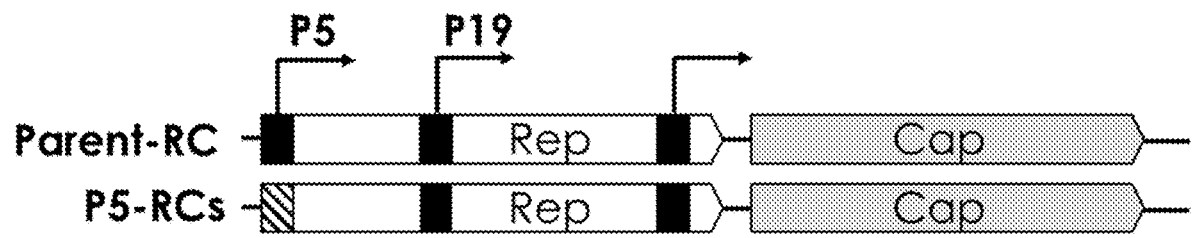
Figure 12B:
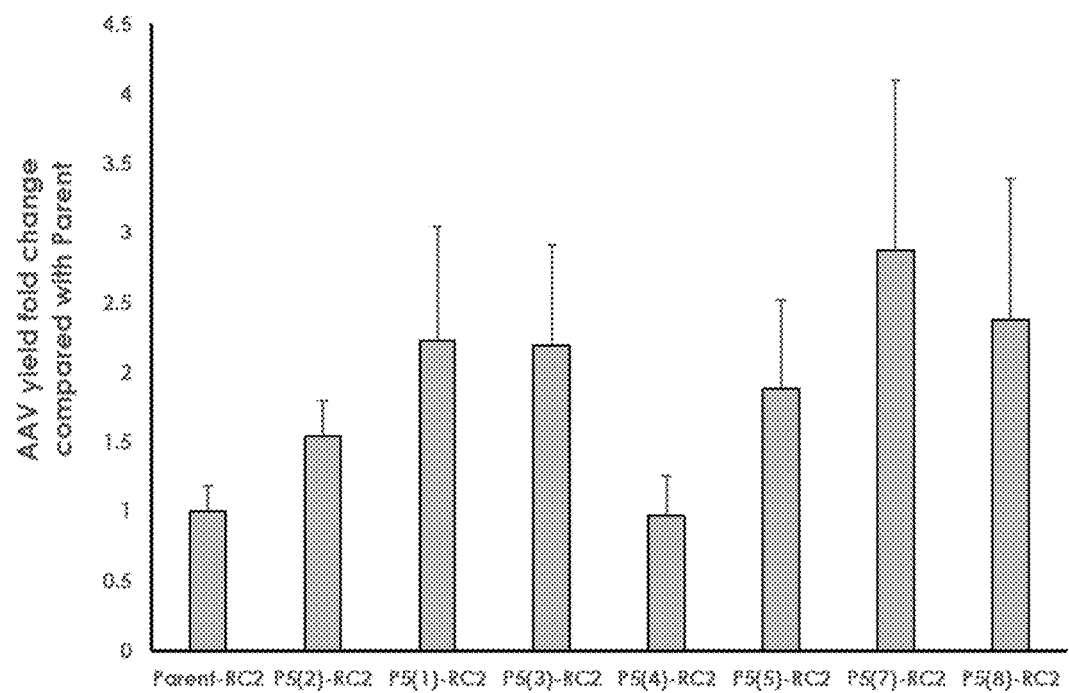

FIGS. 12A-12B show the production titers of rAAV obtained by modifying a parental RC2 vector to comprise a non-native P5 promoter sequence (FIG. 11; FIG. 12A; downward striped rectangle) in lieu of the AAV2 P5 promoter that is natively associated with the rep gene of such vector. The P19 and P40 promoters are both native AAV2 serotype promoter sequences (solid black rectangles). FIG. 12B shows the production titers of rAAV obtained using such AAV helper plasmid vectors. The following constructs were employed: Parent-RC2, P5(2)-RC2, P5(1)-RC2, P5(3)-RC2, P5(4)-RC2, P5(5)-RC2, P5(7)-RC2, and P5(8)-RC2. The sequences of the promoter regions are shown in Table 1. The production titers of rAAV were obtained using a triple plasmid transfection system with an rAAV, and an Ad helper plasmid that provided the required adenoviral functions.

Figure 13A:
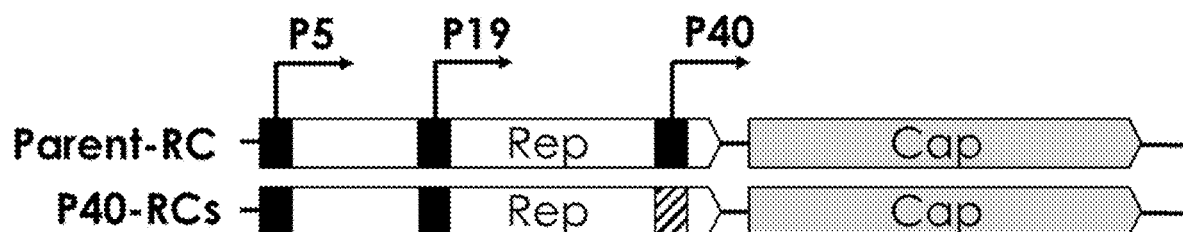
Figure 13B:
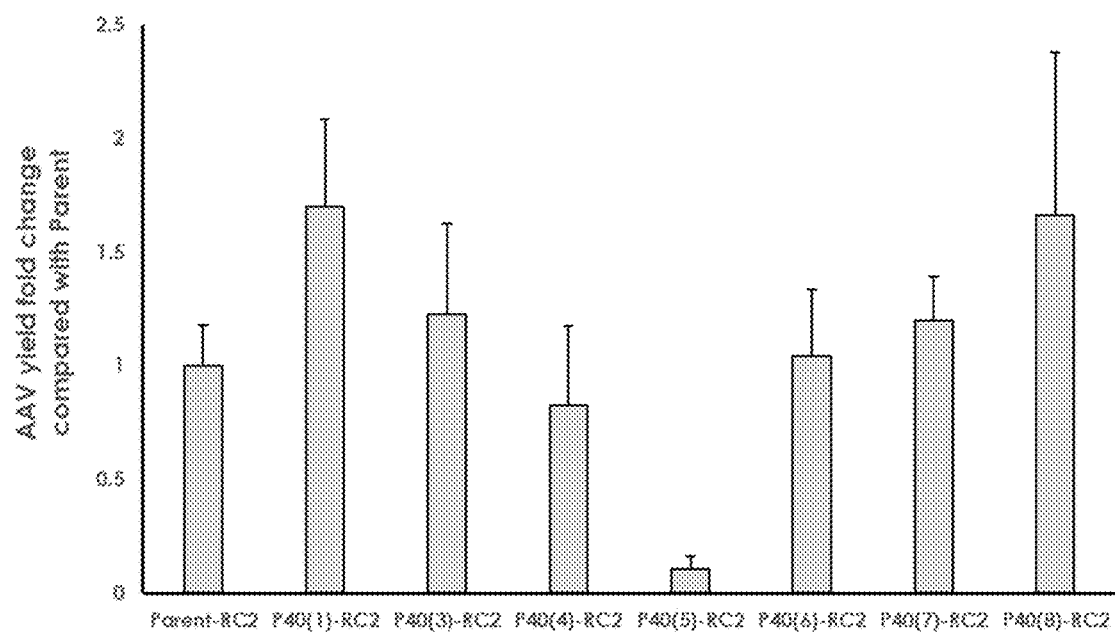

FIGS. 13A-13B show the production titers of rAAV obtained by modifying a parental RC2 vector to comprise a non-native P40 promoter sequence (FIG. 11; FIG. 13A; upward striped rectangle) in lieu of the AAV2 serotype P40 promoter of the parental vector. The P5 and P19 promoters are both native AAV2 serotype promoter sequences (solid black rectangle). FIG. 13B shows the production titers of rAAV obtained using such AAV helper plasmid vectors. The following constructs were employed: Parent-RC2, P40(1)-RC2, P40(3)-RC2, P40(4)-RC2, P40(5)-RC2, P40(6)-RC2, P40(7)-RC2, and P40(8)-RC2. The sequences of the promoter regions are shown in Table 1. The production titers of rAAV were obtained using a triple plasmid transfection system with an rAAV, and an Ad helper plasmid that provided the required adenoviral functions.

Figure 14A:
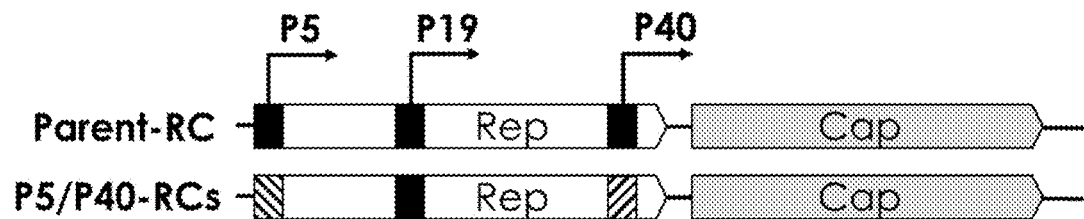
Figure 14B:
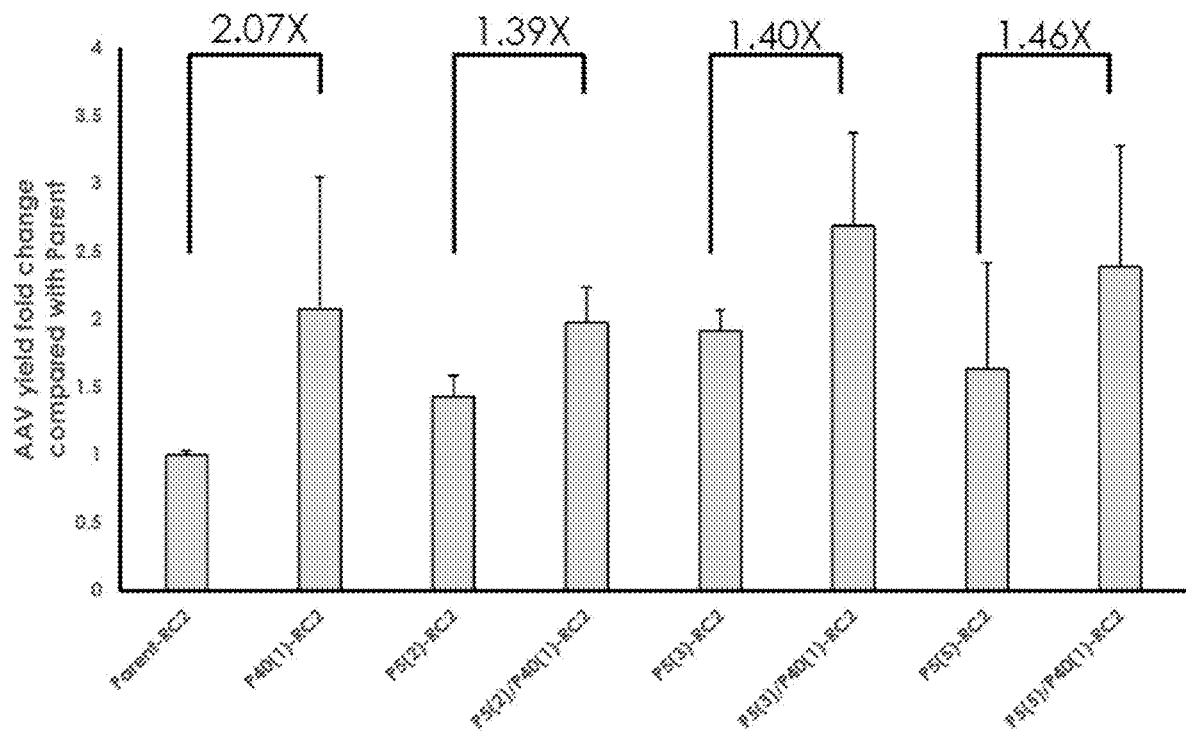

FIGS. 14A-14B show the production titers of rAAV obtained by modifying a parental RC2 vector to comprise a non-native P5 promoter sequence and/or a non-native P40 promoter sequence (FIG. 11; FIG. 14A; P5, downward striped rectangle; P40, upward striped rectangle) in lieu of the AAV2 serotype P5 and P40 promoters of the parental vector. The P19 promoter is a native AAV2 serotype promoter sequences (solid black rectangle). The following constructs were employed: Parent-RC2, P5(2)-RC2, P5(3)-RC2, P5(5)-RC2, P40(1)-RC2, P5(2)/P40(1)-RC2, P5(3)/P40(1)-RC2, and P5(5)/P40(1)-RC2. The sequences of the promoter regions are shown in Table 1. FIG. 14B shows the production titers of rAAV obtained using such AAV helper plasmid vectors. The production titers of rAAV were obtained using a triple plasmid transfection system with an rAAV, and an Ad helper plasmid that provided the required adenoviral functions.

Figure 15A:
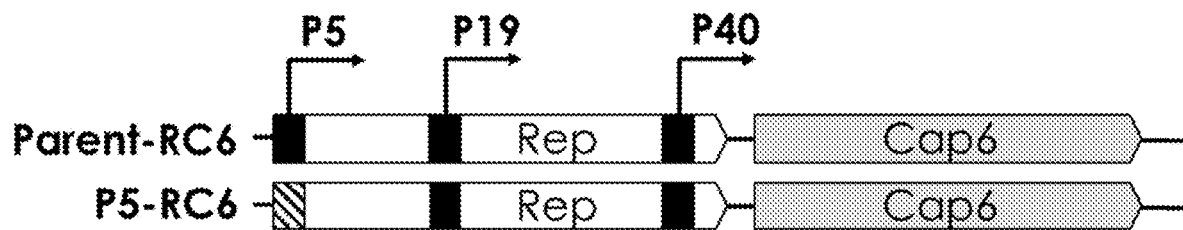
Figure 15B:
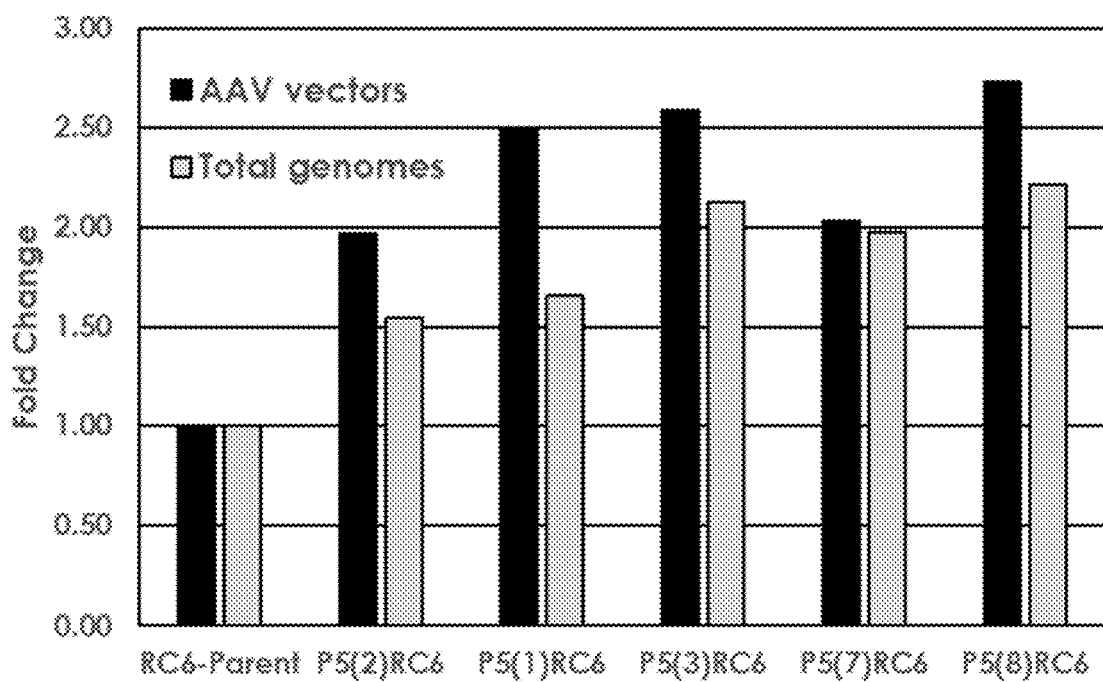
Figure 15C:
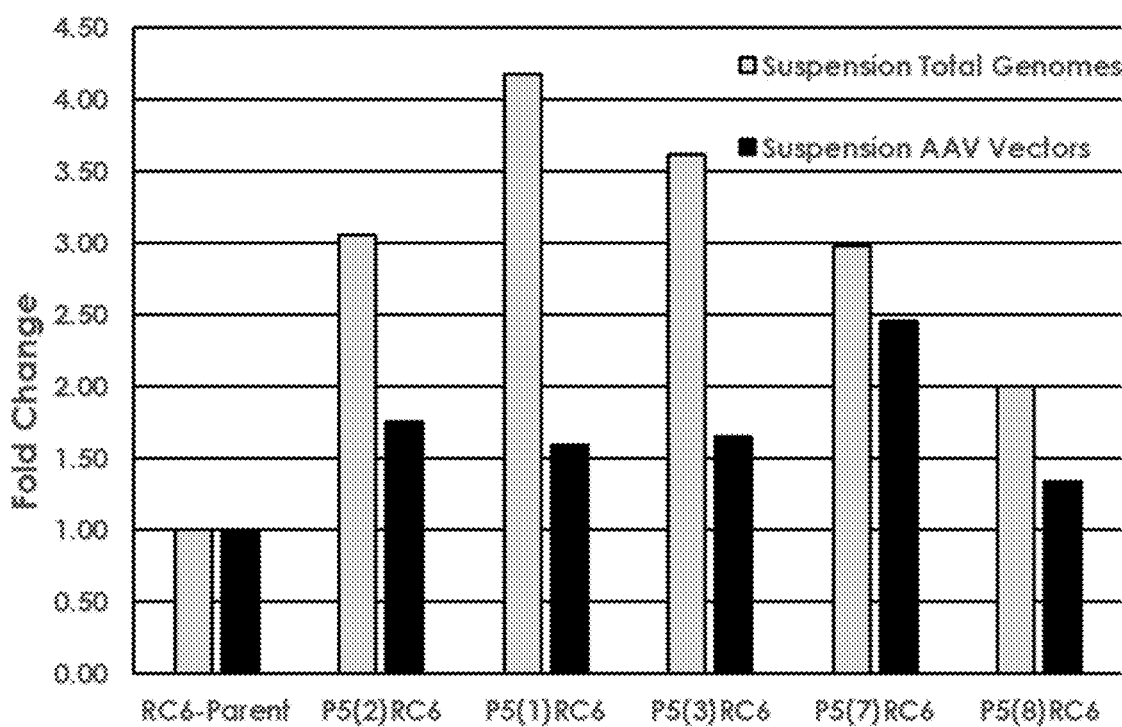

FIGS. 15A-15C show the production titers of rAAV obtained by modifying a parental RC6 vector to comprise a non-native P5 promoter sequence (FIG. 11; FIG. 15A; downward striped rectangle) in lieu of the AAV2 serotype P5 promoter that is natively associated with the rep gene of such vector. The P19 and P40 promoters are both native AAV2 serotype promoter sequences (solid black rectangles). The following constructs were employed: Parent-RC6, P5(1)-RC6, P5(2)-RC6, P5(3)-RC6, P5(7)-RC6 and P5(8)-RC6. The sequences of the promoter regions are shown in Table 1. The production titers of rAAV were obtained (FIGS. 15B-15C) using a triple plasmid transfection system with an rAAV, and an Ad helper plasmid that provided the required adenoviral functions.

Figure 16A:
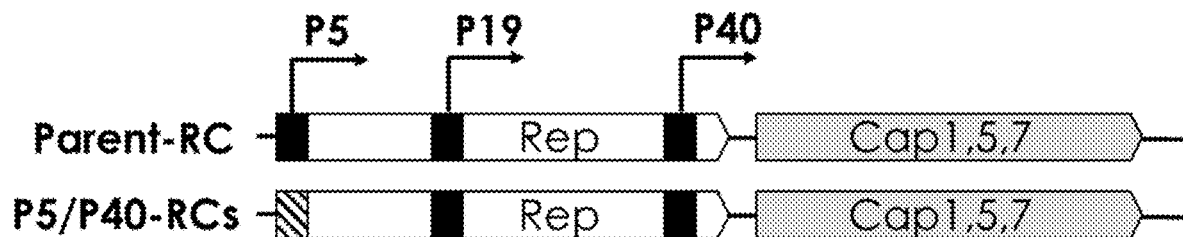
Figure 16B:
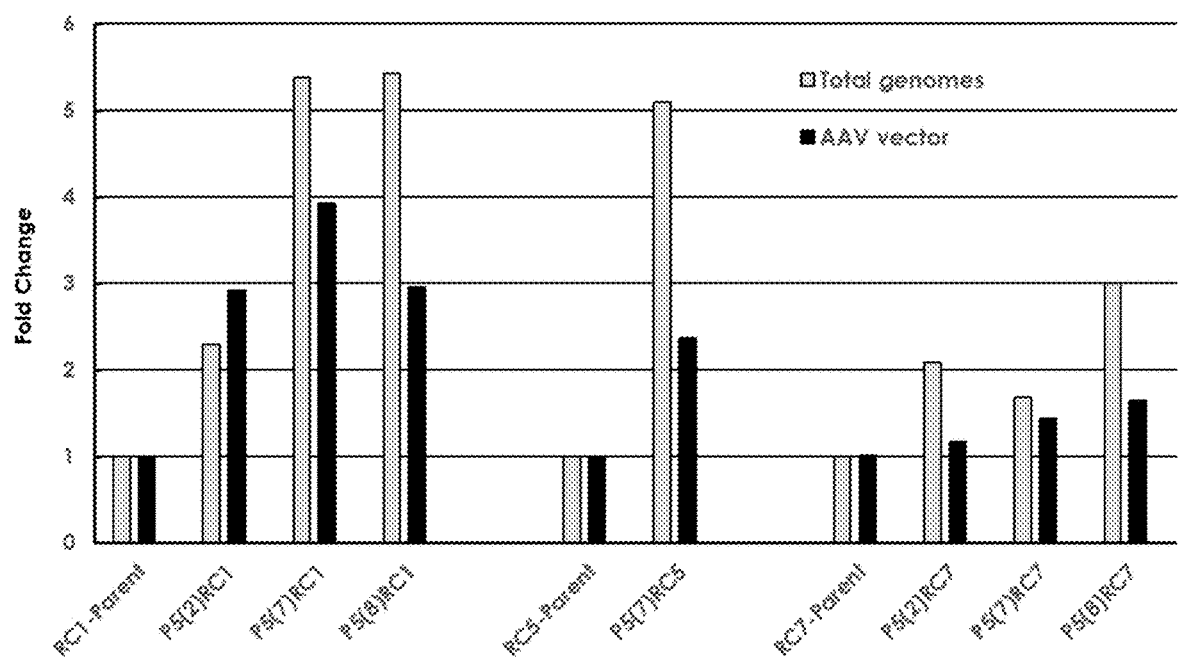

FIGS. 16A-16B show the production titers of rAAV obtained by modifying a parental RC1, RC5, or RC7 vector to comprise a non-native P5 promoter sequence (FIG. 11; FIG. 16A; downward striped rectangle) in lieu of the AAV2 serotype P5 promoter that is natively associated with the rep gene of such vectors. The P19 and P40 promoters are both native AAV2 serotype promoter sequences (solid black rectangles). The following constructs were employed: Parent-RC1, Parent-RC5, Parent-RC7, P5(2)-RC1, P5(7)-RC1, P5(8)-RC1, P5(7)-RC5, P5(2)-RC7, P5(7)-RC7 and P5(8)-RC7. The sequences of the promoter regions are shown in Table 1. The production titers of rAAV (FIG. 16B) were obtained using a triple plasmid transfection system with an rAAV, and an Ad helper plasmid that provided the required adenoviral functions.

DETAILED DESCRIPTION OF THE INVENTION

I. The Methods of the Present Invention

The present invention is directed to recombinantly-modified adeno-associated virus (AAV) helper vectors that are capable of increasing the packaging efficiency of recombinantly-modified adeno-associated virus (rAAV) and their use to improve the packaging efficiency of such rAAV. The present invention is particularly directed to recombinantly-modified adeno-associated virus (AAV) helper vectors that have been further modified to replace (or augment) the P5 and/or P40 promoter sequences that are natively associated with the Rep proteins encoded by such rAAV with AAV P5 and/or P40 promoters that are associated with the Rep proteins of an rAAV of different serotype. The use of such substitute or additional promoter sequences causes increased production of recombinantly-modified adeno-associated virus.

The present invention is based in part on the recognition that high levels of Rep and Cap proteins increase the amount of rAAV genomes particles produced and, consequently, the efficiency of rAAV packaging, and thus result in high production titers of rAAV stocks. It has been unexpectedly found that by replacing the AAV P5 and/or P40 promoters that direct the expression of the Cap proteins with different AAV P5 and/or P40 promoters, or by adding such different AAV P5 and/or P40 promoters in addition to those initially present, causes the desired high levels of rAAV to be attained. AAV Rep proteins are described in U.S. Pat. Nos. 10,214,730; 7,122,348; 6,821,511; 6,753,419; 9,441,206; and 7,115,391.

As discussed above, AAV and rAAV are characterized based on their serotype, which is determined by their capsid proteins (Colella, P. et al. (2018) "*Emerging Issues in AAV-Mediated In Vivo Gene Therapy*," Molec. Ther. Meth. Clin. Develop. 8:87-104; Hocquemiller, M. et al. (2016) "*Adeno-Associated Virus-Based Gene Therapy for CNS Diseases*," Hum. Gene Ther. 27(7):478-496; Lisowski, L. et al. (2015) "*Adeno-Associated Virus Serotypes For Gene Therapeutics,*" 24:59-67; U.S. Pat. Nos. 10,301,650; 10,266,846; 10,265,417; 10,214,785; 10,214,566; 10,202,657; 10,046, 016; 9,884,071; 9,856,539; 9,737,618; 9,677,089; 9,458, 517; 9,457,103; 9,441,244; 9,193,956; 8,846,389; 8,507, 267; 7,906,111; 7,479,554; 7,186,552; 7,105,345; 6,984, 517; 6,962,815; and 6,733,757). By forming AAV and rAAV in the presence of AAV helper function-providing polynucleotides that encode two or more capsid proteins of different serotype, one can produce AAV and rAAV having "hybrid" serotypes. Such AAV and rAAV exhibit the combined trophism of AAV and rAAV having each of such capsid proteins.

The Rep proteins of the different AAV serotypes differ, however, since such proteins are not structural proteins, the differences do not contribute to the observed serotype of an AAV.

Figure 1:
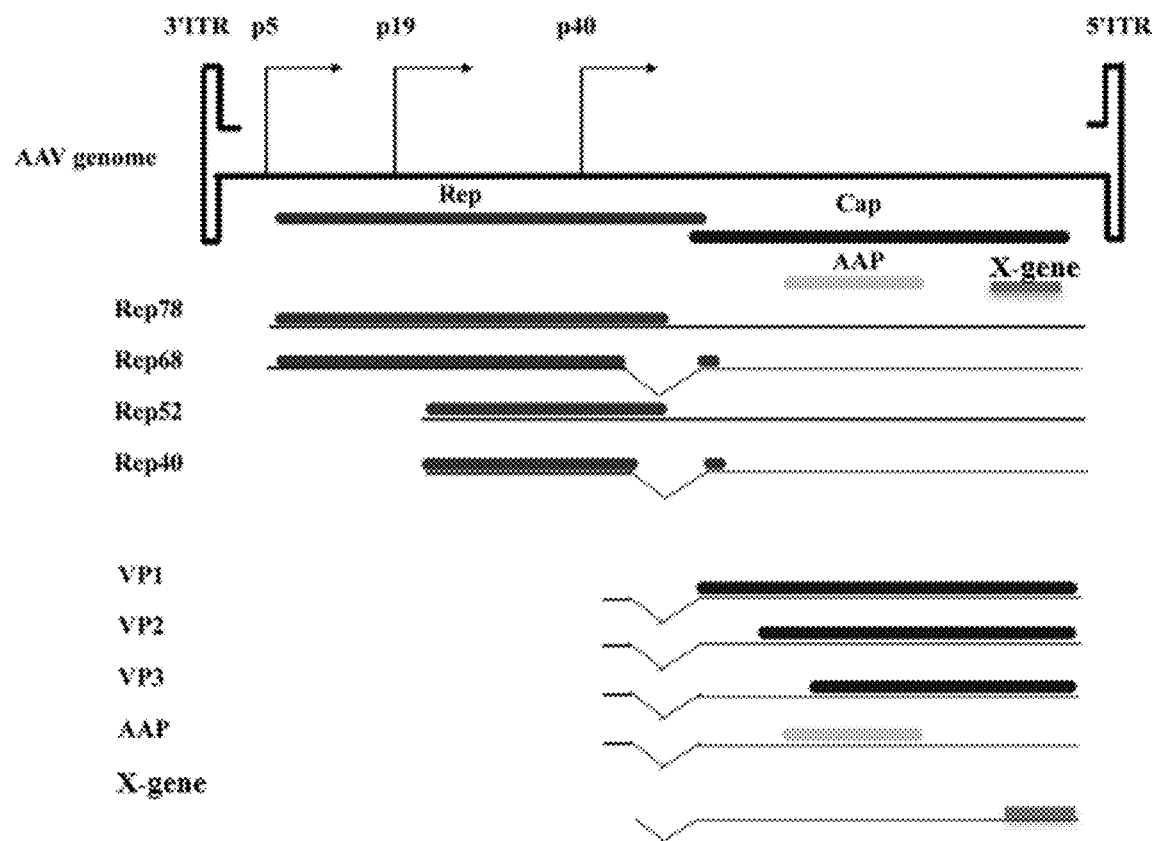
FIG. 1 provides a schematic genetic map of the wild-type (Wt) AAV genome.
Figure 2:
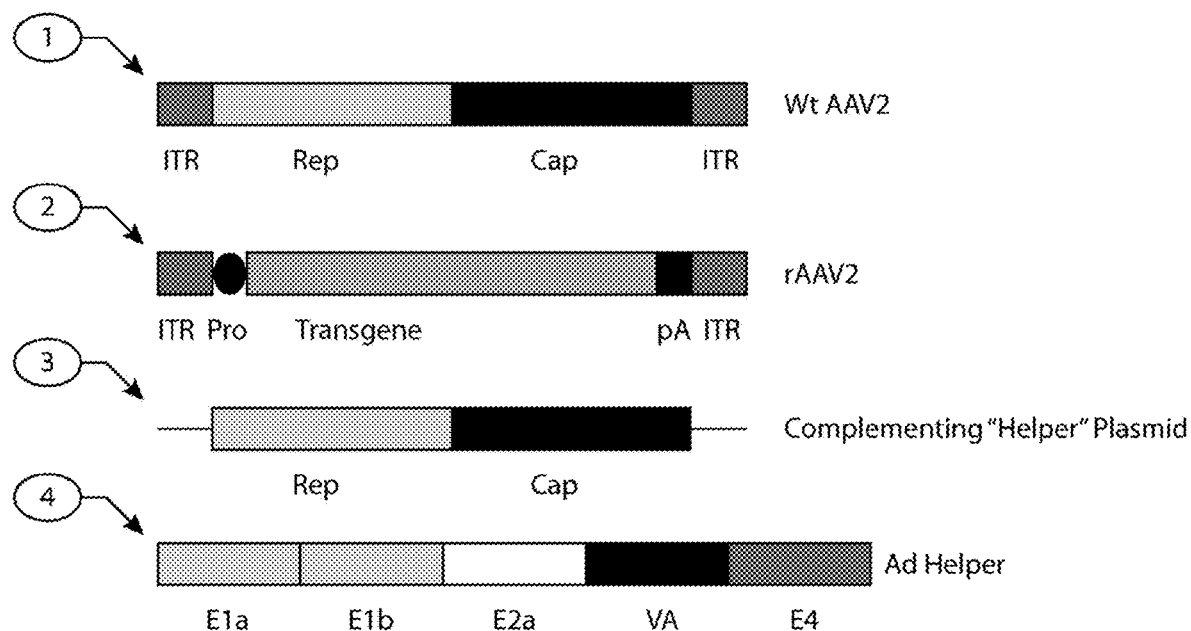
FIG. 2 provides a schematic of the structural domain of the wild-type AAV2 genome (1), a recombinant AAV (rAAV) (2), complementing "AAV helper plasmid" (3) and an adenovirus helper plasmid ("Ad helper plasmid") (4). The wild-type (Wt) AAV2 (1) is composed of AAV-specific palindromic inverted terminal repeated sequences (ITR), a 5' half containing genes that encode the Rep proteins and a 3' half containing genes that encode the Cap proteins. The rAAV (2) is formed by replacing the Rep- and Cap-encoding genes of the wild-type (Wt) AAV2 (1) with a transgene cassette that comprises a promoter (Pro), the exogenous transgene of interest, and a polyadenylation site (pA). In order to produce the rAAV (2), a complementing "AAV helper" plasmid vector (3) and an adenovirus helper plasmid vector (Ad helper plasmid) (4) are provided. The complementing AAV helper plasmid (3) provides Rep and Cap proteins. The Ad helper plasmid (4) provides adenovirus proteins E1a, E1b, E2a, VA and E4.

As used herein, the term "AAV" is intended to denote adeno-associated virus, and may be used to refer to the virus itself or derivatives thereof. The term covers all subtypes and both naturally-occurring and recombinant forms. As used herein, the term "rAAV" is intended to denote a recombinantly-modified version of AAV that comprises a polynucleotide sequence not of AAV origin (i.e., a polynucleotide heterologous to AAV). The rAAV may be single-stranded or double-stranded, and may be composed of deoxyribonucleotides or ribonucleotides. As discussed above, rAAV typically lack certain AAV genes and thus are produced using a double plasmid transfection system, or more preferably a triple plasmid transfection system that comprises a plasmid vector that comprises an AAV helper function-providing polynucleotide, a plasmid vector that comprises a non-AAV helper function-providing polynucleotide, and the rAAV plasmid vector (FIG. 2). In one embodiment, the AAV helper function-providing polynucleotide of such double or triple transfection systems may comprise more than one rep and/or cap gene, so as to be capable of forming rAAV having hybrid serotypes. In another embodiment, a second or additional AAV helper function-providing polynucleotide (for example on a second or additional plasmid vector) may be provided to permit the formation of rAAV having hybrid serotypes.

A. Illustrative AAV Helper Function-Providing Polynucleotides

As used herein, the term "AAV helper functions" denotes AAV proteins (e.g., Rep and Cap) and/or polynucleotides of AAV that are required for the replication and packaging of an rAAV. Such AAV helper functions are provided by an "AAV helper function-providing polynucleotide," which as such term is used herein is a virus, plasmid vector, a non-plasmid vector, or a polynucleotide that has been integrated into a cellular chromosome, that provides AAV helper functions. AAV helper plasmids that may be used in accordance with the present invention to provide AAV helper functions include pAAV-RC (Agilent; Addgene; Cell Biolabs), pAAV-RC1, pAAV-RC2, pAAV-RC5, pAAV-RC6, and pAAV-RC7.

1. Plasmid pAAV-RC1

Figure 3:
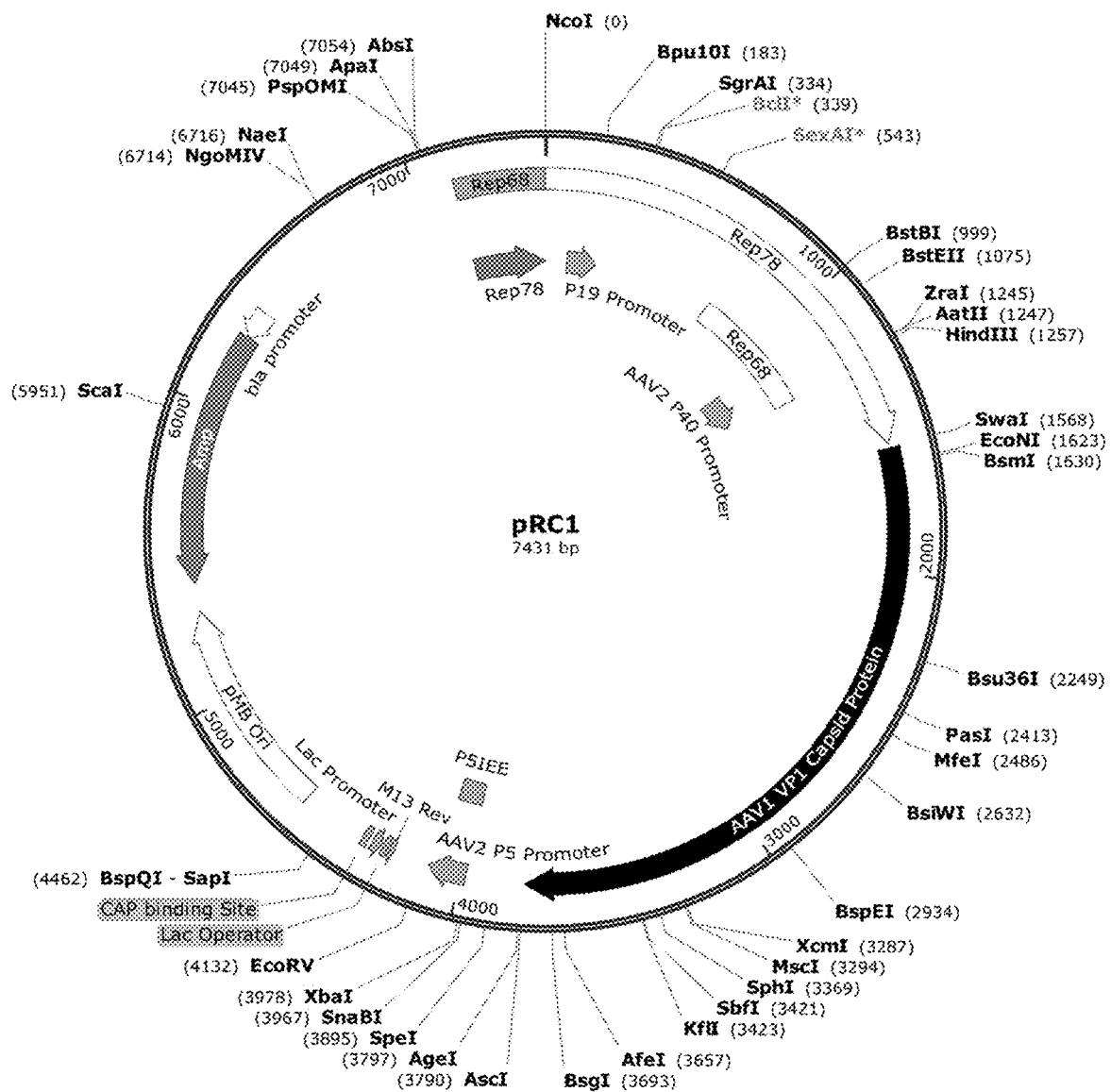
FIG. 3 shows a map of the AAV helper plasmid vector pAAV-RC1 (SEQ ID NO:1).

Plasmid pAAV-RC1 (SEQ ID NO:1; FIG. 3) is an AAV helper plasmid that expresses AAV1 serotype capsid proteins that may be used in accordance with the present invention to provide AAV helper functions. The P5 and P40 promoters of pAAV-RC1 are AAV2 serotype promoters (SEQ ID NO:10 and SEQ ID NO:18, respectively).

Coding Strand of Plasmid pAAV-RC1 (SEQ ID NO: 1):
catggttttg ggacgtttcc tgagtcagat tcgcgaaaaa ctgattcaga
gaatttaccg cgggatcgag ccgactttgc caaactggtt cgcggtcaca
aagaccagaa atggcgccgg aggcgggaac aaggtggtgg atgagtgcta
catccccaat tacttgctcc ccaaaaccca gcctgagctc agtgggcgt
ggactaatat ggaacagtat ttaagcgcct gtttgaatct cacggagcgt
aaacggttgg tggcgcagca tctgacgcac gtgtcgcaga cgcaggagca
gaacaaagag aatcagaatc ccaattctga tgcgccggtg atcagatcaa
aaacttcagc caggtacatg agctggtcg ggtggctcgt ggacaagggg
attacctcgg agaagcagtg gatccaggag gaccaggcct catacatctc
cttcaatgcg gcctccaact cgcggtccca atcaaggct gccttggaca
atgcgggaaa gattatgagc ctgactaaaa ccgcccccga ctacctggtg
ggccagcagc ccgtggagga catttccagc aatcggattt ataaaatttt
ggaactaaac gggtacgatc cccaatatgc ggcttccgtc tttctgggat
gggccacgaa aaagttcggc aagaggaaca ccatctggct gtttgggcct
gcaactaccg ggaagaccaa catcgcggag gccatagccc acactgtgcc
cttctacggg tgcgtaaact ggaccaatga aactttccc ttcaacgact
gtgtcgacaa gatggtgatc tggtgggagg aggggaagat gaccgccaag
gtcgtggagt cggccaaagc cattctcgga ggaagcaagg tgcgcgtgga
ccagaaatgc aagtcctcgg cccagataga cccgactccc gtgatcgtca
cctccaacac caacatgtgc gccgtgattg acgggaactc aacgaccttc
gaacaccagc agccgttgca agaccggatg ttcaaatttg aactcacccg
ccgtctggat catgactttg gaaggtcac caagcaggaa gtcaaagact
ttttccggtg ggcaaaggat cacgtggttg aggtggagca tgaattctac
gtcaaaaagg gtggagccaa gaaaagaccc gcccccagtg acgcagatat
aagtgagccc aaacgggtgc gcgagtcagt tgcgcagcca tcgacgtcag
acgcggaagc ttcgatcaac tacgcagaca ggtaccaaaa caatgttct
cgtcacgtgg gcatgaatct gatgctgttt ccctgcagac aatgcgagag
aatgaatcag aattcaaata tctgcttcac tcacggacag aaagactgtt
tagagtgctt tccccgtgtca gaatctcaac ccgtttctgt cgtcaaaaag
gcgtatcaga aactgtgcta cattcatcat atcatgggaa aggtgccaga
cgcttgcact gcctgcgatc tggtcaatgt ggatttggat gactgcatct
ttgaacaata aatgatttaa atcaggtatg gctgccgatg gttatcttcc
agattggctc gaggacaacc tctctgaggg cattcgcgag tggtgggact
tgaaacctgg agccccgaag cccaaagcca accagcaaaa gcaggacgac
ggccggggtc tggtgcttcc tggctacaag tacctcggac ccttcaacgg
actcgacaag ggggagcccg tcaacgcggc ggacgcagcg ccctcgagc
acgacaaggc ctacgaccag cagctcaaag cgggtgacaa tccgtacctg
cggtataacc acgccgacgc cgagtttcag gagcgtctgc aagaagatac
gtcttttggg ggcaacctcg gcgagcagt cttccaggcc aagaagcggg
ttctcgaacc tctcggtctg gttgaggaag gcgctaagac ggctcctgga -continued

```
aagaaacgtc cggtagagca gtcgccacaa gagccagact cctcctcggg catcggcaag acaggccagc agcccgctaa aaagagactc aattttggtc agactggcga ctcagagtca gtccccgatc cacaacctct cggagaacct ccagcaaccc ccgctgctgt gggacctact acaatggctt caggcggtgg cgcaccaatg gcagacaata acgaaggcgc cgacggagtg ggtaatgcct caggaaattg gcattgcgat tccacatggc tgggcgacag agtcatcacc accagcaccc gcacctgggc cttgcccacc tacaataacc acctctacaa gcaaatctcc agtgcttcaa cgggggccag caacgacaac cactacttcg gctacagcac cccctggggg tattttgatt tcaacagatt ccactgccac ttttcaccac gtgactggca gcgactcatc aacaacaatt ggggattccg gcccaagaga ctcaacttca aactcttcaa catccaagtc aaggaggtca cgacgaatga tggcgtcaca accatcgcta ataaccttac cagcacggtt caagtcttct cggactcgga gtaccagctt ccgtacgtcc tcggctctgc gcaccagggc tgcctccctc cgttcccggc ggacgtgttc atgattccgc aatacggcta cctgacgctc aacaatggca gccaagccgt gggacgttca tcctttact gcctggaata tttcccttct cagatgctga gaacgggcaa caacttacc ttcagctaca cctttgagga agtgcctttc cacagcagct acgcgcacag ccagagcctg gaccggctga tgaatcctct catcgaccaa tacctgtatt acctgaacag aactcaaaat cagtccggaa gtgcccaaaa caaggacttg ctgtttagcc gtgggtctcc agctggcatg tctgttcagc ccaaaaactg gctacctgga cctgttatc ggcagcagcg cgtttctaaa acaaaaacag acaacaacaa cagcaatttt acctggactg gtgcttcaaa atataacctc aatgggcgtg aatccatcat caaccctggc actgctatgg cctcacacaa agacgacgaa gacaagttct ttcccatgag cggtgtcatg attttggaa aagagagcgc cggagcttca aacactgcat tggacaatgt catgattaca gacgaagagg aaattaaagc cactaaccct gtggccaccg aaagatttgg gaccgtggca gtcaatttcc agagcagcag cacagaccct gcgaccggag atgtgcatgc tatgggagca ttacctggca tggtgtggca agatagagac gtgtacctgc agggtcccat ttgggccaaa attcctcaca cagatggaca ctttcacccg tctcctctta tgggcggctt tggactcaag aacccgcctc ctcagatcct catcaaaaac acgcctgttc ctgcgaatcc tccggcggag ttttcagcta caaagtttgc ttcattcatc acccaatact ccacaggaca agtgagtgtg gaaattgaat gggagctgca gaaagaaaac agcaagcgct ggaatcccga agtgcagtac acatccaatt atgcaaaatc tgccaacgtt gattttactg tggacaacaa tggactttat actgagcctc gccccattgg cacccgttac cttacccgtc cctgtaagg cgcgccaccg gttgcttgtt aatcaataaa ccgtttaatt cgtttcagtt gaactttggt ctctgcgtat ttctttctta tctagtttcc atgctctagg atccactagt aacggccgcc agtgtgctgg aattcggctt tgtagttaat gattaacccg ccatgctact tatctacgta gccatgctct agaggtcctg tattagaggt cacgtgagtg ttttgcgaca ttttgcgaca ccatgtggtc acgctgggta
```

-continued

```
tttaagcccg agtgagcacg cagggtctcc attttgaagc gggaggtttg aacgcgcagc cgccaagccg aattctgcag atatccaaac actggcggcc gctcgactag agcggccgcc accgcggtgg agctccagct tttgttccct ttagtgaggg ttaattgcgc gcttggcgta atcatggtca tagctgtttc ctgtgtgaaa ttgttatccg ctcacaattc cacacaacat acgagccgga agcataaagt gtaaagcctg gggtgcctaa tgagtgagct aactcacatt aattgcgttg cgctcactgc ccgctttcca gtcgggaaac ctgtcgtgcc agctgcatta atgaatcggc caacgcgcgg ggagaggcgg tttgcgtatt gggcgctctt ccgcttcctc gctcactgac tcgctgcgct cggtcgttcg gctgcggcga gcggtatcag ctcactcaaa ggcggtaata cggttatcca cagaatcagg ggataacgca ggaaagaaca tgtgagcaaa aggccagcaa aaggccagga accgtaaaaa ggccgcgttg ctggcgtttt tccataggct ccgcccccct gacgagcatc acaaaaatcg acgctcaagt cagaggtggc gaaacccgac aggactataa agataccagg cgtttccccc tggaagctcc ctcgtgcgct ctcctgttcc gaccctgccg cttaccggat acctgtccgc cttttctccct tcgggaagcg tggcgctttc tcatagctca cgctgtaggt atctcagttc ggtgtaggtc gttcgctcca agctgggctg tgtgcacgaa ccccccgttc agcccgaccg ctgcgcctta tccggtaact atcgtcttga gtccaacccg gtaagacacg acttatcgcc actggcagca gccactggta acaggattag cagagcgagg tatgtaggcg gtgctacaga gttcttgaag tggtggccta actacggcta cactagaaga acagtatttg gtatctgcgc tctgctgaag ccagttacct tcggaaaaag agttggtagc tcttgatccg gcaaacaaac caccgctggt agcggtggtt tttttgtttg caagcagcag attacgcgca gaaaaaaagg atctcaagaa gatcctttga tcttttctac ggggtctgac gctcagtgga acgaaaactc acgttaaggg attttggtca tgagattatc aaaaaggatc ttcacctaga tccttttaaa ttaaaaatga agttttaaat caatctaaag tatatatgag taaacttggt ctgacagtta ccaatgctta atcagtgagg cacctatctc agcgatctgt ctatttcgtt catccatagt tgcctgactc cccgtcgtgt agataactac gatacgggag ggcttaccat ctggccccag tgctgcaatg ataccgcgag acccacgctc accggctcca gatttatcag caataaacca gccagccgga agggccgagc gcagaagtgg tcctgcaact ttatccgcct ccatccagtc tattaattgt tgccgggaag ctagagtaag tagttcgcca gttaatagtt tgcgcaacgt tgttgccatt gctacaggca tcgtggtgtc acgctcgtcg tttggtatgg cttcattcag ctccggttcc caacgatcaa ggcgagttac atgatccccc atgttgtgca aaaaagcggt tagctccttc ggtcctccga tcgttgtcag aagtaagttg gccgcagtgt tatcactcat ggttatggca gcactgcata attctcttac tgtcatgcca tccgtaagat gcttttctgt gactggtgag tactcaacca agtcattctg agaatagtgt atgcggcgac cgagttgctc ttgcccggcg tcaatacggg ataataccgc gccacatagc agaactttaa
```

```
aagtgctcat cattggaaaa cgttcttcgg ggcgaaaact ctcaaggatc ttaccgctgt tgagatccag ttcgatgtaa cccactcgtg cacccaactg atcttcagca tcttttactt tcaccagcgt ttctgggtga gcaaaaacag gaaggcaaaa tgccgcaaaa aagggaataa gggcgacacg gaaatgttga atactcatac tcttcctttt tcaatattat tgaagcattt atcagggtta ttgtctcatg agcggataca tatttgaatg tatttagaaa aataaacaaa tagggggttcc gcgcacattt ccccgaaaag tgccacctaa attgtaagcg ttaatatttt gttaaaattc gcgttaaatt tttgttaaat cagctcattt tttaaccaat aggccgaaat cggcaaaatc ccttataaat caaaagaata gaccgagata gggttgagtg ttgttccagt ttggaacaag agtccactat taaagaacgt ggactccaac gtcaaagggc gaaaaaccgt ctatcagggc gatgcccac tacgtgaacc atcaccctaa tcaagttttt tggggtcgag gtgccgtaaa gcactaaatc ggaaccctaa agggagcccc cgatttagag cttgacgggg aaagccggcg aacgtggcga gaaaggaagg gaagaaagcg aaaggagcgg gcgctagggc gctggcaagt gtagcggtca cgctgcgcgt aaccaccaca cccgccgcgc ttaatgcgcc gctacagggc gcgtcccatt cgccattcag gctgcgcaac tgttgggaag ggcgatcggt gcgggcctct tcgctattac gccagctggc gaaaggggga tgtgctgcaa ggcgattaag ttgggtaacg ccagggtttt cccagtcacg acgttgtaaa acgacggcca gtgagcgcgc gtaatacgac tcactatagg gcgaattggg taccgggccc cccctcgagg tcgacggtat cggggagct cgcagggtct ccattttgaa gcgggaggtt tgaacgcgca gccgccatgc cggggtttta cgagattgtg attaaggtcc ccagcgacct tgacgagcat ctgcccggca tttctgacag ctttgtgaac tgggtggccg agaaggaatg ggagttgccg ccagattctg acatggatct gaatctgatt gagcaggcac ccctgaccgt ggccgagaag ctgcagcgcg actttctgac ggaatggcgc cgtgtgagta aggccccgga ggctcttttc tttgtgcaat ttgagaaggg agagagctac ttccacatgc acgtgctcgt ggaaaccacc ggggtgaaat c
```

In SEQ ID NO:1, residues 1-1561 of pAAV-RC1 encode the Rep protein, Rep78 (with residues 95-221 corresponding to the AAV2 P19 promoter and residues 1075-1254 corresponding to the AAV2 P40 promoter (SEQ ID NO:18)); residues 1578-3788 encode the AAV1 VP1 capsid protein; residues 7127-7431 encode a portion of the Rep68 protein; residues 3984-4114 correspond to AAV2 P5 promoter sequences (SEQ ID NO:10); residues 4237-4253 are M13 Rev sequences; residues 4261-4277 are Lac operator sequences; 4285-4315 are Lac promoter sequences; residues 4578-5302 correspond to pMB ori sequences, residues 5398-6258 encode an ampicillin resistance determinant; and residues 6259-6357 are bla promoter sequences (FIG. 3).

2. Plasmid pAAV-RC2

Figure 4:
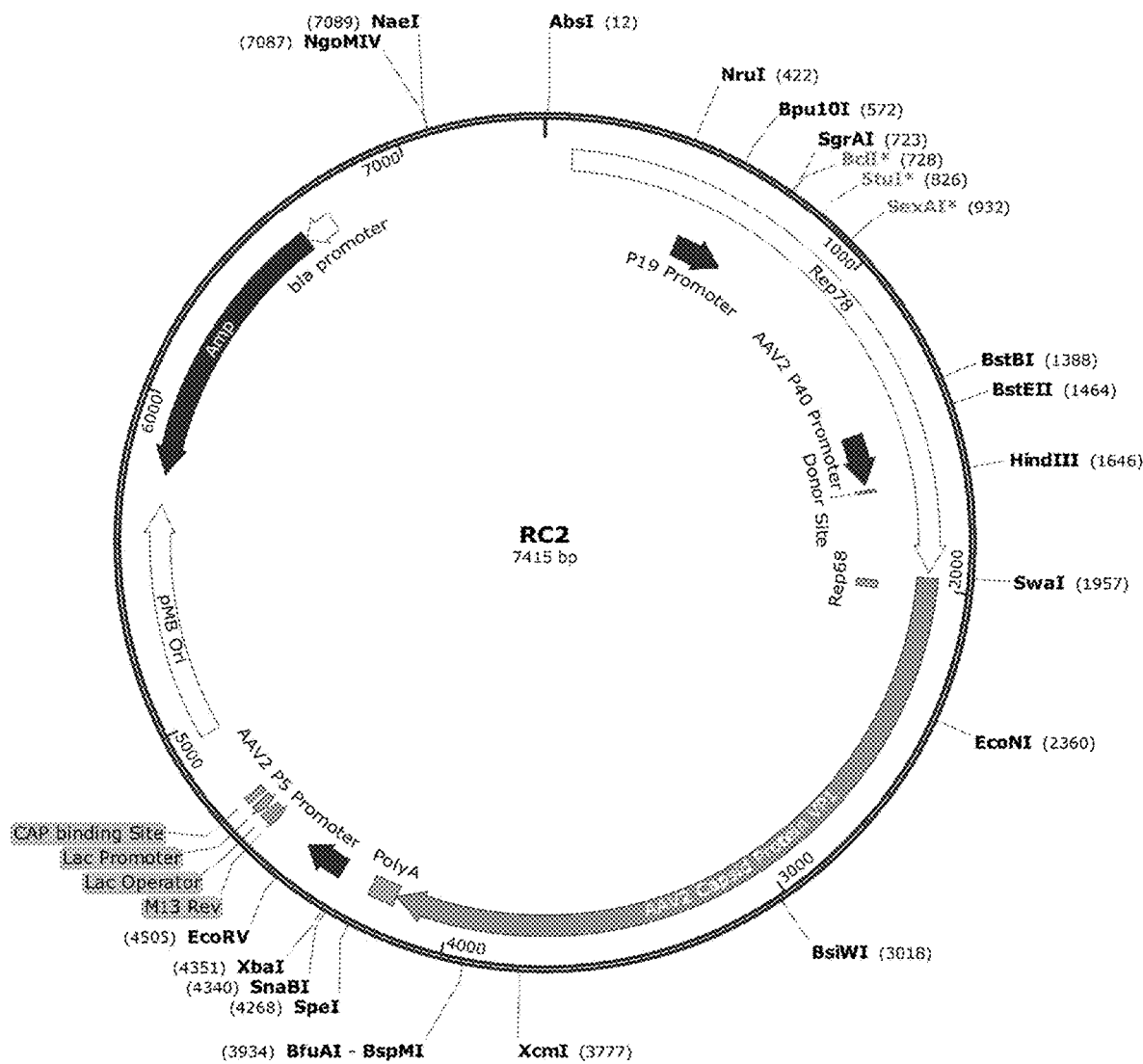
FIG. 4 shows a map of the AAV helper plasmid vector pAAV-RC2 (SEQ ID NO:2).

Plasmid pAAV-RC2 (SEQ ID NO:2; FIG. 4) is an AAV helper plasmid that expresses AAV2 serotype capsid proteins that may be used in accordance with the present invention to provide AAV helper functions. The P5 and P40 promoters of pAAV-RC2 are AAV2 serotype promoters (SEQ ID NO:10 and SEQ ID NO:18, respectively).

Coding Strand of Plasmid pAAV-RC2 (SEQ ID NO: 2):

```
ccgggccccc cctcgaggtc gacggtatcg ggggagctcg cagggtctcc
attttgaagc gggaggtttg aacgcgcagc cgccatgccg gggttttacg
agattgtgat taaggtcccc agcgaccttg acgagcatct gcccggcatt
tctgacagct ttgtgaactg ggtggccgag aaggaatggg agttgccgcc
agattctgac atggatctga atctgattga gcaggcaccc ctgaccgtgg
ccgagaagct gcagcgcgac tttctgacgg aatggcgccg tgtgagtaag
gccccggagg ctcttttctt tgtgcaattt gagaagggag agagctactt
ccacatgcac gtgctcgtgg aaaccaccgg ggtgaaatcc atggttttgg
gacgtttcct gagtcagatt cgcgaaaaac tgattcagag aatttaccgc
gggatcgagc cgactttgcc aaactggttc gcggtcacaa agaccagaaa
tggcgccgga ggcgggaaca aggtggtgga tgagtgctac atccccaatt
acttgctccc caaaacccag cctgagctcc agtgggcgtg gactaatatg
gaacagtatt taagcgcctg tttgaatctc acggagcgta acggttggt
ggcgcagcat ctgacgcacg tgtcgcagac gcaggagcag aacaaagaga
atcagaatcc caattctgat gcgccggtga tcagatcaaa aacttcagcc
aggtacatgg agctggtcgg gtggctcgtg gacaaggggga ttacctcgga
gaagcagtgg atccaggagg accaggcctc atacatctcc ttcaatgcgg
cctccaactc gcggtcccaa atcaaggctg ccttggacaa tgcgggaaag
attatgagcc tgactaaaac cgccccggac tacctggtgg gccagcagcc
cgtggaggac atttccagca atcggattta taaaatttg gaactaaacg
ggtacgatcc ccaatatgcg gcttccgtct ttctgggatg ggccacgaaa
aagttcggca agaggaacac catctggctg tttgggcctg caactaccgg
gaagaccaac atcgcggagg ccatagccca cactgtgccc ttctacgggt
gcgtaaactg gaccaatgag aactttccct caacgactg tgtcgacaag
atggtgatct ggtgggagga ggggaagatg accgccaagg tcgtggagtc
ggccaaagcc attctcggag gaagcaaggt gcgcgtggac cagaaatgca
agtcctcggc ccagatagac cgactcccg tgatcgtcac ctccaacacc
aacatgtgcg ccgtgattga cgggaactca acgaccttcg aacaccagca
gccgttgcaa gaccggatgt tcaaatttga actcaccccgc cgtctggatc
atgactttgg gaaggtcacc aagcaggaag tcaaagactt tttccggtgg
gcaaaggatc acgtggttga ggtggagcat gaattctacg tcaaaaaggg
tggagccaag aaaagacccg ccccagtga cgcagatata agtgagccca
aacggggtgcg cgagtcagtt gcgcagccat cgacgtcaga cgcggaagct
tcgatcaact acgcagacag gtaccaaaac aaatgttctc gtcacgtggg
catgaatctg atgctgtttc cctgcagaca atgcgagaga atgaatcaga
attcaaatat ctgcttcact cacggacaga aagactgttt agagtgcttt
cccgtgtcag aatctcaacc cgtttctgtc gtcaaaaagg cgtatcagaa
actgtgctac attcatcata tcatgggaaa ggtgccagac gcttgcactg
cctgcgatct ggtcaatgtg gatttggatg actgcatctt tgaacaataa
atgatttaaa tcaggtatgg ctgccgatgg ttatcttcca gattggctcg
```

-continued

```
aggacactct ctctgaagga ataagacagt ggtggaagct caaacctggc ccaccaccac caaagcccgc agagcggcat aaggacgaca gcaggggtct tgtgcttcct gggtacaagt acctcggacc cttcaacgga ctcgacaagg gagagccggt caacgaggca gacgccgcgg ccctcgagca cgacaaagcc tacgaccggc agctcgacag cggagacaac ccgtacctca agtacaacca cgccgacgcg gagtttcagg agcgccttaa agaagatacg tcttttgggg gcaacctcgg acgagcagtc ttccaggcga aaaagagggt tcttgaacct ctgggcctgg ttgaggaacc tgttaagacg gctccgggaa aaaagaggcc ggtagagcac tctcctgtgg agccagactc ctcctcggga accggaaagg cgggccagca gcctgcaaga aaaagattga attttggtca gactggagac gcagactcag tacctgaccc ccagcctctc ggacagccac cagcagcccc ctctggtctg ggaactaata cgatggctac aggcagtggc gcaccaatgg cagacaataa cgagggcgcc gacggagtgg gtaattcctc gggaaattgg cattgcgatt ccacatggat gggcgacaga gtcatcacca ccagcacccg aacctgggcc ctgcccacct acaacaacca cctctacaaa caaatttcca gccaatcagg agcctcgaac gacaatcact actttggcta cagcacccct tgggggtatt ttgacttcaa cagattccac tgccactttt caccacgtga ctggcaaaga ctcatcaaca caactgggg attccgaccc aagagactca acttcaagct ctttaacatt caagtcaaag aggtcacgca gaatgacggt acgacgacga ttgccaataa ccttaccagc acggttcagg tgtttactga ctcggagtac cagctcccgt acgtcctcgg ctcggcgcat caaggatgcc tcccgccgtt cccagcagac gtcttcatgg tgccacagta tggatacctc accctgaaca acgggagtca ggcagtagga cgctcttcat tttactgcct ggagtacttt ccttctcaga tgctgcgtac cggaaacaac tttaccttca gctacacttt tgaggacgtt cctttccaca gcagctacgc tcacagccag agtctggacc gtctcatgaa tcctctcatc gaccagtacc tgtattactt gagcagaaca aacactccaa gtggaaccac cacgcagtca aggcttcagt tttctcaggc cggagcgagt gacattcggg accagtctag gaactggctt cctggaccct gttaccgcca gcagcgagta tcaaagacat ctgcggataa caacaacagt gaatactcgt ggactggagc taccaagtac cacctcaatg gcagagactc tctggtgaat ccgggcccgg ccatggcaag ccacaaggac gatgaagaaa agttttttcc tcagagcggg gttctcatct ttgggaagca aggctcagag aaaacaaatg tggacattga aaaggtcatg attacagacg aagaggaaat caggacaacc aatcccgtgg ctacggagca gtatggttct gtatctacca acctccagag aggcaacaga caagcagcta ccgcagatgt caacacacaa ggcgttcttc caggcatggt ctggcaggac agagatgtgt accttcaggg gcccatctgg gcaaagattc cacacacgga cggacatttt caccccctctc ccctcatggg tggattcgga cttaaacacc ctcctccaca gattctcatc aagaacaccc cggtacctgc gaatccttcg accaccttca gtgcggcaaa gtttgcttcc ttcatcacac agtactccac gggacaggtc agcgtggaga tcgagtggga gctgcagaag gaaaacagca aacgctggaa
```

-continued

```
tcccgaaatt cagtacactt ccaactacaa caagtctgtt aatgtggact
ttactgtgga cactaatggc gtgtattcag agcctcgccc cattggcacc
agatacctga ctcgtaatct gtaattgctt gttaatcaat aaaccgttta
attcgtttca gttgaacttt ggtctctgcg tatttctttc ttatctagtt
tccatgctct aggatccact agtaacggcc gccagtgtgc tggaattcgg
ctttgtagtt aatgattaac ccgccatgct acttatctac gtagccatgc
tctagaggtc ctgtattaga ggtcacgtga gtgttttgcg acattttgcg
acaccatgtg gtcacgctgg gtatttaagc ccgagtgagc acgcagggtc
tccattttga agcgggaggt ttgaacgcgc agccgccaag ccgaattctg
cagatatcca aacactggcg gccgctcgac tagagcggcc gccaccgcgg
tggagctcca gcttttgttc cctttagtga gggttaattg cgcgcttggc
gtaatcatgg tcatagctgt ttcctgtgtg aaattgttat ccgctcacaa
ttccacacaa catacgagcc ggaagcataa agtgtaaagc ctggggtgcc
taatgagtga gctaactcac attaattgcg ttgcgctcac tgcccgcttt
ccagtcggga aacctgtcgt gccagctgca ttaatgaatc ggccaacgcg
cggggagagg cggtttgcgt attgggcgct cttccgcttc ctcgctcact
gactcgctgc gctcggtcgt tcggctgcgg cgagcggtat cagctcactc
aaaggcggta atacggttat ccacagaatc aggggataac gcaggaaaga
acatgtgagc aaaaggccag caaaaggcca ggaaccgtaa aaaggccgcg
ttgctggcgt ttttccatag gctccgcccc cctgacgagc atcacaaaaa
tcgacgctca agtcagaggt ggcgaaaccc gacaggacta taaagatacc
aggcgtttcc ccctggaagc tccctcgtgc gctctcctgt tccgaccctg
ccgcttaccg gatacctgtc cgcctttctc ccttcgggaa gcgtggcgct
ttctcatagc tcacgctgta ggtatctcag ttcggtgtag gtcgttcgct
ccaagctggg ctgtgtgcac gaaccccccg ttcagcccga ccgctgcgcc
ttatccggta actatcgtct tgagtccaac ccggtaagac acgacttatc
gccactggca gcagccactg gtaacaggat tagcagagcg aggtatgtag
gcggtgctac agagttcttg aagtggtggc ctaactacgg ctacactaga
agaacagtat ttggtatctg cgctctgctg aagccagtta ccttcggaaa
aagagttggt agctcttgat ccggcaaaca accaccgct ggtagcggtg
gttttttttgt ttgcaagcag cagattacgc gcagaaaaaa aggatctcaa
gaagatcctt tgatcttttc tacggggtct gacgctcagt ggaacgaaaa
ctcacgttaa gggattttgg tcatgagatt atcaaaaagg atcttcacct
agatcctttt aaattaaaaa tgaagtttta aatcaatcta agtatatat
gagtaaactt ggtctgacag ttaccaatgc ttaatcagtg aggcacctat
ctcagcgatc tgtctatttc gttcatccat agttgcctga ctccccgtcg
tgtagataac tacgatacgg gagggcttac catctggccc cagtgctgca
atgataccgc gagacccacg ctcaccggct ccagatttat cagcaataaa
ccagccagcc ggaagggccg agcgcagaag tggtcctgca actttatccg
cctccatcca gtctattaat tgttgccggg aagctagagt aagtagttcg
```

-continued

```
ccagttaata gtttgcgcaa cgttgttgcc attgctacag gcatcgtggt gtcacgctcg tcgtttggta tggcttcatt cagctccggt tcccaacgat caaggcgagt tacatgatcc cccatgttgt gcaaaaaagc ggttagctcc ttcggtcctc cgatcgttgt cagaagtaag ttggccgcag tgttatcact catggttatg gcagcactgc ataattctct tactgtcatg ccatccgtaa gatgcttttc tgtgactggt gagtactcaa ccaagtcatt ctgagaatag tgtatgcggc gaccgagttg ctcttgcccg gcgtcaatac gggataatac cgcgccacat agcagaactt taaaagtgct catcattgga aaacgttctt cggggcgaaa actctcaagg atcttaccgc tgttgagatc cagttcgatg taacccactc gtgcacccaa ctgatcttca gcatctttta ctttcaccag cgtttctggg tgagcaaaaa caggaaggca aaatgccgca aaaaagggaa taagggcgac acgaaatgt tgaatactca tactcttcct ttttcaatat tattgaagca tttatcaggg ttattgtctc atgagcggat acatatttga atgtatttag aaaaataaac aaataggggt tccgcgcaca tttccccgaa aagtgccacc taaattgtaa gcgttaatat tttgttaaaa ttcgcgttaa atttttgtta aatcagctca ttttttaacc aataggccga aatcggcaaa atcccttata aatcaaaaga atagaccgag atagggttga gtgttgttcc agtttggaac aagagtccac tattaaagaa cgtggactcc aacgtcaaag ggcgaaaaac cgtctatcag ggcgatggcc cactacgtga accatcaccc taatcaagtt ttttggggtc gaggtgccgt aaagcactaa atcggaaccc taaagggagc ccccgattta gagcttgacg gggaaagccg gcgaacgtgg cgagaaagga agggaagaaa gcgaaaggag cgggcgctag ggcgctggca agtgtagcgg tcacgctgcg cgtaaccacc acacccgccg cgcttaatgc gccgctacag ggcgcgtccc attcgccatt caggctgcgc aactgttggg aagggcgatc ggtgcgggcc tcttcgctat tacgccagct ggcgaaaggg ggatgtgctg caaggcgatt aagttgggta acgccagggt tttcccagtc acgacgttgt aaaacgacgg ccagtgagcg cgcgtaatac gactcactat agggcgaatt gggta
```

In SEQ ID NO:2, residues 85-1950 of pAAV-RC2 encode the Rep protein, Rep78 (with residues 484-663 corresponding to the AAV2 P19 promoter, residues 1464-1643 corresponding to the AAV2 P40 promoter (SEQ ID NO:18) and residues 1668-1676 being a donor site); residues 1967-4174 encode the AAV2 VP1 capsid protein; residues 1992-2016 encode a portion of the Rep68 protein; residues 4175-4256 encode a polyA sequence; residues 4357-4487 correspond to the AAV2 P5 promoter sequences of SEQ ID NO:10); residues 4610-4626 are M13 Rev sequences; residues 4634-4650 are Lac operator sequences; 4658-4688 are Lac promoter sequences; residues 4951-5675 correspond to pMB ori sequences, residues 5771-6631 encode an ampicillin resistance determinant; and residues 6632-6730 are bla promoter sequences (FIG. 4).

3. Plasmid pAAV-RC5

Figure 5:
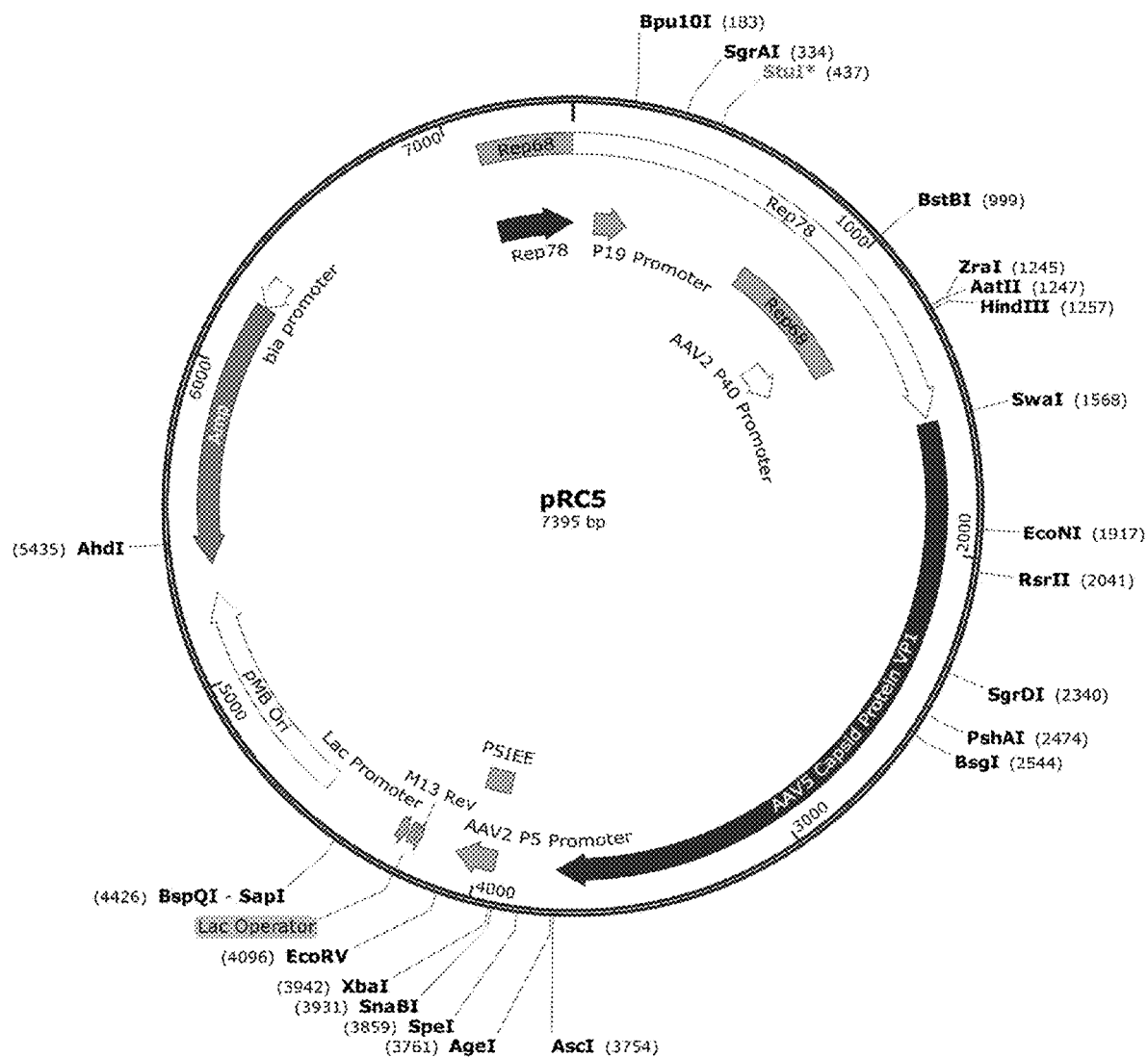
FIG. 5 shows a map of the AAV helper plasmid vector pAAV-RC5 (SEQ ID NO:3).

Plasmid pAAV-RC5 (SEQ ID NO:3; FIG. 5) is an AAV helper plasmid that expresses AAV5 serotype capsid proteins that may be used in accordance with the present invention to provide AAV helper functions. The P5 and P40 promoters of pAAV-RC5 are AAV2 serotype promoters (SEQ ID NO:10 and SEQ ID NO:18, respectively).

Coding Strand of Plasmid pAAV-RC5 (SEQ ID NO:3):

```
catggttttg ggacgtttcc tgagtcagat tcgcgaaaaa ctgattcaga
gaatttaccg cgggatcgag ccgactttgc caaactggtt cgcggtcaca
aagaccagaa atggcgccgg aggcgggaac aaggtggtgg atgagtgcta
catccccaat tacttgctcc ccaaaaccca gcctgagctc cagtgggcgt
ggactaatat ggaacagtat ttaagcgcct gtttgaatct cacggagcgt
aaacggttgg tggcgcagca tctgacgcac gtgtcgcaga cgcaggagca
gaacaaagag aatcagaatc ccaattctga tgcgccggtg atcagatcaa
aaacttcagc caggtacatg gagctggtcg ggtggctcgt ggacaagggg
attacctcgg agaagcagtg gatccaggag gaccaggcct catacatctc
cttcaatgcg gcctccaact cgcggtccca aatcaaggct gccttggaca
atgcgggaaa gattatgagc ctgactaaaa ccgccccga ctacctggtg
ggccagcagc ccgtggagga catttccagc aatcggattt ataaaatttt
ggaactaaac gggtacgatc cccaatatgc ggcttccgtc tttctgggat
gggccacgaa aaagttcggc aagaggaaca ccatctggct gtttgggcct
gcaactaccg ggaagaccaa catcgcggag ccatagccc acactgtgcc
cttctacggg tgcgtaaact ggaccaatga aactttccc ttcaacgact
gtgtcgacaa gatggtgatc tggtgggagg aggggaagat gaccgccaag
gtcgtggagt cggccaaagc cattctcgga ggaagcaagg tgcgcgtgga
ccagaaatgc aagtcctcgg cccagataga cccgactccc gtgatcgtca
cctccaacac caacatgtgc gccgtgattg acgggaactc aacgaccttc
gaacaccagc agccgttgca agaccggatg ttcaaatttg aactcacccg
ccgtctggat catgactttg gaaggtcac caagcaggaa gtcaaagact
ttttccggtg ggcaaaggat cacgtggttg aggtggagca tgaattctac
gtcaaaaagg gtggagccaa gaaaagaccc gcccccagtg acgcagatat
aagtgagccc aaacgggtgc gcgagtcagt tgcgcagcca tcgacgtcag
acgcggaagc ttcgatcaac tacgcagaca ggtaccaaaa caaatgttct
cgtcacgtgg gcatgaatct gatgctgttt ccctgcagac aatgcgagag
aatgaatcag aattcaaata tctgcttcac tcacggacag aaagactgtt
tagagtgctt tcccgtgtca gaatctcaac ccgtttctgt cgtcaaaaag
gcgtatcaga aactgtgcta cattcatcat atcatgggaa aggtgccaga
cgcttgcact gcctgcgatc tggtcaatgt ggatttggat gactgcatct
ttgaacaata aatgatttaa atcaggtatg tcttttgttg atcaccctcc
agattggttg gaagaagttg gtgaaggtct cgcgagtttt ttgggccttg
aagcgggccc accgaaacca aaacccaatc agcagcatca agatcaagcc
cgtggtcttg tgctgcctgg ttataactat ctcggacccg gaaacggtct
cgatcgagga gagcctgtca cagggcaga cgaggtcgcg cgagagcacg
acatctcgta caacgagcag cttgaggcgg gagacaaccc ctacctcaag
tacaaccacg cggacgccga gtttcaggag aagctcgccg acgacacatc
cttcgggggag aacctcggaa aggcagtctt tcaggccaag aaaagggttc
```

Coding Strand of Plasmid pAAV-RC5 (SEQ ID NO:3):

```
tcgaaccttt tggcctggtt gaagagggtg ctaagacggc ccctaccgga
aagcggatag acgaccactt tccaaaaaga aagaaggctc ggaccgaaga
ggactccaag ccttccacct cgtcagacgc cgaagctgga cccagcggat
cccagcagct gcaaatccca gcccaaccag cctcaagttt gggagctgat
acaatgtctg cgggaggtgg cggcccattg ggcgacaata accaaggtgc
cgatggagtg ggcaatgcct cgggagattg gcattgcgat tccacgtgga
tgggggacag agtcgtcacc aagtccaccc gaacctgggt gctgcccagc
tacaacaacc accagtaccg agagatcaaa agcggctccg tcgacggaag
caacgccaac gcctactttg gatacagcac ccctggggg tactttgact
ttaaccgctt ccacagccac tggagccccc gagactggca aagactcatc
aacaactact ggggcttcag accccggtcc ctcagagtca aaatcttcaa
cattcaagtc aaagaggtca cggtgcagga ctccaccacc accatcgcca
acaacctcac ctccaccgtc caagtgttta cggacgacga ctaccagctg
ccctacgtcg tcggcaacgg gaccgaggga tgcctgccgg ccttccctcc
gcaggtcttt acgctgccgc agtacggtta cgcgacgctg aaccgcgaca
acacagaaaa tcccaccgag aggagcagct tcttctgcct agagtacttt
cccagcaaga tgctgagaac gggcaacaac tttgagttta cctacaactt
tgaggaggtg cccttccact ccagcttcgc tcccagtcag aacctgttca
agctggccaa cccgctggtg gaccagtact tgtaccgctt cgtgagcaca
aataacactg gcggagtcca gttcaacaag aacctggccg ggagatacgc
caacacctac aaaaactggt tcccggggcc catgggccga acccagggct
ggaacctggg ctccggggtc aaccgcgcca gtgtcagcgc cttcgccacg
accaatagga tggagctcga gggcgcgagt taccaggtgc cccgcagcc
gaacggcatg accaacaacc tccagggcag caacacctat gccctggaga
acactatgat cttcaacagc cagccggcga acccgggcac caccgccacg
tacctcgagg gcaacatgct catcaccagc gagagcgaga cgcagccggt
gaaccgcgtg gcgtacaacg tcggcgggca gatggccacc aacaaccaga
gctccaccac tgcccccgcg accggcacgt acaacctcca ggaaatcgtg
cccggcagcg tgtggatgga gagggacgtg tacctccaag acccatctg
ggccaagatc ccagagacgg gggcgcactt tcaccctct ccggccatgg
gcggattcgg actcaaacac ccaccgccca tgatgctcat caagaacacg
cctgtgcccg gaaatatcac cagcttctcg gacgtgcccg tcagcagctt
catcacccag tacagcaccg ggcaggtcac cgtggagatg gagtgggagc
tcaagaagga aaactccaag aggtggaacc cagagatcca gtacacaaac
aactacaacg acccccagtt tgtggacttt gccccggaca gcaccgggga
atacagaacc accagaccta tcggaacccg ataccttacc gaccccttt
aaggcgcgcc accggttgct tgttaatcaa taaaccgttt aattcgtttc
agttgaactt tggtctctgc gtatttcttt cttatctagt ttccatgctc
```

Coding Strand of Plasmid pAAV-RC5 (SEQ ID NO:3):

```
taggatccac tagtaacggc cgccagtgtg ctggaattcg gctttgtagt
taatgattaa cccgccatgc tacttatcta cgtagccatg ctctagaggt
cctgtattag aggtcacgtg agtgttttgc gacattttgc gacaccatgt
ggtcacgctg ggtatttaag cccgagtgag cacgcagggt ctccattttg
aagcgggagg tttgaacgcg cagccgccaa gccgaattct gcagatatcc
aaacactggc ggccgctcga ctagagcggc cgccaccgcg gtggagctcc
agcttttgtt cccttagtg agggttaatt gcgcgcttgg cgtaatcatg
gtcatagctg tttcctgtgt gaaattgtta tccgctcaca attccacaca
acatacgagc cggaagcata aagtgtaaag cctggggtgc ctaatgagtg
agctaactca cattaattgc gttgcgctca ctgcccgctt tccagtcggg
aaacctgtcg tgccagctgc attaatgaat cggccaacgc gcgggagag
gcggtttgcg tattgggcgc tcttccgctt cctcgctcac tgactcgctg
cgctcggtcg ttcggctgcg gcgagcggta tcagctcact caaaggcggt
aatacggtta tccacagaat caggggataa cgcaggaaag aacatgtgag
caaaaggcca gcaaaggcc aggaaccgta aaaaggccgc gttgctggcg
ttttttccata ggctccgccc cctgacgag catcacaaa atcgacgctc
aagtcagagg tggcgaaacc cgacaggact ataaagatac caggcgtttc
cccctggaag ctccctcgtg cgctctcctg ttccgaccct gccgcttacc
ggatacctgt ccgcctttct cccttcggga agcgtggcgc tttctcatag
ctcacgctgt aggtatctca gttcggtgta ggtcgttcgc tccaagctgg
gctgtgtgca cgaaccccc gttcagcccg accgctgcgc cttatccggt
aactatcgtc ttgagtccaa cccggtaaga cacgacttat cgccactggc
agcagccact ggtaacagga ttagcagagc gaggtatgta ggcggtgcta
cagagttctt gaagtggtgg cctaactacg gctacactag aagaacagta
tttggtatct gcgctctgct gaagccagtt accttcggaa aaagagttgg
tagctcttga tccggcaaac aaaccaccgc tggtagcggt ggtttttttg
tttgcaagca gcagattacg cgcagaaaaa aaggatctca agaagatcct
ttgatctttt ctacggggtc tgacgctcag tggaacgaaa actcacgtta
agggattttg gtcatgagat tatcaaaaag gatcttcacc tagatccttt
taaattaaaa atgaagtttt aaatcaatct aaagtatata tgagtaaact
tggtctgaca gttaccaatg cttaatcagt gaggcaccta tctcagcgat
ctgtctattt cgttcatcca tagttgcctg actccccgtc gtgtagataa
ctacgatacg ggagggctta ccatctggcc ccagtgctgc aatgataccg
cgagacccac gctcaccggc tccagattta tcagcaataa accagccagc
cggaagggcc gagcgcagaa gtggtcctgc aactttatcc gcctccatcc
agtctattaa ttgttgccgg gaagctagag taagtagttc gccagttaat
agtttgcgca acgttgttgc cattgctaca ggcatcgtgg tgtcacgctc
gtcgtttggt atggcttcat tcagctccgg ttcccaacga tcaaggcgag
```

Coding Strand of Plasmid pAAV-RC5 (SEQ ID NO:3):

```
ttacatgatc ccccatgttg tgcaaaaaag cggttagctc cttcggtcct ccgatcgttg tcagaagtaa gttggccgca gtgttatcac tcatggttat ggcagcactg cataattctc ttactgtcat gccatccgta agatgctttt ctgtgactgg tgagtactca accaagtcat tctgagaata gtgtatgcgg cgaccgagtt gctcttgccc ggcgtcaata cgggataata ccgcgccaca tagcagaact ttaaaagtgc tcatcattgg aaaacgttct cggggcgaa aactctcaag gatcttaccg ctgttgagat ccagttcgat gtaacccact cgtgcaccca actgatcttc agcatctttt actttcacca gcgtttctgg gtgagcaaaa acaggaaggc aaaatgccgc aaaaaaggga taagggcga cacggaaatg ttgaatactc atactcttcc tttttcaata ttattgaagc atttatcagg gttattgtct catgagcgga tacatatttg aatgtattta gaaaaataaa caaatagggg ttccgcgcac atttccccga aaagtgccac ctaaattgta agcgttaata ttttgttaaa attcgcgtta aattttttgtt aaatcagctc atttttaac caataggccg aaatcggcaa aatcccttat aaatcaaaag aatagaccga gatagggttg agtgttgttc cagtttggaa caagagtcca ctattaaaga acgtggactc caacgtcaaa gggcgaaaaa ccgtctatca gggcgatggc ccactacgtg aaccatcacc ctaatcaagt tttttggggt cgaggtgccg taaagcacta atcggaacc ctaaagggag cccccgattt agagcttgac ggggaaagcc ggcgaacgtg gcgagaaagg aagggaagaa agcgaaagga cgggcgcta gggcgctggc aagtgtagcg gtcacgctgc gcgtaaccac cacacccgcc gcgcttaatg cgccgctaca gggcgcgtcc cattcgccat tcaggctgcg caactgttgg gaagggcgat cggtgcgggc ctcttcgcta ttacgccagc tggcgaaagg gggatgtgct gcaaggcgat taagttgggt aacgccaggg ttttcccagt cacgacgttg taaaacgacg gccagtgagc gcgcgtaata cgactcacta tagggcgaat tgggtaccgg gccccccctc gaggtcgacg gtatcggggg agctcgcagg gtctccattt tgaagcggga ggtttgaacg cgcagccgcc atgccggggt tttacgagat tgtgattaag gtccccagcg accttgacga gcatctgccc ggcatttctg acagctttgt gaactgggtg gccgagaagg aatgggagtt gccgccagat tctgacatgg atctgaatct gattgagcag gcacccctga ccgtggccga gaagctgcag cgcgactttc tgacggaatg gcgccgtgtg agtaaggccc cggaggctct tttctttgtg caatttgaga agggagagag ctacttccac atgcacgtgc tcgtggaaac caccgggtg aaatc
```

In SEQ ID NO:3, residues 1-1561 of pAAV-RC5 encode the Rep protein, Rep78 (with residues 91-221 corresponding to the AAV2 P19 promoter, and residues 1075-1254 corresponding to the P40 promoter (SEQ ID NO:18)); residues 1578-3749 encode the AAV5 VP1 capsid protein; residues 7091-7395 encode a portion of the Rep68 protein; residues 3948-4078 correspond to the AAV2 P5 promoter sequences of SEQ ID NO:10); residues 4201-4217 are M13 Rev sequences; residues 4225-4241 are Lac operator sequences; 4249-4279 are Lac promoter sequences; residues 4542-5266 correspond to pMB ori sequences, residues 5362-6222 encode an ampicillin resistance determinant; and residues 6223-6321 are bla promoter sequences (FIG. 5).

4. Plasmid pAAV-RC6

Figure 6:
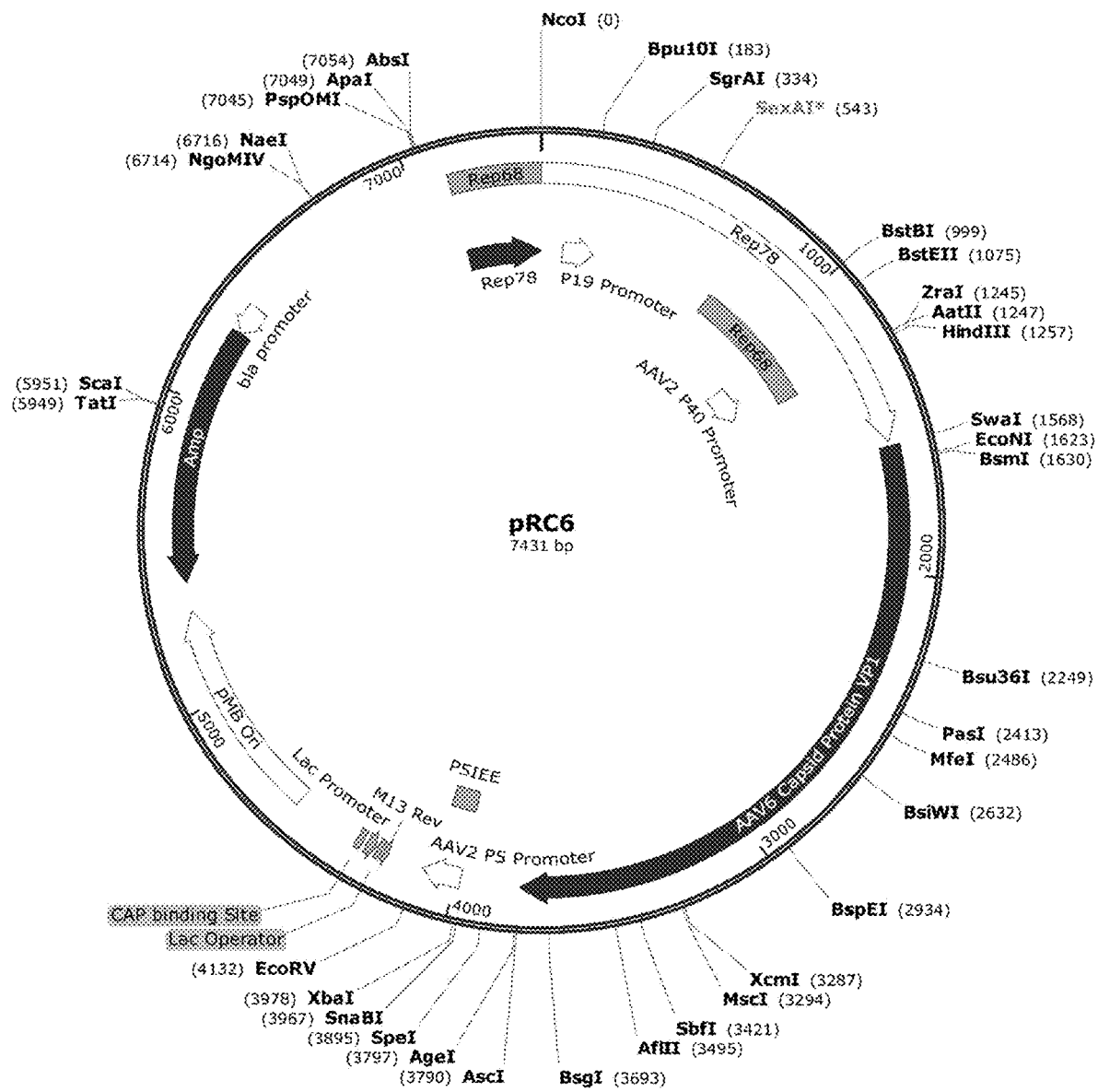
FIG. 6 shows a map of the AAV helper plasmid vector pAAV-RC6 (SEQ ID NO:4).

Plasmid pAAV-RC6 (SEQ ID NO:4; FIG. 6) is an AAV helper plasmid that expresses AAV6 serotype capsid proteins that may be used in accordance with the present invention to provide AAV helper functions. The P5 and P40 promoters of pAAV-RC6 are AAV2 serotype promoters (SEQ ID NO:10 and SEQ ID NO:18, respectively).

Coding Strand of Plasmid pAAV-RC6 (SEQ ID NO:4):

```
catggttttg ggacgtttcc tgagtcagat tcgcgaaaaa ctgattcaga
gaatttaccg cgggatcgag ccgactttgc caaactggtt cgcggtcaca
aagaccagaa atggcgccgg aggcgggaac aaggtggtgg atgagtgcta
catccccaat tacttgctcc ccaaaaccca gcctgagctc cagtgggcgt
ggactaatat ggaacagtat ttaagcgcct gtttgaatct cacggagcgt
aaacggttgg tggcgcagca tctgacgcac gtgtcgcaga cgcaggagca
gaacaaagag aatcagaatc ccaattctga tgcgccggtg atcagatcaa
aaacttcagc caggtacatg gagctggtcg ggtggctcgt ggacaagggg
attacctcgg agaagcagtg gatccaggag gaccaggcct catacatctc
cttcaatgcg gcctccaact cgcggtccca aatcaaggct gccttggaca
atgcgggaaa gattatgagc ctgactaaaa ccgccccga ctacctggtg
ggccagcagc ccgtggagga catttccagc aatcggattt ataaaatttt
ggaactaaac gggtacgatc cccaatatgc ggcttccgtc tttctgggat
gggccacgaa aaagttcggc aagaggaaca ccatctggct gtttgggcct
gcaactaccg ggaagaccaa catcgcggag gccatagccc acactgtgcc
cttctacggg tgcgtaaact ggaccaatga aactttccc ttcaacgact
gtgtcgacaa gatggtgatc tggtgggagg aggggaagat gaccgccaag
gtcgtggagt cggccaaagc cattctcgga ggaagcaagg tgcgcgtgga
ccagaaatgc aagtcctcgg cccagataga cccgactccc gtgatcgtca
cctccaacac caacatgtgc gccgtgattg acgggaactc aacgaccttc
gaacaccagc agccgttgca agaccggatg ttcaaatttg aactcacccg
ccgtctggat catgactttg gaaggtcac caagcaggaa gtcaaagact
ttttccggtg ggcaaaggat cacgtggttg aggtggagca tgaattctac
gtcaaaaagg gtggagccaa gaaaagaccc gcccccagtg acgcagatat
aagtgagccc aaacgggtgc gcgagtcagt tgcgcagcca tcgacgtcag
acgcggaagc ttcgatcaac tacgcagaca ggtaccaaaa caaatgttct
cgtcacgtgg gcatgaatct gatgctgttt ccctgcagac aatgcgagag
aatgaatcag aattcaaata tctgcttcac tcacggacag aaagactgtt
tagagtgctt tcccgtgtca gaatctcaac ccgtttctgt cgtcaaaaag
gcgtatcaga aactgtgcta cattcatcat atcatgggaa aggtgccaga
cgcttgcact gcctgcgatc tggtcaatgt ggatttggat gactgcatct
ttgaacaata aatgatttaa atcaggtatg gctgccgatg gttatcttcc
agattggctc gaggacaacc tctctgaggg cattcgcgag tggtgggact
tgaaacctgg agccccgaaa cccaaagcca accagcaaaa gcaggacgac
ggccgggtc tggtgcttcc tggctacaag tacctcggac ccttcaacgg
actcgacaag ggggagcccg tcaacgcggc ggatgcagcg gccctcgagc
acgacaaggc ctacgaccag cagctcaaag cgggtgacaa tccgtacctg
cggtataacc acgccgacgc cgagtttcag gagcgtctgc aagaagatac
gtcttttggg ggcaacctcg gcgagcagt cttccaggcc aagaagaggg
ttctcgaacc ttttggtctg gttgaggaag gtgctaagac ggctcctgga
```

Coding Strand of Plasmid pAAV-RC6 (SEQ ID NO:4):

```
aagaaacgtc cggtagagca gtcgccacaa gagccagact cctcctcggg
cattggcaag acaggccagc agcccgctaa aaagagactc aattttggtc
agactggcga ctcagagtca gtccccgacc cacaacctct cggagaacct
ccagcaaccc ccgctgctgt gggacctact acaatggctt caggcggtgg
cgcaccaatg cagacaata acgaaggcgc cgacggagtg ggtaatgcct
caggaaattg gcattgcgat tccacatggc tgggcgacag agtcatcacc
accagcaccc gaacatgggc cttgcccacc tataacaacc acctctacaa
gcaaatctcc agtgcttcaa cggggccag caacgacaac cactacttcg
gctacagcac cccctggggg tattttgatt tcaacagatt ccactgccat
ttctcaccac gtgactggca gcgactcatc aacaacaatt ggggattccg
gcccaagaga ctcaacttca agctcttcaa catccaagtc aaggaggtca
cgacgaatga tggcgtcacg accatcgcta ataaccttac cagcacggtt
caagtcttct cggactcgga gtaccagttg ccgtacgtcc tcggctctgc
gcaccagggc tgcctccctc cgttccggc ggacgtgttc atgattccgc
agtacggcta cctaacgctc aacaatggca gccaggcagt gggacggtca
tccttttact gcctggaata tttcccatcg cagatgctga gaacgggcaa
taactttacc ttcagctaca ccttcgagga cgtgcctttc cacagcagct
acgcgcacag ccagagcctg gaccggctga tgaatcctct catcgaccag
tacctgtatt acctgaacag aactcagaat cagtccggaa gtgcccaaaa
caaggacttg ctgtttagcc gggggtctcc agctggcatg tctgttcagc
ccaaaaactg gctacctgga ccctgttacc ggcagcagcg cgtttctaaa
acaaaaacag acaacaacaa cagcaacttt acctggactg gtgcttcaaa
atataacctt aatgggcgtg aatctataat caaccctggc actgctatgg
cctcacacaa agacgacaaa gacaagttct ttcccatgag cggtgtcatg
attttttggaa aggagagcgc cggagcttca aacactgcat tggacaatgt
catgatcaca gacgaagagg aaatcaaagc cactaacccc gtggccaccg
aaagatttgg gactgtggca gtcaatctcc agagcagcag cacagaccct
gcgaccggag atgtgcatgt tatgggagcc ttacctggaa tggtgtggca
agacagagac gtatacctgc agggtcctat ttgggccaaa attcctcaca
cggatggaca ctttcacccg tctcctctca tgggcggctt tggacttaag
caccgcctc ctcagatcct catcaaaaac acgcctgttc ctgcgaatcc
tccggcagag ttttcggcta caaagtttgc ttcattcatc acccagtatt
ccacaggaca agtgagcgtg gagattgaat gggagctgca gaaagaaaac
agcaaacgct ggaatcccga agtgcagtat acatctaact atgcaaaatc
tgccaacgtt gatttcactg tggacaacaa tggactttat actgagcctc
gccccattgg caccgttac ctcacccgtc cctgtaagg cgcgccaccg
gttgcttgtt aatcaataaa ccgtttaatt cgtttcagtt gaactttggt
ctctgcgtat ttctttctta tctagtttcc atgctctagg atccactagt
```

Coding Strand of Plasmid pAAV-RC6 (SEQ ID NO:4):

```
aacggccgcc agtgtgctgg aattcggctt tgtagttaat gattaacccg
ccatgctact tatctacgta gccatgctct agaggtcctg tattagaggt
cacgtgagtg ttttgcgaca ttttgcgaca ccatgtggtc acgctgggta
tttaagcccg agtgagcacg cagggtctcc attttgaagc gggaggtttg
aacgcgcagc cgccaagccg aattctgcag atatccaaac actggcggcc
gctcgactag agcggccgcc accgcggtgg agctccagct tttgttccct
ttagtgaggg ttaattgcgc gcttggcgta atcatggtca tagctgtttc
ctgtgtgaaa ttgttatccg ctcacaattc cacacaacat acgagccgga
agcataaagt gtaaagcctg gggtgcctaa tgagtgagct aactcacatt
aattgcgttg cgctcactgc ccgctttcca gtcgggaaac ctgtcgtgcc
agctgcatta atgaatcggc caacgcgcgg ggagaggcgg tttgcgtatt
gggcgctctt ccgcttcctc gctcactgac tcgctgcgct cggtcgttcg
gctgcggcga gcggtatcag ctcactcaaa ggcggtaata cggttatcca
cagaatcagg ggataacgca ggaaagaaca tgtgagcaaa aggccagcaa
aaggccagga accgtaaaaa ggccgcgttg ctggcgtttt tccataggct
ccgcccccct gacgagcatc acaaaaatcg acgctcaagt cagaggtggc
gaaacccgac aggactataa agataccagg cgtttccccc tggaagctcc
ctcgtgcgct ctcctgttcc gaccctgccg cttaccggat acctgtccgc
cttctccct tcgggaagcg tggcgctttc tcatagctca cgctgtaggt
atctcagttc ggtgtaggtc gttcgctcca agctgggctg tgtgcacgaa
ccccccgttc agcccgaccg ctgcgcctta tccggtaact atcgtcttga
gtccaacccg gtaagacacg acttatcgcc actggcagca gccactggta
acaggattag cagagcgagg tatgtaggcg gtgctacaga gttcttgaag
tggtggccta actacggcta cactagaaga acagtatttg gtatctgcgc
tctgctgaag ccagttacct tcggaaaaag agttggtagc tcttgatccg
gcaaacaaac caccgctggt agcggtggtt tttttgtttg caagcagcag
attacgcgca gaaaaaaagg atctcaagaa gatcctttga tcttttctac
ggggtctgac gctcagtgga acgaaaactc acgttaaggg attttggtca
tgagattatc aaaaaggatc ttcacctaga tccttttaaa ttaaaaatga
agttttaaat caatctaaag tatatatgag taaacttggt ctgacagtta
ccaatgctta atcagtgagg cacctatctc agcgatctgt ctatttcgtt
catccatagt tgcctgactc cccgtcgtgt agataactac gatacgggag
ggcttaccat ctggccccag tgctgcaatg ataccgcgag acccacgctc
accggctcca gatttatcag caataaacca gccagccgga agggccgagc
gcagaagtgg tcctgcaact ttatccgcct ccatccagtc tattaattgt
tgccgggaag ctagagtaag tagttcgcca gttaatagtt tgcgcaacgt
tgttgccatt gctacaggca tcgtggtgtc acgctcgtcg tttggtatgg
cttcattcag ctccggttcc caacgatcaa ggcgagttac atgatccccc
atgttgtgca aaaaagcggt tagctccttc ggtcctccga tcgttgtcag
```

Coding Strand of Plasmid pAAV-RC6 (SEQ ID NO:4):

```
aagtaagttg gccgcagtgt tatcactcat ggttatggca gcactgcata
attctcttac tgtcatgcca tccgtaagat gcttttctgt gactggtgag
tactcaacca agtcattctg agaatagtgt atgcggcgac cgagttgctc
ttgcccggcg tcaatacggg ataataccgc gccacatagc agaactttaa
aagtgctcat cattggaaaa cgttcttcgg ggcgaaaact ctcaaggatc
ttaccgctgt tgagatccag ttcgatgtaa cccactcgtg cacccaactg
atcttcagca tcttttactt tcaccagcgt ttctgggtga gcaaaaacag
gaaggcaaaa tgccgcaaaa aagggaataa gggcgacacg gaaatgttga
atactcatac tcttcctttt tcaatattat tgaagcattt atcagggtta
ttgtctcatg agcggataca tatttgaatg tatttagaaa aataaacaaa
tagggttcc gcgcacattt ccccgaaaag tgccacctaa attgtaagcg
ttaatatttt gttaaaattc gcgttaaatt tttgttaaat cagctcattt
tttaaccaat aggccgaaat cggcaaaatc ccttataaat caaaagaata
gaccgagata gggttgagtg ttgttccagt ttggaacaag agtccactat
taaagaacgt ggactccaac gtcaaaggc gaaaaaccgt ctatcagggc
gatggcccac tacgtgaacc atcaccctaa tcaagttttt tggggtcgag
gtgccgtaaa gcactaaatc ggaaccctaa agggagcccc cgatttagag
cttgacgggg aaagccggcg aacgtggcga gaaaggaagg gaagaaagcg
aaaggagcgg gcgctagggc gctggcaagt gtagcggtca cgctgcgcgt
aaccaccaca cccgccgcgc ttaatgcgcc gctacagggc gcgtcccatt
cgccattcag gctgcgcaac tgttgggaag ggcgatcggt gcgggcctct
tcgctattac gccagctggc gaaaggggga tgtgctgcaa ggcgattaag
ttgggtaacg ccagggtttt cccagtcacg acgttgtaaa acgacggcca
gtgagcgcgc gtaatacgac tcactatagg gcgaattggg taccgggccc
cccctcgagg tcgacggtat cggggggagct cgcagggtct ccattttgaa
gcgggaggtt tgaacgcgca gccgccatgc cggggtttta cgagattgtg
attaaggtcc ccagcgacct tgacgagcat ctgcccggca tttctgacag
ctttgtgaac tgggtggccg agaaggaatg ggagttgccg ccagattctg
acatggatct gaatctgatt gagcaggcac ccctgaccgt ggccgagaag
ctgcagcgcg actttctgac ggaatggcgc cgtgtgagta aggccccgga
ggctcttttc tttgtgcaat tgagaaggg agagagctac ttccacatgc
acgtgctcgt ggaaaccacc ggggtgcaaat c
```

In SEQ ID NO:4, residues 1-1561 of pAAV-RC6 encode the Rep protein, Rep78 (with residues 91-221 corresponding to the AAV2 P19 promoter, and residues 1075-1254 corresponding to the P40 promoter (SEQ ID NO:18)); residues 1578-3788 encode the AAV6 VP1 capsid protein; residues 736-1281 encode a portion of the Rep68 protein; residues 3984-4114 correspond to the AAV2 P5 promoter sequences of SEQ ID NO:10); residues 4237-4253 are M13 Rev sequences; residues 4261-4277 are Lac operator sequences; 4285-4315 are Lac promoter sequences; residues 4578-5302 correspond to pMB ori sequences, residues 5398-6258 encode an ampicillin resistance determinant; and residues 6259-6357 are bla promoter sequences (FIG. 6).

5. Plasmid pAAV-RC7

Figure 7:
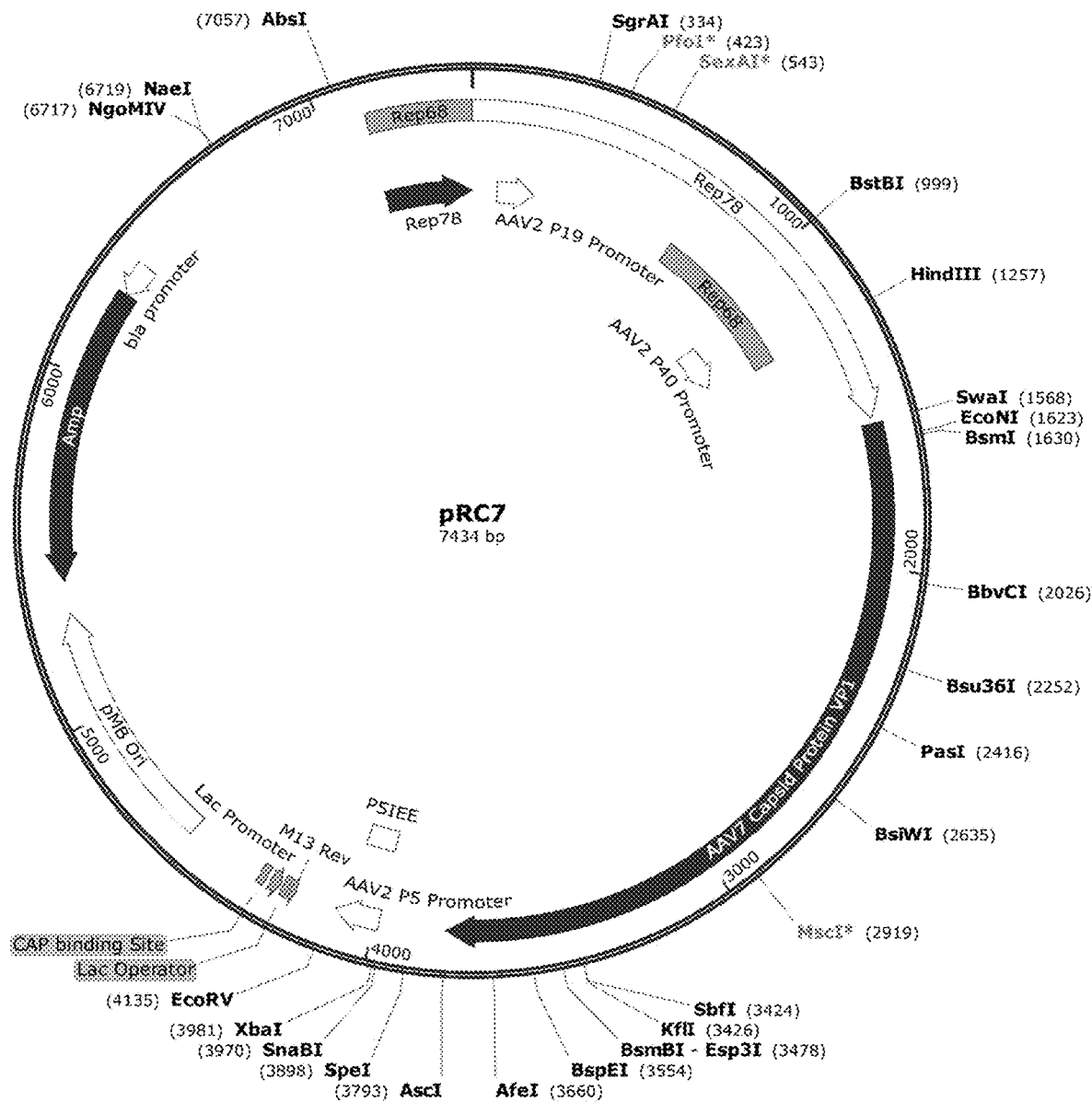
FIG. 7 shows a map of the AAV helper plasmid vector pAAV-RC7 (SEQ ID NO:5).

Plasmid pAAV-RC7 (SEQ ID NO:5; FIG. 7) is an AAV helper plasmid that expresses AAV6 serotype capsid proteins that may be used in accordance with the present invention to provide AAV helper functions. The P5 and P40 promoters of pAAV-RC7 are AAV2 serotype promoters (SEQ ID NO:10 and SEQ ID NO:18, respectively).

Coding Strand of Plasmid pAAV-RC7 (SEQ ID NO:5):

```
catggttttg ggacgtttcc tgagtcagat tcgcgaaaaa ctgattcaga
gaatttaccg cgggatcgag ccgactttgc caaactggtt cgcggtcaca
aagaccagaa atggcgccgg aggcgggaac aaggtggtgg atgagtgcta
catccccaat tacttgctcc ccaaaaccca gcctgagctc cagtgggcgt
ggactaatat ggaacagtat ttaagcgcct gtttgaatct cacggagcgt
aaacggttgg tggcgcagca tctgacgcac gtgtcgcaga cgcaggagca
gaacaaagag aatcagaatc ccaattctga tgcgccggtg atcagatcaa
aaacttcagc caggtacatg gagctggtcg ggtggctcgt ggacaagggg
attacctcgg agaagcagtg gatccaggag gaccaggcct catacatctc
cttcaatgcg gcctccaact cgcggtccca aatcaaggct gccttggaca
atgcgggaaa gattatgagc ctgactaaaa ccgcccccga ctacctggtg
ggccagcagc ccgtggagga catttccagc aatcggattt ataaaatttt
ggaactaaac gggtacgatc cccaatatgc ggcttccgtc tttctgggat
gggccacgaa aaagttcggc aagaggaaca ccatctggct gtttgggcct
gcaactaccg ggaagaccaa catcgcggag gccatagccc acactgtgcc
cttctacggg tgcgtaaact ggaccaatga aactttccc ttcaacgact
gtgtcgacaa gatggtgatc tggtgggagg aggggaagat gaccgccaag
gtcgtggagt cggccaaagc cattctcgga ggaagcaagg tgcgcgtgga
ccagaaatgc aagtcctcgg cccagataga cccgactccc gtgatcgtca
cctccaacac caacatgtgc gccgtgattg acgggaactc aacgaccttc
gaacaccagc agccgttgca agaccggatg ttcaaatttg aactcacccg
ccgtctggat catgactttg gaaggtcac caagcaggaa gtcaaagact
ttttccggtg ggcaaaggat cacgtggttg aggtggagca tgaattctac
gtcaaaaagg gtggagccaa gaaaagaccc gcccccagtg acgcagatat
aagtgagccc aaacgggtgc gcgagtcagt tgcgcagcca tcgacgtcag
acgcggaagc ttcgatcaac tacgcagaca ggtaccaaaa caaatgttct
cgtcacgtgg gcatgaatct gatgctgttt ccctgcagac aatgcgagag
aatgaatcag aattcaaata tctgcttcac tcacggacag aaagactgtt
tagagtgctt tcccgtgtca gaatctcaac ccgtttctgt cgtcaaaaag
gcgtatcaga aactgtgcta cattcatcat atcatgggaa aggtgccaga
cgcttgcact gcctgcgatc tggtcaatgt ggatttggat gactgcatct
ttgaacaata aatgatttaa atcaggtatg gctgccgatg gttatcttcc
agattggctc gaggacaacc tctctgaggg cattcgcgag tggtgggacc
tgaaacctgg agccccgaaa cccaaagcca accagcaaaa gcaggacaac
ggccgggtc tggtgcttcc tggctacaag tacctcggac ccttcaacgg
actcgacaag ggggagcccg tcaacgcggc ggacgcagcg gccctcgagc
acgacaaggc ctacgaccag cagctcaaag cgggtgacaa tccgtacctg
cggtataacc acgccgacgc cgagtttcag gagcgtctgc aagaagatac
gtcatttggg ggcaacctcg ggcgagcagt cttccaggcc aagaagcggg
ttctcgaacc tctcggtctg gttgaggaag cgctaagac ggctcctgca
```

Coding Strand of Plasmid pAAV-RC7 (SEQ ID NO:5):

aagaagagac cggtagagcc gtcacctcag cgttcccccg actcctccac gggcatcggc aagaaaggcc agcagcccgc cagaaagaga ctcaatttcg gtcagactgg cgactcagag tcagtccccg accctcaacc tctcggagaa cctccagcag cgccctctag tgtgggatct ggtacagtgg ctgcaggcgg tggcgcacca atggcagaca ataacgaagg tgccgacgga gtgggtaatg cctcaggaaa ttggcattgc gattccacat ggctgggcga cagagtcatt accaccagca cccgaacctg ggccctgccc acctacaaca accacctcta caagcaaatc tccagtgaaa ctgcaggtag taccaacgac aacacctact tcggctacag cacccctgg gggtattttg actttaacag attccactgc cacttctcac cacgtgactg gcagcgactc atcaacaaca actggggatt ccggcccaag aagctgcggt tcaagctctt caacatccag gtcaaggagg tcacgacgaa tgacggcgtt acgaccatcg ctaataacct taccagcacg attcaggtat tctcggactc ggaataccag ctgccgtacg tcctcggctc tgcgcaccag ggctgcctgc ctccgttccc ggcggacgtc ttcatgattc ctcagtacgg ctacctgact ctcaacaatg gcagtcagtc tgtgggacgt tcctccttct actgcctgga gtacttcccc tctcagatgc tgagaacggg caacaacttt gagttcagct acagcttcga ggacgtgcct ttccacagca gctacgcaca cagccagagc ctggaccggc tgatgaatcc cctcatcgac cagtacttgt actacctggc cagaacacag agtaacccag gaggcacagc tggcaatcgg gaactgcagt tttaccaggg cgggccttca actatggccg aacaagccaa gaattggtta cctggaccct gcttccggca caaagagtc tccaaaacgc tggatcaaaa caacaacagc aactttgctt ggactggtgc caccaaatat cacctgaacg gcagaaactc gttggttaat cccggcgtcg ccatggcaac tcacaaggac gacgaggacc gcttttccc atccagcgga gtcctgattt ttggaaaaac tggagcaact aacaaaacta cattggaaaa tgtgttaatg acaaatgaag aagaaattcg tcctactaat cctgtagcca cggaagaata cgggatagtc agcagcaact acaagcggc taatactgca gcccagacac aagttgtcaa caaccaggga gccttacctg catggtctg gcagaaccgg gacgtgtacc tgcagggtcc catctgggcc aagattcctc acacggatgg caactttcac ccgtctcctt tgatgggcgg ctttggactt aaacatccgc ctcctcagat cctgatcaag aacactcccg ttcccgctaa tcctccggag gtgtttactc tgccaagtt tgcttcgttc atcacacagt acagcaccgg acaagtcagc gtggaaatcg agtgggagct gcagaaggaa aacagcaagc gctggaaccc ggagattcag tacacctcca ctttgaaaa gcagactggt gtggactttg ccgttgacag ccagggtgtt tactctgagc ctcgccctat tggcactcgt tacctcaccc gtaatctgta aggcgcgcca ccggttgctt gttaatcaat aaaccgttta attcgtttca gttgaacttt ggtctctgcg tatttctttc ttatctagtt tccatgctct aggatccact

| Coding Strand of Plasmid pAAV-RC7 (SEQ ID NO:5): |
| --- |
| agtaacggcc gccagtgtgc tggaattcgg cttttgtagtt aatgattaac |
| ccgccatgct acttatctac gtagccatgc tctagaggtc ctgtattaga |
| ggtcacgtga gtgttttgcg acattttgcg acaccatgtg gtcacgctgg |
| gtatttaagc ccgagtgagc acgcagggtc tccatttga agcgggaggt |
| ttgaacgcgc agccgccaag ccgaattctg cagatatcca aacactggcg |
| gccgctcgac tagagcggcc gccaccgcgg tggagctcca gcttttgttc |
| cctttagtga gggttaattg cgcgcttggc gtaatcatgg tcatagctgt |
| ttcctgtgtg aaattgttat ccgctcacaa ttccacacaa catacgagcc |
| ggaagcataa agtgtaaagc ctggggtgcc taatgagtga gctaactcac |
| attaattgcg ttgcgctcac tgcccgcttt ccagtcggga acctgtcgt |
| gccagctgca ttaatgaatc ggccaacgcg cggggagagg cggtttgcgt |
| attgggcgct cttccgcttc ctcgctcact gactcgctgc gctcggtcgt |
| tcggctgcgg cgagcggtat cagctcactc aaaggcggta atacggttat |
| ccacagaatc agggataac gcaggaaaga acatgtgagc aaaaggccag |
| caaaaggcca ggaaccgtaa aaaggccgcg ttgctggcgt ttttccatag |
| gctccgcccc cctgacgagc atcacaaaaa tcgacgctca agtcagaggt |
| ggcgaaaccc gacaggacta taaagatacc aggcgtttcc ccctggaagc |
| tccctcgtgc gctctcctgt tccgaccctg ccgcttaccg gatacctgtc |
| cgcctttctc ccttcgggaa gcgtggcgct ttctcatagc tcacgctgta |
| ggtatctcag ttcggtgtag tcgttcgct ccaagctggg ctgtgtgcac |
| gaaccccccg ttcagcccga ccgctgcgcc ttatccggta actatcgtct |
| tgagtccaac ccggtaagac acgacttatc gccactggca gcagccactg |
| gtaacaggat tagcagagcg aggtatgtag gcggtgctac agagttcttg |
| aagtggtggc ctaactacgg ctacactaga agaacagtat ttggtatctg |
| cgctctgctg aagccagtta ccttcggaaa aagagttggt agctcttgat |
| ccggcaaaca aaccaccgct ggtagcggtg ttttttttgt ttgcaagcag |
| cagattacgc gcagaaaaaa aggatctcaa gaagatcctt tgatcttttc |
| tacggggtct gacgctcagt ggaacgaaaa ctcacgttaa gggattttgg |
| tcatgagatt atcaaaaagg atcttcacct agatcctttt aaattaaaaa |
| tgaagttta aatcaatcta agtatatat gagtaaactt ggtctgacag |
| ttaccaatgc ttaatcagtg aggcacctat ctcagcgatc tgtctatttc |
| gttcatccat agttgcctga ctccccgtcg tgtagataac tacgatacgg |
| gagggcttac catctggccc cagtgctgca atgataccgc gagacccacg |
| ctcaccggct ccagatttat cagcaataaa ccagccagcc ggaagggccg |
| agcgcagaag tggtcctgca actttatccg cctccatcca gtctattaat |
| tgttgccggg aagctagagt aagtagttcg ccagttaata gtttgcgcaa |
| cgttgttgcc attgctacag gcatcgtggt gtcacgctcg tcgtttggta |
| tggcttcatt cagctccggt tcccaacgat caaggcgagt tacatgatcc |
| cccatgttgt gcaaaaaagc ggttagctcc ttcggtcctc cgatcgttgt |

Coding Strand of Plasmid pAAV-RC7 (SEQ ID NO:5):

```
cagaagtaag ttggccgcag tgttatcact catggttatg gcagcactgc ataattctct tactgtcatg ccatccgtaa gatgctttc tgtgactggt gagtactcaa ccaagtcatt ctgagaatag tgtatgcggc gaccgagttg ctcttgcccg gcgtcaatac gggataatac cgcgccacat agcagaactt taaaagtgct catcattgga aaacgttctt cggggcgaaa actctcaagg atcttaccgc tgttgagatc cagttcgatg taacccactc gtgcacccaa ctgatcttca gcatctttta ctttcaccag cgtttctggg tgagcaaaaa caggaaggca aaatgccgca aaaagggaa taagggcgac acggaaatgt tgaatactca tactcttcct ttttcaatat tattgaagca tttatcaggg ttattgtctc atgagcggat acatatttga atgtatttag aaaaataaac aaatagggg tccgcgcaca tttccccgaa aagtgccacc taaattgtaa gcgttaatat tttgttaaaa ttcgcgttaa attttgtta aatcagctca tttttaacc aataggccga aatcggcaaa atcccttata aatcaaaaga atagaccgag atagggttga gtgttgttcc agtttggaac aagagtccac tattaaagaa cgtggactcc aacgtcaaag ggcgaaaaac cgtctatcag ggcgatggcc cactacgtga accatcaccc taatcaagtt ttttggggtc gaggtgccgt aaagcactaa atcggaaccc taaagggagc ccccgattta gagcttgacg gggaagccg gcgaacgtgg cgagaaagga agggaagaaa gcgaaaggag cgggcgctag ggcgctggca agtgtagcgg tcacgctgcg cgtaaccacc acacccgccg cgcttaatgc gccgctacag ggcgcgtccc attcgccatt caggctgcgc aactgttggg aagggcgatc ggtgcgggcc tcttcgctat tacgccagct ggcgaaaggg ggatgtgctg caaggcgatt aagttgggta acgccagggt tttcccagtc acgacgttgt aaaacgacgg ccagtgagcg cgcgtaatac gactcactat agggcgaatt gggtaccggg cccccctcg aggtcgacgg tatcggggga gctcgcaggg tctccatttt gaagcgggag gtttgaacgc gcagccgcca tgccggggtt ttacgagatt gtgattaagg tccccagcga ccttgacgag catctgcccg gcatttctga cagctttgtg aactgggtgg ccgagaagga atgggagttg ccgccagatt ctgacatgga tctgaatctg attgagcagg cacccctgac cgtggccgag aagctgcagc gcgactttct gacggaatgg cgccgtgtga gtaaggcccc ggaggctctt ttctttgtgc aatttgagaa gggagagagc tacttccaca tgcacgtgct cgtggaaacc accgggtga aatc
```

In SEQ ID NO:5, residues 1-1561 of pAAV-RC7 encode the Rep protein, Rep78 (with residues 91-221 corresponding to the AAV2 P19 promoter, and residues 1075-1254 corresponding to the P40 promoter (SEQ ID NO:18)); residues 1578-3791 encode the AAV7 VP1 capsid protein; residues 736-1281 encode a portion of the Rep68 protein; residues 3987-4117 correspond to the AAV2 P5 promoter sequences of SEQ ID NO:10); residues 4240-4256 are M13 Rev sequences; residues 4264-4280 are Lac operator sequences; 4288-4318 are Lac promoter sequences; residues 4581-5305 correspond to pMB ori sequences, residues 5401-6261 encode an ampicillin resistance determinant; and residues 6262-6360 are bla promoter sequences (FIG. 7).

B. Illustrative Non-AAV Helper Function-Providing Polynucleotides

As used herein, the term "non-AAV helper functions" denotes proteins of Ad, CMV, HSV or other non-AAD viruses (e.g., E1a, E1b, E2a, VA and E4) and/or polynucleotides of Ad, CMV, HSV or other non-AAD viruses that are required for the replication and packaging of an rAAV. Such non-AAV helper functions are provided by a "non-AAV helper function-providing polynucleotide," which as such term is used herein is a virus, plasmid vector, a non-plasmid vector, or a polynucleotide that has been integrated into a cellular chromosome, that provides non-AAV helper functions. The vector, pHelper, and derivatives thereof (such as those commercially available from Cell Biolabs, Inc., Invitrogen, Stratagene and other sources), are suitable non-AAV helper function-providing polynucleotide (see, e.g., Matsushita, T. et al. (1998) "*Adeno-Associated Virus Vectors Can Be Efficiently Produced Without Helper Virus*," Gene Ther. 5:938-945; Sharma, A. et al. (2010) "*Transduction Efficiency Of AAV 2/6, 2/8 And 2/9 Vectors For Delivering Genes In Human Corneal Fibroblasts*," Brain Res. Bull. 81(2-3):273-278).

Figure 8:
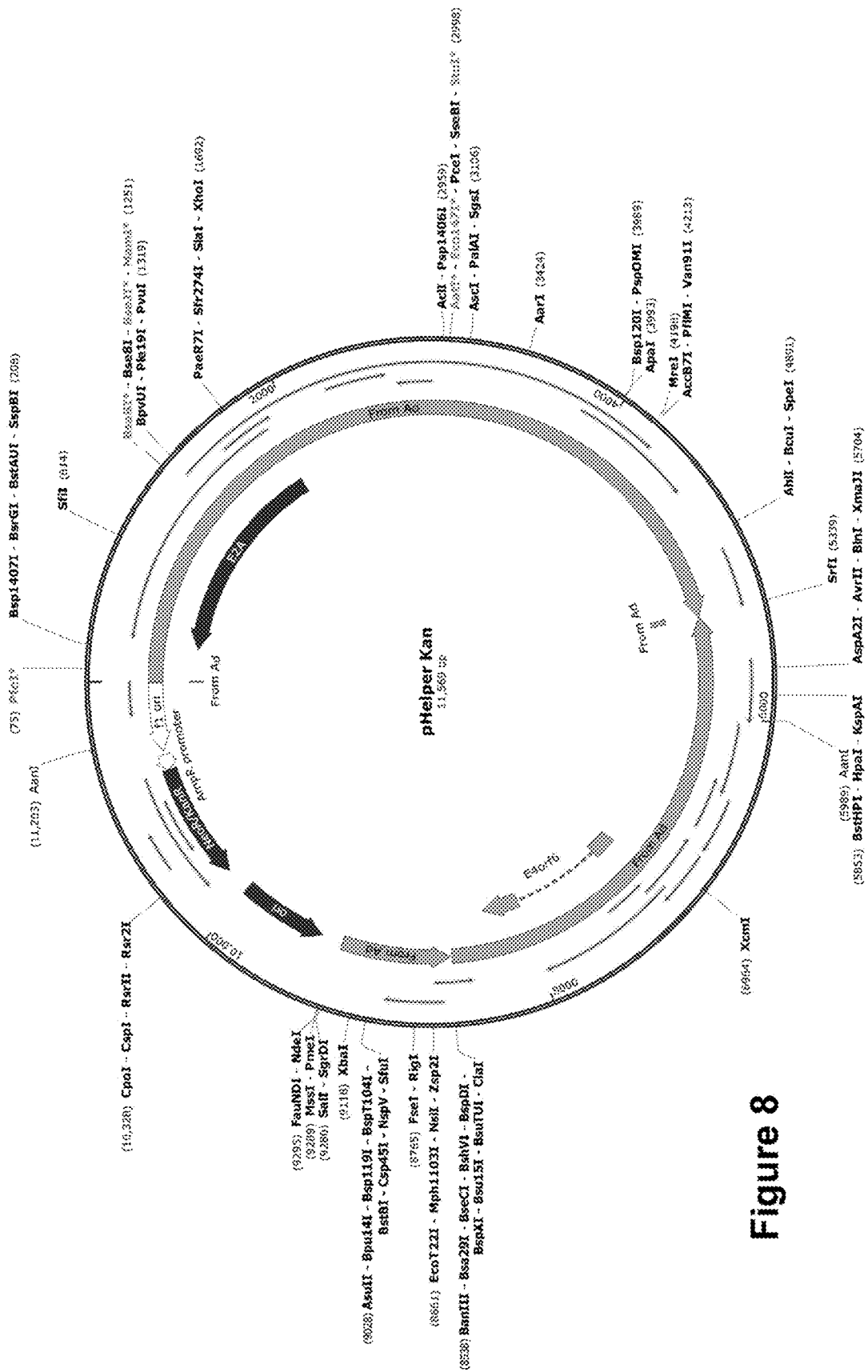
FIG. 8 shows a map of the non-AAV helper plasmid vector pHelper-Kan (SEQ ID NO:6).

Plasmid pHelper-Kan (SEQ ID NO:6; FIG. 8) is a non-AAV helper function-providing polynucleotide that may be used in accordance with the present invention to provide non-AAV helper functions.

| Coding Strand of Plasmid pHelper-Kan (SEQ ID NO:6): |
| --- |
| ggtacccaac tccatgctta acagtcccca ggtacagccc accctgcgtc |
| gcaaccagga acagctctac agcttcctgg agcgccactc gccctacttc |
| cgcagccaca gtgcgcagat taggagcgcc acttcttttt gtcacttgaa |
| aaacatgtaa aaataatgta ctaggagaca ctttcaataa aggcaaatgt |
| ttttatttgt acactctcgg gtgattattt acccccacc cttgccgtct |
| gcgccgttta aaaatcaaag gggttctgcc gcgcatcgct atgcgccact |
| ggcagggaca cgttgcgata ctggtgttta gtgctccact taaactcagg |
| cacaaccatc cgcggcagct cggtgaagtt ttcactccac aggctgcgca |
| ccatcaccaa cgcgtttagc aggtcgggcg ccgatatctt gaagtcgcag |
| ttggggcctc cgccctgcgc gcgcgagttg cgatacacag ggttgcagca |
| ctggaacact atcagcgccg ggtggtgcac gctggccagc acgctcttgt |
| cggagatcag atccgcgtcc aggtcctccg cgttgctcag ggcgaacgga |
| gtcaactttg gtagctgcct tcccaaaaag ggtgcatgcc caggctttga |
| gttgcactcg caccgtagtg gcatcagaag gtgaccgtgc ccggtctggg |
| cgttaggata cagcgcctgc atgaaagcct tgatctgctt aaaagccacc |
| tgagcctttg cgccttcaga gaagaacatg ccgcaagact tgccggaaaa |
| ctgattggcc ggacaggccg cgtcatgcac gcagcacctt gcgtcggtgt |
| tggagatctg caccacattt cggccccacc ggttcttcac gatcttggcc |
| ttgctagact gctccttcag cgcgcgctgc ccgttttcgc tcgtcacatc |
| catttcaatc acgtgctcct tatttatcat aatgctcccg tgtagacact |
| taagctcgcc ttcgatctca gcgcagcggt gcagccacaa cgcgcagccc |
| gtgggctcgt ggtgcttgta ggttacctct gcaaacgact gcaggtacgc |
| ctgcaggaat cgccccatca tcgtcacaaa ggtcttgttg ctggtgaagg |
| tcagctgcaa cccgcggtgc tcctcgttta gccaggtctt gcatacggcc |
| gccagagctt ccacttggtc aggcagtagc ttgaagtttg cctttagatc |
| gttatccacg tggtacttgt ccatcaacgc gcgcgcagcc tccatgccct |
| tctcccacgc agacacgatc ggcaggctca gcgggtttat caccgtgctt |
| tcactttccg cttcactgga ctcttccttt tcctcttgcg tccgcatacc |
| ccgcgccact gggtcgtctt cattcagccg ccgcaccgtg cgcttacctc |
| ccttgccgtg cttgattagc accggtgggt tgctgaaacc caccatttgt |
| agcgccacat cttctctttc ttcctcgctg tccacgatca cctctgggga |
| tggcgggcgc tcgggcttgg gagaggggcg cttcttttc ttttggacg |
| caatggccaa atccgccgtc gaggtcgatg gccgcgggct gggtgtgcgc |
| ggcaccagcg catcttgtga cgagtcttct tcgtcctcgg actcgagacg |

-continued

Coding Strand of Plasmid pHelper-Kan (SEQ ID NO:6):

```
ccgcctcagc cgcttttttg ggggcgcgcg gggaggcggc ggcgacggcg acggggacga cacgtcctcc atggttggtg gacgtcgcgc cgcaccgcgt ccgcgctcgg gggtggtttc gcgctgctcc tcttcccgac tggccatttc cttctcctat aggcagaaaa agatcatgga gtcagtcgag aaggaggaca gcctaaccgc ccccttttgag ttcgccacca ccgcctccac cgatgccgcc aacgcgccta ccaccttccc cgtcgaggca ccccccgcttg aggaggagga agtgattatc gagcaggacc caggttttgt aagcgaagac gacgaggatc gctcagtacc aacagaggat aaaaagcaag accaggacga cgcagaggca aacgaggaac aagtcgggcg gggggaccaa aggcatggcg actacctaga tgtgggagac gacgtgctgt tgaagcatct gcagcgccag tgcgccatta tctgcgacgc gttgcaagag cgcagcgatg tgcccctcgc catagcggat gtcagccttg cctacgaacg ccacctgttc tcaccgcgcg tacccccccaa acgccaagaa aacggcacat gcgagcccaa cccgcgcctc aacttctacc ccgtatttgc cgtgccagag gtgcttgcca cctatcacat cttttttccaa aactgcaaga taccccctatc ctgccgtgcc aaccgcagcc gagcggacaa gcagctggcc ttgcggcagg gcgctgtcat acctgatatc gcctcgctcg acgaagtgcc aaaaatcttt gagggtcttg gacgcgacga gaaacgcgcg gcaaacgctc tgcaacaaga aaacagcgaa atgaaagtc actgtggagt gctggtggaa cttgagggtg acaacgcgcg cctagccgtg ctgaaacgca gcatcgaggt cacccacttt gcctacccgg cacttaacct acccccccaag gttatgagca cagtcatgag cgagctgatc gtgcgccgtg cacgacccct ggagagggat gcaaacttgc aagaacaaac cgaggagggc ctacccgcag ttggcgatga gcagctggcg cgctggcttg agacgcgcga gcctgccgac ttggaggagc gacgcaagct aatgatggcc gcagtgcttg ttaccgtgga gcttgagtgc atgcagcggt tctttgctga cccggagatg cagcgcaagc tagaggaaac gttgcactac acctttcgcc agggctacgt gcgccaggcc tgcaaaattt ccaacgtgga gctctgcaac ctggtctcct accttggaat tttgcacgaa aaccgcctcg ggcaaaacgt gcttcattcc acgctcaagg gcgaggcgcg ccgcgactac gtccgcgact gcgtttactt atttctgtgc tacacctggc aaacggccat gggcgtgtgg cagcaatgcc tggaggagcg caacctaaag gagctgcaga agctgctaaa gcaaaacttg aaggacctat ggacggcctt caacgagcgc tccgtggccg cgcacctggc ggacattatc ttccccgaac gcctgcttaa aaccctgcaa cagggtctgc cagacttcac cagtcaaagc atgttgcaaa actttaggaa ctttatccta gagcgttcag gaattctgcc cgccacctgc tgtgcgcttc ctagcgactt tgtgcccatt aagtaccgtg aatgccctcc gccgctttgg ggtcactgct accttctgca gctagccaac taccttgcct accactccga catcatggaa gacgtgagcg gtgacggcct actggagtgt cactgtcgct gcaacctatg caccccgcac
```

| Coding Strand of Plasmid pHelper-Kan (SEQ ID NO:6): |
|---|
| cgctccctgg tctgcaattc gcaactgctt agcgaaagtc aaattatcgg |
| tacctttgag ctgcagggtc cctcgcctga cgaaaagtcc gcggctccgg |
| ggttgaaact cactccgggg ctgtggacgt cggcttacct tcgcaaattt |
| gtacctgagg actaccacgc ccacgagatt aggttctacg aagaccaatc |
| ccgcccgcca aatgcggagc ttaccgcctg cgtcattacc cagggccaca |
| tccttggcca attgcaagcc atcaacaaag cccgccaaga gtttctgcta |
| cgaaagggac gggggttta cctggacccc cagtccggcg aggagctcaa |
| cccaatcccc ccgccgccgc agccctatca gcagccgcgg gcccttgctt |
| cccaggatgg cacccaaaaa gaagctgcag ctgccgccgc cgccacccac |
| ggacgaggag gaatactggg acagtcaggc agaggaggtt ttggacgagg |
| aggaggagat gatggaagac tgggacagcc tagacgaagc ttccgaggcc |
| gaagaggtgt cagacgaaac accgtcaccc tcggtcgcat tcccctcgcc |
| ggcgccccag aaattggcaa ccgttcccag catcgctaca acctccgctc |
| ctcaggcgcc gccggcactg cctgttcgcc gacccaaccg tagatgggac |
| accactggaa ccagggccgg taagtctaag cagccgccgc cgttagccca |
| agagcaacaa cagcgccaag gctaccgctc gtggcgcggg cacaagaacg |
| ccatagttgc ttgcttgcaa gactgtgggg gcaacatctc cttcgcccgc |
| cgcttttctt tctaccatca cggcgtggcc ttcccccgta acatcctgca |
| ttactaccgt catctctaca gcccctactg caccggcggc agcggcagcg |
| gcagcaacag cagcggtcac acagaagcaa aggcgaccgg atagcaagac |
| tctgacaaag cccaagaaat ccacagcggc ggcagcagca ggaggaggag |
| cgctgcgtct ggcgcccaac gaacccgtat cgacccgcga gcttagaaat |
| aggatttttc ccactctgta tgctatattt caacaaagca ggggccaaga |
| acaagagctg aaaataaaaa acaggtctct gcgctccctc acccgcagct |
| gcctgtatca caaaagcgaa gatcagcttc ggcgcacgct ggaagacgcg |
| gaggctctct tcagcaaata ctgcgcgctg actcttaagg actagtttcg |
| cgccctttct caaatttaag cgcgaaaact acgtcatctc cagcggccac |
| accggcgcc agcacctgtc gtcagcgcca ttatgagcaa ggaaattccc |
| acgccctaca tgtggagtta ccagccacaa atgggacttg cggctggagc |
| tgcccaagac tactcaaccc gaataaacta catgagcgcg gaccccaca |
| tgatatcccg ggtcaacgga atccgcgccc accgaaaccg aattctcctc |
| gaacaggcgg ctattaccac cacacctcgt aataaccta atccccgtag |
| ttggcccgct gccctggtgt accaggaaag tcccgctccc accactgtgg |
| tacttcccag agacgcccag gccgaagttc agatgactaa ctcaggggcg |
| cagcttgcgg gcggcttttcg tcacagggtg cggtcgcccg ggcgttttag |
| ggcggagtaa cttgcatgta ttgggaattg tagttttttt aaaatgggaa |
| gtgacgtatc gtgggaaaac ggaagtgaag atttgaggaa gttgtgggtt |
| ttttggcttt cgttctgggg cgtaggttcg cgtgcggttt tctgggtgtt |
| ttttgtggac tttaaccgtt acgtcatttt ttagtcctat atatactcgc |

| Coding Strand of Plasmid pHelper-Kan (SEQ ID NO:6): |
|---|

```
tctgtacttg ccccttttta cactgtgact gattgagctg gtgccgtgtc
gagtggtgtt ttttaatagg tttttttact ggtaaggctg actgttatgg
ctgccgctgt ggaagcgctg tatgttgttc tggagcggga gggtgctatt
ttgcctaggc aggagggttt ttcaggtgtt tatgtgtttt tctctcctat
taattttgtt atacctccta tggggctgt aatgttgtct ctacgcctgc
gggtatgtat tcccccgggc tatttcggtc gcttttagc actgaccgat
gttaaccaac ctgatgtgtt taccgagtct tacattatga ctccggacat
gaccgaggaa ctgtcggtgg tgcttttaa tcacggtgac cagttttttt
acggtcacgc cggcatggcc gtagtccgtc ttatgcttat aagggttgtt
tttcctgttg taagacaggc ttctaatgtt taaatgtttt tttttttgtt
attttatttt gtgtttaatg caggaacccg cagacatgtt tgagagaaaa
atggtgtctt tttctgtggt ggttccggaa cttacctgcc tttatctgca
tgagcatgac tacgatgtgc ttgcttttt gcgcgaggct ttgcctgatt
ttttgagcag caccttgcat tttatatcgc cgcccatgca acaagcttac
ataggggcta cgctggttag catagctccg agtatgcgtg tcataatcag
tgtgggttct tttgtcatgg ttcctggcgg ggaagtggcc gcgctggtcc
gtgcagacct gcacgattat gttcagctgg ccctgcgaag gacctacgg
gatcgcggta tttttgttaa tgttccgctt ttgaatctta tacaggtctg
tgaggaacct gaattttgc aatcatgatt cgctgcttga ggctgaaggt
ggagggcgct ctggagcaga tttttacaat ggccggactt aatattcggg
atttgcttag agacatattg ataaggtggc gagatgaaaa ttatttgggc
atggttgaag gtgctggaat gtttatagag gagattcacc ctgaagggtt
tagcctttac gtccacttgg acgtgagggc agtttgcctt ttggaagcca
ttgtgcaaca tcttacaaat gccattatct gttctttggc tgtagagttt
gaccacgcca ccggaggga gcgcgttcac ttaatagatc ttcattttga
ggttttggat aatcttttgg aataaaaaaa aaaaaacatg gttcttccag
ctcttcccgc tcctcccgtg tgtgactcgc agaacgaatg tgtaggttgg
ctgggtgtgg cttattctgc ggtggtggat gttatcaggg cagcggcgca
tgaaggagtt tacatagaac ccgaagccag ggggcgcctg gatgctttga
gagagtggat atactacaac tactacacag agcgagctaa gcgacgagac
cggagacgca gatctgtttg tcacgcccgc acctggtttt gcttcaggaa
atatgactac gtccggcgtt ccatttggca tgacactacg accaacacga
tctcggttgt ctcggcgcac tccgtacagt agggatcgcc tacctccttt
tgagacagag acccgcgcta ccatactgga ggatcatccg ctgctgcccg
aatgtaacac tttgacaatg cacaacgtga gttacgtgcg aggtcttccc
tgcagtgtgg gatttacgct gattcaggaa tgggttgttc cctgggatat
ggttctgacg cgggaggagc ttgtaatcct gaggaagtgt atgcacgtgt
gcctgtgttg tgccaacatt gatatcatga cgagcatgat gatccatggt
```

Coding Strand of Plasmid pHelper-Kan (SEQ ID NO:6):

```
tacgagtcct gggctctcca ctgtcattgt tccagtcccg gttccctgca
gtgcatagcc ggcgggcagg ttttggccag ctggtttagg atggtggtgg
atggcgccat gtttaatcag aggtttatat ggtaccggga ggtggtgaat
tacaacatgc aaaagaggt aatgtttatg tccagcgtgt ttatgagggg
tcgccactta atctacctgc gcttgtggta tgatggccac gtgggttctg
tggtccccgc catgagcttt ggatacagcg ccttgcactg tgggattttg
aacaatattg tggtgctgtg ctgcagttac tgtgctgatt taagtgagat
cagggtgcgc tgctgtgccc ggaggacaag gcgtctcatg ctgcgggcgg
tgcgaatcat cgctgaggag accactgcca tgttgtattc ctgcaggacg
gagcggcggc ggcagcagtt tattcgcgcg ctgctgcagc accaccgccc
tatcctgatg cacgattatg actctacccc catgtaggcg tggacttccc
cttcgccgcc cgttgagcaa ccgcaagttg gacagcagcc tgtggctcag
cagctggaca gcgacatgaa cttaagcgag ctgcccgggg agtttattaa
tatcactgat gagcgtttgg ctcgacagga aaccgtgtgg aatataacac
ctaagaatat gtctgttacc catgatatga tgcttttaa ggccagccgg
ggagaaagga ctgtgtactc tgtgtgttgg gagggaggtg gcaggttgaa
tactagggtt ctgtgagttt gattaaggta cggtgatcaa tataagctat
gtggtggtgg ggctatacta ctgaatgaaa aatgacttga aattttctgc
aattgaaaaa taaacacgtt gaaacataac atgcaacagg ttcacgattc
tttattcctg ggcaatgtag gagaaggtgt aagagttggt agcaaaagtt
tcagtggtgt attttccact ttcccaggac catgtaaaag acatagagta
agtgcttacc tcgctagttt ctgtggattc actagaatcg atgtaggatg
ttgcccctcc tgacgcggta ggagaagggg agggtgccct gcatgtctgc
cgctgctctt gctcttgccg ctgctgagga gggggcgca tctgccgcag
caccggatgc atctgggaaa agcaaaaaag gggctcgtcc ctgtttccgg
aggaatttgc aagcggggtc ttgcatgacg gggaggcaaa ccccgttcg
ccgcagtccg gccggcccga gactcgaacc gggggtcctg cgactcaacc
cttggaaaat aaccctccgg ctacagggag cgagccactt aatgctttcg
cttttccagcc taaccgctta cgccgcgcgc ggccagtggc caaaaaagct
agcgcagcag ccgccgcgcc tggaaggaag ccaaaaggag cgctccccg
ttgtctgacg tcgcacacct gggttcgaca cgcgggcggt aaccgcatgg
atcacggcgg acggccggat ccggggttcg aaccccggtc gtccgccatg
ataccctgc gaatttatcc accagaccac ggaagagtgc ccgcttacag
gctctccttt tgcacggtct agagcgtcaa cgactgcgca cgcctcaccg
gccagagcgt cccgaccatg gagcactttt tgccgctgcg caacatctgg
aaccgcgtcc gcgactttcc gcgcgcctcc accaccgccg ccggcatcac
ctggatgtcc aggtacatct acggattacg tcgacgttta aaccatatga
tcagctcact caaaggcggt aatacggtta tccacagaat caggggataa
cgcaggaaag aacatgtgag caaaaggcca gcaaaaggcc aggaaccgta
```

Coding Strand of Plasmid pHelper-Kan (SEQ ID NO:6):

aaaaggccgc gttgctggcg ttttttccata ggctccgccc ccctgacgag catcacaaaa atcgacgctc aagtcagagg tggcgaaacc cgacaggact ataaagatac caggcgtttc ccctggaag ctccctcgtg cgctctcctg ttccgaccct gccgcttacc ggatacctgt ccgcctttct cccttcggga agcgtggcgc tttctcatag ctcacgctgt aggtatctca gttcggtgta ggtcgttcgc tccaagctgg gctgtgtgca cgaaccccc gttcagcccg accgctgcgc cttatccggt aactatcgtc ttgagtccaa cccggtaaga cacgacttat cgccactggc agcagccact ggtaacagga ttagcagagc gaggtatgta ggcggtgcta cagagttctt gaagtggtgg cctaactacg gctacactag aagaacagta tttggtatct gcgctctgct gaagccagtt accttcggaa aaagagttgg tagctcttga tccggcaaac aaaccaccgc tggtagcggt ggtttttttg tttgcaagca gcagattacg cgcagaaaaa aaggatctca agaagatcct ttgatctttt ctacggggtc tgacgctcag tggaacgaaa actcacgtta agggattttg gtcatgagat tatcaaaaag gatcttcacc tagatccttt taaattaaaa atgaagtttt aaatcaatct aaagtatata tgagtaaact tggtctgaca gtcagaagaa ctcgtcaaga aggcgataga aggcgatgcg ctgcgaatcg ggagcggcga taccgtaaag cacgaggaag cggtcagccc attcgccgcc aagctcttca gcaatatcac gggtagccaa cgctatgtcc tgatagcggt ccgccacacc cagccggcca cagtcgatga atccagaaaa gcggccattt tccaccatga tattcggcaa gcaggcatcg ccatgggtca cgacgagatc ctcgccgtcg gcatgctcg ccttgagcct ggcgaacagt tcggctggcg cgagcccctg atgctcttcg tccagatcat cctgatcgac aagaccggct tccatccgag tacgtgctcg ctcgatgcga tgtttcgctt ggtggtcgaa tgggcaggta gccggatcaa gcgtatgcag ccgccgcatt gcatcagcca tgatggatac tttctcggca ggagcaaggt gagatgacag gagatcctgc cccggcactt cgcccaatag cagccagtcc cttcccgctt cagtgacaac gtcgagtaca gctgcgcaag gaacgcccgt cgtggccagc cacgatagcc gcgctgcctc gtcttgcagt tcattcaggg caccggacag gtcggtcttg acaaaaagaa ccgggcgccc ctgcgctgac agccggaaca cggcggcatc agagcagccg attgtctgtt gtgcccagtc atagccgaat agcctctcca cccaagcggc cggagaacct gcgtgcaatc catcttgttc aatcatactc ttccttttc aatattattg aagcatttat cagggttatt gtctcatgag cggatacata tttgaatgta tttagaaaaa taaacaaata ggggttccgc gcacatttcc ccgaaaagtg ccacctaaat tgtaagcgtt aatattttgt taaaattcgc gttaaatttt tgttaaatca gctcattttt taaccaatag gccgaaatcg gcaaaatccc ttataaatca aagaataga ccgagatagg gttgagtgtt gttccagttt ggaacaagag tccactatta aagaacgtgg actccaacgt caaagggcga Coding Strand of Plasmid pHelper-Kan (SEQ ID NO:6):

```
aaaaccgtct atcagggcga tggcccacta cgtgaaccat caccctaatc aagtttttg gggtcgaggt gccgtaaagc actaaatcgg aaccctaaag ggagcccccg atttagagct tgacgggaa agccggcgaa cgtggcgaga aaggaaggga agaaagcgaa aggagcgggc gctagggcgc tggcaagtgt agcggtcacg ctgcgcgtaa ccaccacacc cgccgcgctt aatgcgccgc tacagggcgc gatggatcc
```

In SEQ ID NO:6, residues 1-5343 of pHelper-Kan are derived from adenovirus, and include a polynucleotide encoding the E2A protein (residues 258-1847); residues 5344-8535 are derived from adenovirus, and include a polynucleotide encoding the E4orf6 protein; residues 9423-10011 correspond to ori sequences; residues 10182-10976 encode a kanamycin resistance determinant expressed by a bla promoter sequence (residues 10977-11081); residues 11107-11561 correspond to fl ori sequences (FIG. 8).

C. Illustrative rAAV Plasmid Vectors

Figure 9:
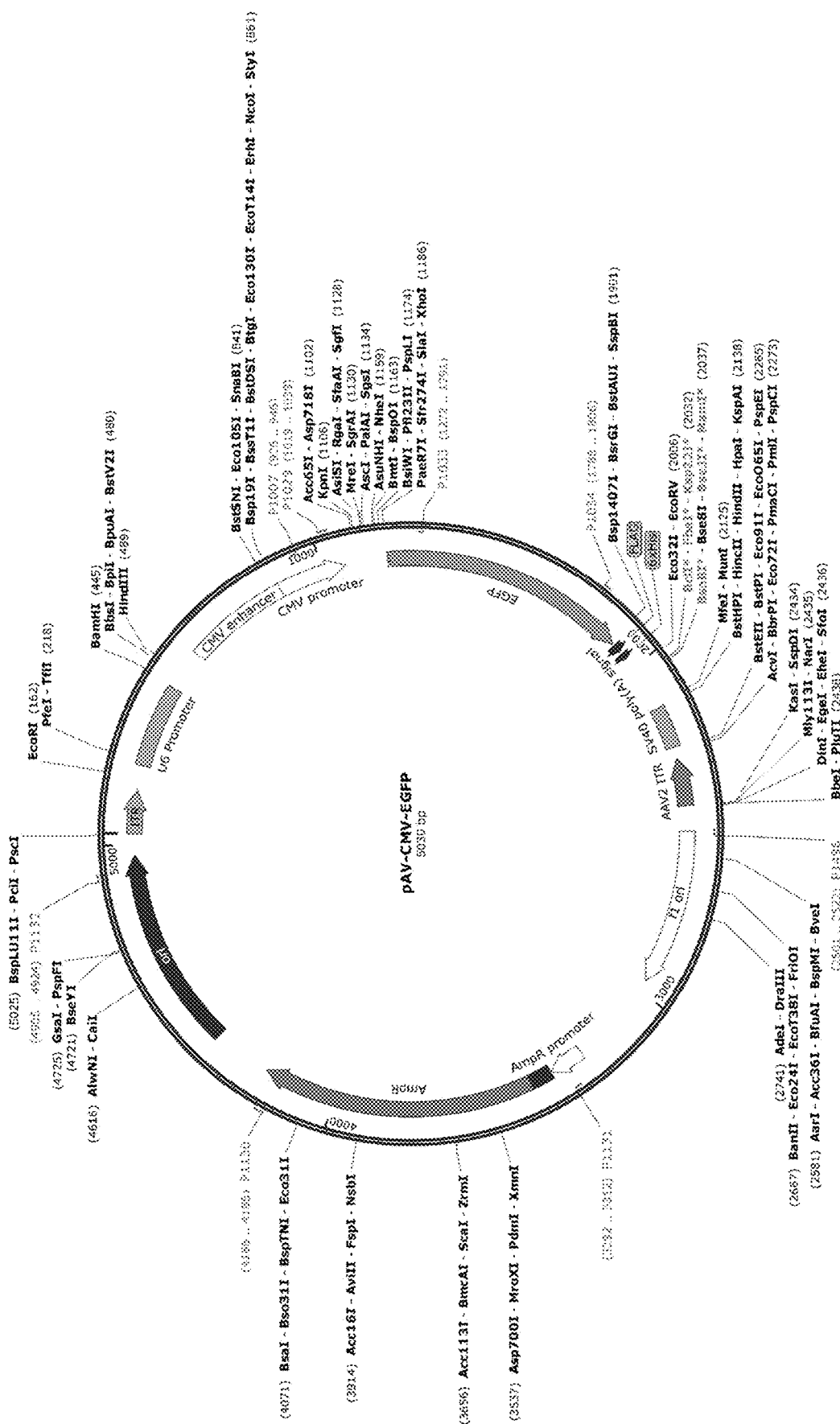
FIG. 9 shows a map of the rAAV plasmid vector pAV-CMV-EGFP (SEQ ID NO:7).

As discussed above, AAV helper function-providing polynucleotides and non-AAV helper function-providing polynucleotides are typically employed in concert with an rAAV plasmid vector to comprise a triple plasmid transfection system. Multiple commercially available rAAV plasmid vectors (e.g., pAV-CMV-EGFP, pGOI, etc. (Cell Biolabs, Inc., Invitrogen and Stratagene)) may be used in accordance with the present invention. An illustrative rAAV plasmid vector that may be used in accordance with the present invention is pAV-CMV-EGFP (SEQ ID NO:7; FIG. 9) which comprises a 5' ITR, a U6 promoter, CMV enhancer and promoter sequences, a polynucleotide encoding the enhanced green fluorescent protein (EGFP) (Gambotto, A. et al. (2000) "*Immunogenicity Of Enhanced Green Fluorescent Protein (EGFP) In BALB/C Mice: Identification Of An H2-Kd-Restricted CTL Epitope,*" Gene Ther. 7(23):2036-2040; Tsien, R. Y. (1998) "*The Green Fluorescent Protein,*" Annu. Rev. Biochem. 67:509-544; Cinelli, R. A. et al. (2000) "*The Enhanced Green Fluorescent Protein As A Tool For The Analysis Of Protein Dynamics And Localization: Local Fluorescence Study At The Single-Molecule Level,*" Photochem. Photobiol. 71(6):771-776; Chopra A. (2008) "*Recombinant Adenovirus With Enhanced Green Fluorescent Protein,*" In: MOLECULAR IMAGING AND CONTRAST AGENT DATABASE (MICAD), National Center for Biotechnology Information, Bethesda Md.), FLAG-tag and 6xHis-tag sites for facilitating recovery or localization of expressed proteins, an SV40 poly(A) site and a 3' ITR.

Coding Strand of Plasmid pAV-CMV-EGFP (SEQ ID NO:7):

```
cctgcaggca gctgcgcgct cgctcgctca ctgaggccgc ccgggcgtcg ggcgaccttt ggtcgcccgg ccctccagtg agcgagcgcg cagagaggga gtggccaact ccatcactag gggttcctgc ggccgcacgc gtctagttat taatagtaat cgaattcgtg ttactcataa ctagtaaggt cgggcaggaa gagggcctat ttcccatgat tccttcatat ttgcatatac gatacaaggc tgttagagag ataattagaa ttaatttgac tgtaaacaca aagatattag tacaaaatac gtgacgtaga aagtaataat ttcttgggta gtttgcagtt ttaaaattat gttttaaaat ggactatcat atgcttaccg taacttgaaa gtatttcgat ttcttgggtt tatatatctt gtggaaagga cgcgggatcc actggaccag gcagcagcgt cagaagactt ttttggaaaa gcttgactag taatactgta atagtaatca attacggggt cattagttca tagcccatat atggagttcc gcgttacata acttacggta aatggcccgc ctggctgacc gcccaacgac ccccgcccat tgacgtcaat aatgacgtat gttcccatag taacgccaat agggactttc cattgacgtc aatgggtgga gtatttacgg taaactgccc acttggcagt acatcaagtg tatcatatgc caagtacgcc ccctattgac gtcaatgacg gtaaatggcc cgcctggcat tatgcccagt acatgacctt atgggacttt cctacttggc agtacatcta cgtattagtc atcgctatta ccatggtgat gcggttttgg cagtacatca atgggcgtgg atagcggttt gactcacggg gatttccaag tctccacccc attgacgtca
```

Coding Strand of Plasmid pAV-CMV-EGFP (SEQ ID NO:7):

```
atgggagttt gttttgcacc aaaatcaacg ggactttcca aaatgtcgta
acaactccgc cccattgacg caaatgggcg gtaggcgtgt acggtgggag
gtctatataa gcagagctgg tttagtgaac cgtcagatcc gctagagatc
cggtaccgag gagatctgcc gccgcgatcg ccggcgcgcc agatctcacg
cttaactagc tagcggaccg acgcgtacgc ggccgctcga gatggtgagc
aagggcgagg agctgttcac cggggtggtg cccatcctgg tcgagctgga
cggcgacgta aacggccaca agttcagcgt gtccggcgag ggcgagggcg
atgccaccta cggcaagctg accctgaagt tcatctgcac caccggcaag
ctgcccgtgc cctggcccac cctcgtgacc accctgacct acggcgtgca
gtgcttcagc cgctaccccg accacatgaa gcagcacgac ttcttcaagt
ccgccatgcc cgaaggctac gtccaggagc gcaccatctt cttcaaggac
gacggcaact acaagacccg cgccgaggtg aagttcgagg gcgacaccct
ggtgaaccgc atcgagctga agggcatcga cttcaaggag gacggcaaca
tcctggggca caagctggag tacaactaca acagccacaa cgtctatatc
atggccgaca agcagaagaa cggcatcaag gtgaacttca gatccgcca
caacatcgag gacggcagcg tgcagctcgc cgaccactac cagcagaaca
cccccatcgg cgacggcccc gtgctgctgc ccgacaacca ctacctgagc
acccagtccg ccctgagcaa agaccccaac gagaagcgcg atcacatggt
cctgctggag ttcgtgaccg ccgccgggat cactctcggc atggacgagc
tgtacaagta agtcgaggat tataaggatg acgacgataa attcgtcgag
caccaccacc accaccacta ataaggttta tccgatccac cggatctaga
taagatatcc gatccaccgg atctagataa ctgatcataa tcagccatac
cacatttgta gaggttttac ttgctttaaa aaacctccca cacctccccc
tgaacctgaa acataaaatg aatgcaattg ttgttgttaa cttgtttatt
gcagcttata atggttacaa ataaagcaat agcatcacaa atttcacaaa
taaagcattt ttttcactgc attctagttg tggtttgtcc aaactcatca
atgtatctta acgcggtaac cacgtgcgga ccgagcggcc gcaggaaccc
ctagtgatgg agttggccac tccctctctg cgcgctcgct cgctcactga
ggccgggcga ccaaaggtcg cccgacgccc gggctttgcc cgggcggcct
cagtgagcga gcgagcgcgc agctgcctgc aggggcgcct gatgcggtat
tttctcctta cgcatctgtg cggtatttca caccgcatac gtcaaagcaa
ccatagtacg cgccctgtag cggcgcatta agcgcggcgg gtgtggtggt
tacgcgcagc gtgaccgcta cacctgccag cgccttagcg cccgctcctt
tcgctttctt cccttccttt ctcgccacgt tcgccggctt tccccgtcaa
gctctaaatc gggggctccc tttagggttc cgatttagtg ctttacggca
cctcgacccc aaaaaacttg atttgggtga tggttcacgt agtgggccat
cgccctgata gacggttttt cgccctttga cgttggagtc cacgttcttt
aatagtggac tcttgttcca aactggaaca acactcaacc ctatctcggg
```

| Coding Strand of Plasmid pAV-CMV-EGFP (SEQ ID NO:7): |
|---|
| ctattctttt gatttataag ggattttgcc gatttcggcc tattggttaa |
| aaaatgagct gatttaacaa aaatttaacg cgaattttaa caaaatatta |
| acgtttacaa ttttatggtg cactctcagt acaatctgct ctgatgccgc |
| atagttaagc cagccccgac acccgccaac acccgctgac gcgccctgac |
| gggcttgtct gctcccggca tccgcttaca gacaagctgt gaccgtctcc |
| gggagctgca tgtgtcagag gttttcaccg tcatcaccga aacgcgcgag |
| acgaaagggc ctcgtgatac gcctattttt ataggttaat gtcatgataa |
| taatggtttc ttagacgtca ggtggcactt ttcggggaaa tgtgcgcgga |
| acccctattt gtttattttt ctaaatacat tcaaatatgt atccgctcat |
| gagacaataa ccctgataaa tgcttcaata atattgaaaa aggaagagta |
| tgagtattca acatttccgt gtcgccctta ttcccttttt tgcggcattt |
| tgccttcctg ttttttgctca cccagaaacg ctggtgaaag taaaagatgc |
| tgaagatcag ttgggtgcac gagtgggtta catcgaactg gatctcaaca |
| gcggtaagat ccttgagagt tttcgccccg aagaacgttt tccaatgatg |
| agcactttta aagttctgct atgtggcgcg gtattatccc gtattgacgc |
| cgggcaagag caactcggtc gccgcataca ctattctcag aatgacttgg |
| ttgagtactc accagtcaca gaaaagcatc ttacggatgg catgacagta |
| agagaattat gcagtgctgc cataaccatg agtgataaca ctgcggccaa |
| cttacttctg acaacgatcg gaggaccgaa ggagctaacc gcttttttgc |
| acaacatggg ggatcatgta actcgccttg atcgttggga accggagctg |
| aatgaagcca taccaaacga cgagcgtgac accacgatgc ctgtagcaat |
| ggcaacaacg ttgcgcaaac tattaactgg cgaactactt actctagctt |
| cccggcaaca attaatagac tggatggagg cggataaagt tgcaggacca |
| cttctgcgct cggcccttcc ggctggctgg tttattgctg ataaatctgg |
| agccggtgag cgtgggtctc gcggtatcat tgcagcactg gggccagatg |
| gtaagccctc ccgtatcgta gttatctaca cgacggggag tcaggcaact |
| atggatgaac gaaatagaca gatcgctgag ataggtgcct cactgattaa |
| gcattggtaa ctgtcagacc aagtttactc atatatactt tagattgatt |
| taaaacttca ttttaatttt aaaaggatct aggtgaagat cctttttgat |
| aatctcatga ccaaaatccc ttaacgtgag ttttcgttcc actgagcgtc |
| agaccccgta gaaaagatca aaggatcttc ttgagatcct ttttttctgc |
| gcgtaatctg ctgcttgcaa acaaaaaaac caccgctacc agcggtggtt |
| tgtttgccgg atcaagagct accaactctt tttccgaagg taactggctt |
| cagcagagcg cagataccaa atactgtcct tctagtgtag ccgtagttag |
| gccaccactt caagaactct gtagcaccgc ctacatacct cgctctgcta |
| atcctgttac cagtggctgc tgccagtggc gataagtcgt gtcttaccgg |
| gttggactca agacgatagt taccggataa ggcgcagcgg tcgggctgaa |
| cggggggttc gtgcacacag cccagcttgg agcgaacgac ctacaccgaa |
| ctgagatacc tacagcgtga gctatgagaa agcgccacgc ttcccgaagg |

-continued

Coding Strand of Plasmid pAV-CMV-EGFP (SEQ ID NO:7):

```
gagaaaggcg gacaggtatc cggtaagcgg cagggtcgga acaggagagc gcacgaggga gcttccaggg ggaaacgcct ggtatcttta tagtcctgtc gggtttcgcc acctctgact tgagcgtcga tttttgtgat gctcgtcagg ggggcggagc ctatggaaaa acgccagcaa cgcggccttt ttacggttcc tggccttttg ctggcctttt gctcacatgt
```

In SEQ ID NO:7, residues 1-128 of pAV-CMV-EGFP correspond to the 5' ITR; residues 201-441 are U6 promoter sequences; residues 562-865 are human cytomegalovirus (CMV) immediate early enhancer sequences; residues 866-1068 comprise the CMV immediate early promoter; residues 1192-1911 comprise a mammalian codon-optimized polynucleotide that encodes the EGFP; residues 1918-1941 encode the FLAG-tag; residues 1951-1968 encode the 6xHis-tag; residues 2139-2260 encode the SV40 poly(A) sequence; residues 2293-2433 correspond to the 3' ITR; residues 2508-22963 correspond to F1 ori sequences; residues 3350-4210 encode an ampicillin resistance determinant and its signal sequence (residues 3350-3418) expressed by a bla promoter sequence (residues 3245-3349); residues 4381-4969 correspond to an ori sequence (FIG. 9).

Figure 10:
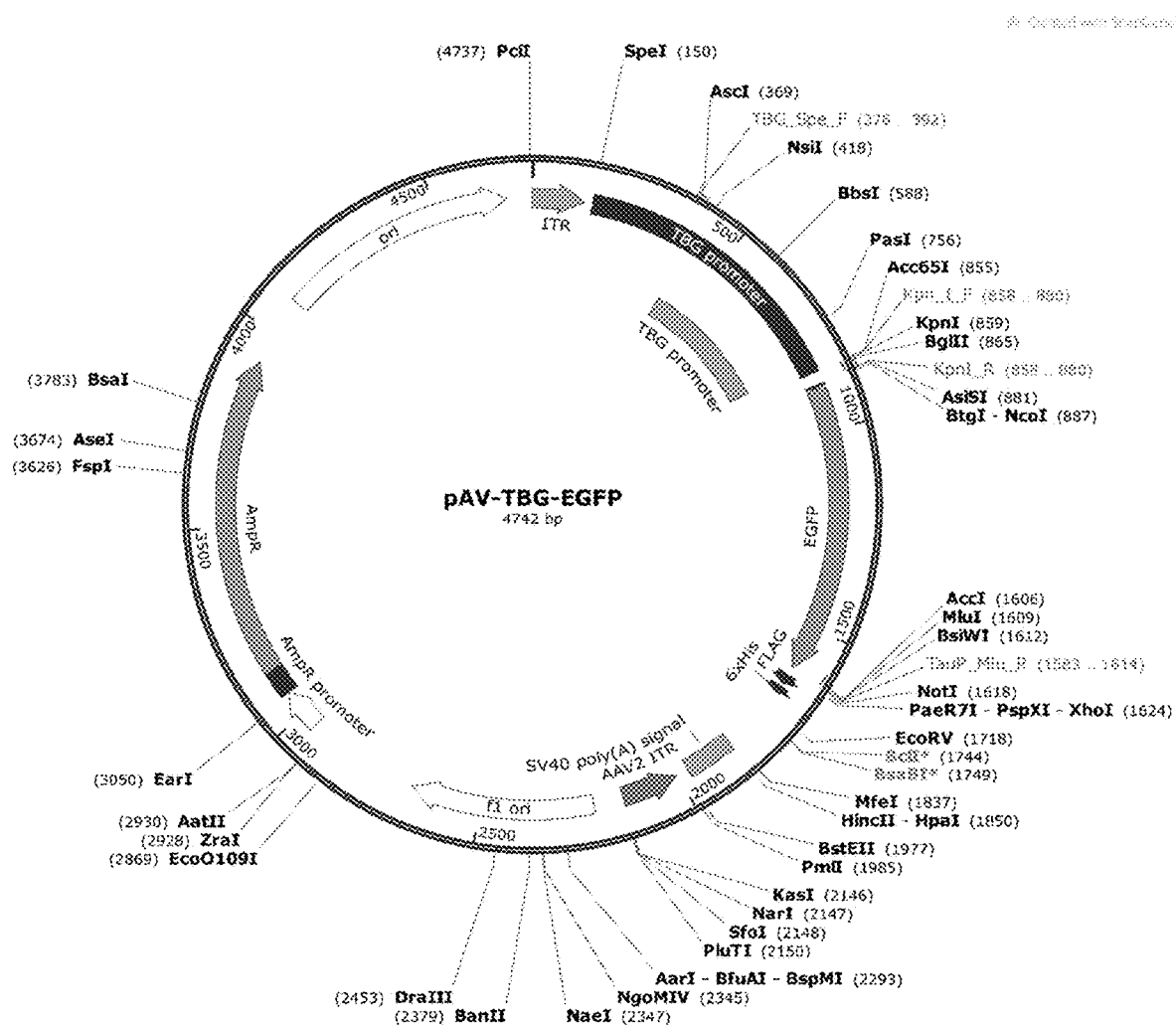
FIG. 10 shows a map of the rAAV plasmid vector pAV-TBG-EGFP (SEQ ID NO:8).

A second illustrative rAAV plasmid vector that may be used in accordance with the present invention is pAV-TBG-EGFP (SEQ ID NO:8; FIG. 10) which comprises a 5' ITR, a thyroid hormone-binding globulin (TBG) promoter, a polynucleotide encoding the enhanced green fluorescent protein (EGFP), FLAG-tag and 6xHis-tag sites for facilitating recovery or localization of expressed proteins, an SV40 poly(A) site and a 3' ITR.

Coding Strand of Plasmid pAV-TBG-EGFP (SEQ ID NO:8):

```
cctgcaggca gctgcgcgct cgctcgctca ctgaggccgc ccgggcgtcg ggcgaccttt ggtcgccgg cctcagtgag cgagcgagcg cgcagagagg gagtggccaa ctccatcact aggggttcct gcggccggtc gcgtctagta ctagtaggtt aatttttaaa aagcagtcaa aagtccaagt ggcccttggc agcatttact ctctctgttt gctctggtta ataatctcag gagcacaaac attccagatc caggttaatt tttaaaaagc agtcaaaagt ccaagtggcc cttggcagca tttactctct ctgtttgctc tggttaataa tctcaggagc acaaacattc cagatccggc gcgccagggc tggaagctac ctttgacatc atttcctctg cgaatgcatg tataatttct acagaaccta ttagaaagga tcacccagcc tctgcttttg tacaactttc ccttaaaaaa ctgccaattc cactgctgtt tggcccaata gtgagaactt tttcctgctg cctcttggtg cttttgccta tggcccctat tctgcctgct gaagacactc ttgccagcat ggacttaaac ccctccagct ctgacaatcc tctttctctt ttgttttaca tgaagggtct ggcagccaaa gcaatcactc aaagttcaaa ccttatcatt ttttgctttg ttcctcttgg ccttggtttt gtacatcagc tttgaaaata ccatcccagg gttaatgctg gggttaattt ataactaaga gtgctctagt tttgcaatac aggacatgct ataaaaatgg aaagatgttg ctttctgaga gacaggtacc gaggagatct gccgccgcga tcgccaccat ggtgagcaag ggcgaggagc tgttcaccgg ggtggtgccc atcctggtcg agctggacgg cgacgtaaac ggccacaagt tcagcgtgtc cggcgagggc gagggcgatg ccacttacgg caagctgacc ctgaagttca tctgcaccac cggcaagctg cccgtgccct ggcccaccct cgtgaccacc ctgacctacg gcgtgcagtg cttcagccgc tacccgacc acatgaagca gcacgacttc ttcaagtccg ccatgcccga aggctacgtc caggagcgca ccatcttctt caaggacgac
```

Coding Strand of Plasmid pAV-TBG-EGFP (SEQ ID NO:8):

```
ggcaactaca agacccgcgc cgaggtgaag ttcgagggcg acaccctggt
gaaccgcatc gagctgaagg gcatcgactt caaggaggac ggcaacatcc
tggggcacaa gctggagtac aactacaaca gccacaacgt ctatatcatg
gccgacaagc agaagaacgg catcaaggtg aacttcaaga tccgccacaa
catcgaggac ggcagcgtgc agctcgccga ccactaccag cagaacaccc
ccatcggcga cggccccgtg ctgctgcccg acaaccacta cctgagcacc
cagtccgccc tgagcaaaga ccccaacgag aagcgcgatc acatggtcct
gctggagttc gtgaccgccg ccgggatcac tctcggcatg gacgagctgt
acaagtagac gcgtacgcgg ccgctcgagg attataagga tgacgacgat
aaattcgtcg agcaccacca ccaccaccac taataaggtt tatccgatcc
accggatcta gataagatat ccgatccacc ggatctagat aactgatcat
aatcagccat accacatttg tagaggtttt acttgcttta aaaaacctcc
cacacctccc cctgaacctg aaacataaaa tgaatgcaat tgttgttgtt
aacttgttta ttgcagctta taatggttac aaataaagca atagcatcac
aaatttcaca ataaagcat ttttttcact gcattctagt tgtggtttgt
ccaaactcat caatgtatct taacgcggta accacgtgcg gacccaacgg
ccgcaggaac ccctagtgat ggagttggcc actccctctc tgcgcgctcg
ctcgctcact gaggccgggc gaccaaaggt cgcccgacgc ccgggctttg
cccgggcggc ctcagtgagc gagcgagcgc gcagctgcct gcaggggcgc
ctgatgcggt attttctcct tacgcatctg tgcggtattt cacaccgcat
acgtcaaagc aaccatagta cgcgcccgt agcggcacat taagcgcggc
gggtgtggtg gttacgcgca gcgtgaccgc tacacctgcc agcgccttag
cgcccgctcc tttcgctttc ttcccttcct ttctcgccac gttcgccggc
tttccccgtc aagctctaaa tcgggggctc cctttagggt tccgatttag
tgctttacgg cacctcgacc ccaaaaaact tgatttgggt gatggttcac
gtagtgggcc atcgccctga tagacggttt ttcgcccttt gacgttggag
tccacgttct ttaatagtgg actcttgttc caaactggaa caacactcaa
ctctatctcg ggctattctt ttgatttata agggattttg ccgatttcgg
tctattggtt aaaaaatgag ctgatttaac aaaaatttaa cgcgaatttt
aacaaaatat taacgtttac aattttatgg tgcactctca gtacaatctg
ctctgatgcc gcatagttaa gccagccccg acacccgcca cacccgctg
acgcgccctg acgggcttgt ctgctcccgg catccgctta cagacaagct
gtgaccgtct ccgggagctg catgtgtcag aggttttcac cgtcatcacc
gaaacgcgcg agacgaaagg gcctcgtgat acgcctattt ttataggtta
atgtcatgat aataatggtt tcttagacgt caggtggcac ttttcgggga
aatgtgcgcg gaacccctat ttgtttattt ttctaaatac attcaaatat
gtatccgctc atgagacaat aaccctgata aatgcttcaa taatattgaa
aaaggaagag tatgagtatt caacatttcc gtgtcgccct tattccctt
```

-continued

| Coding Strand of Plasmid pAV-TBG-EGFP (SEQ ID NO:8): |
|---|

```
tttgcggcat tttgccttcc tgtttttgct cacccagaaa cgctggtgaa agtaaaagat gctgaagatc agttgggtgc acgagtgggt tacatcgaac tggatctcaa cagcggtaag atccttgaga gttttcgccc cgaagaacgt tttccaatga tgagcacttt taaagttctg ctatgtggcg cggtattatc ccgtattgac gccgggcaag agcaactcgg tcgccgcata cactattctc agaatgactt ggttgagtac tcaccagtca cagaaaagca tcttacggat ggcatgacag taagagaatt atgcagtgct gccataacca tgagtgataa cactgcggcc aacttacttc tgacaacgat cggaggaccg aaggagctaa ccgctttttt gcacaacatg gggatcatg taactcgcct tgatcgttgg gaaccggagc tgaatgaagc cataccaaac gacgagcgtg acaccacgat gcctgtagca atggcaacaa cgttgcgcaa actattaact ggcgaactac ttactctagc ttcccggcaa caattaatag actggatgga ggcggataaa gttgcaggac cacttctgcg ctcggccctt ccggctggct ggtttattgc tgataaatct ggagccggtg agcgtgggtc tcgcggtatc attgcagcac tggggccaga tggtaagccc tcccgtatcg tagttatcta cacgacgggg agtcaggcaa ctatggatga acgaaataga cagatcgctg ataggtgc ctcactgatt aagcattggt aactgtcaga ccaagtttac tcatatatac tttagattga tttaaaactt catttttaat ttaaaaggat ctaggtgaag atcctttttg ataatctcat gaccaaaatc ccttaacgtg agttttcgtt ccactgagcg tcagacccg tagaaaagat caaaggatct tcttgagatc ctttttttct gcgcgtaatc tgctgcttgc aaacaaaaaa accaccgcta ccagcggtgg tttgtttgcc ggatcaagag ctaccaactc ttttccgaa ggtaactggc ttcagcagag cgcagatacc aaatactgtt cttctagtgt agccgtagtt aggccaccac ttcaagaact ctgtagcacc gcctacatac ctcgctctgc taatcctgtt accagtggct gctgccagtg gcgataagtc gtgtcttacc gggttggact caagacgata gttaccggat aaggcgcagc ggtcgggctg aacggggggt tcgtgcacac agcccagctt ggagcgaacg acctacaccg aactgagata cctacagcgt gagctatgag aaagcgccac gcttcccgaa gggagaaagg cggacaggta tccggtaagc ggcagggtcg gaacaggaga gcgcacgagg gagcttccag ggggaaacgc ctggtatctt tatagtcctg tcgggtttcg ccacctctga cttgagcgtc gatttttgtg atgctcgtca ggggggcgga gcctatggaa aaacgccagc aacgcggcct ttttacggtt cctggccttt tgctggcctt ttgctcacat gt
```

In SEQ ID NO:8, residues 1-130 of pAV-TBG-EGFP correspond to the 5' ITR; residues 150-854 are TBG promoter sequences, with residues 415-824 comprising the TBG promoter; residues 886-1608 encode the EGFP; residues 1630-1653 encode the FLAG-tag; residues 1663-1680 encode the 6×His-tag; residues 1851-1972 encode the poly (A) sequence; residues 2005-2145 corresponds to the 3' ITR; residues 2220-2675 correspond to F1 ori sequences; residues 3062-3922 encode an ampicillin resistance determinant and its signal sequence (residues 3062-3130) expressed by a bla promoter sequence (residues 2957-3061); residues 4093-4681 correspond to an ori sequence (FIG. 10).

As used herein, the term "native AAV serotype promoter sequence" is intended to denote a promoter sequence that natively controls the transcription of an AAV rep gene or is natively present within such rep gene. For example:

AAV1 P5 promoter sequences natively control the transcription of the rep gene of AAV1 and AAV1 P40 promoter sequences are natively found within the rep gene of AAV1. Thus, the AAV1 P5 promoter sequences and the AAV1 P40 promoter sequences are native AAV serotype promoter sequences of the rep gene of AAV1;

AAV2 P5 promoter sequences natively control the transcription of the rep gene of AAV2 and the AAV2 P40 promoter sequences are natively found within the rep gene of AAV2. Thus, the AAV2 P5 promoter sequences and the AAV2 P40 promoter sequences are native AAV serotype promoter sequences of the rep gene of AAV2;

AAV5 P5 promoter sequences natively control the transcription of the rep gene of AAV5 and the AAV5 P40 promoter sequences are natively found within the rep gene of AAV5. Thus, the AAV5 P5 promoter sequences and the AAV5 P40 promoter sequences are native AAV serotype promoter sequences of the rep gene of AAV5;

AAV6 P5 promoter sequences natively control the transcription of the rep gene of AAV6 and the AAV6 P40 promoter sequences are natively found within the rep gene of AAV6. Thus, the AAV6 P5 promoter sequences and the AAV6 P40 promoter sequences are native AAV serotype promoter sequences of the rep gene of AAV6; and AAV7 P5 promoter sequences natively control the transcription of the rep gene of AAV7 and the AAV7 P40 promoter sequences are natively found within the rep gene of AAV7. Thus, the AAV7 P5 promoter sequences and the AAV7 P40 promoter sequences are native AAV serotype promoter sequences of the rep gene of AAV7;

Native AAV P5 and P40 promoter sequences for AAV serotypes 1-8 are shown in Table 1. Such sequences, or subsequences thereof that are capable of mediating transcription, may be used in accordance with the methods of the present invention.

TABLE 1

| SEQ ID NO | AAV Promoter | Native Serotype | Sequence |
|---|---|---|---|
| SEQ ID NO:9 | P5 | AAV1 | ggtcctgtat tagctgtcac gtgagtgctt ttgcgacatt ttgcgacacc acgtggccat ttagggtata tatggccgag tgagcgagca ggatctccat tttgaccgcg aaatttgaac gagcagcagc c |
| SEQ ID NO:10 | P5 | AAV2 | ggtcctgtat tagaggtcac gtgagtgttt tgcgacattt tgcgacacca tgtggtcacg ctgggtattt aagcccgagt gagcacgcag ggtctccatt ttgaagcggg aggtttgaac gcgcagccgc c |
| SEQ ID NO:11 | P5 | AAV3 | ccagctgcgt cagcagtcag gtgacccttt tgcgacagtt tgcgacacca cgtggccgct gagggtatat attctcgagt gagcgaacca ggagctccat tttgaccgcg aaatttgaac gagcagcagc c |
| SEQ ID NO:12 | P5 | AAV4 | ggtccctgta ttagcagtca cgtgagtgtc gtatttcgcg gagcgtagcg gagcgcatac caagctgcca cgtcacagcc acgtggtccg tttgcgacag tttgcgacac catgtggtca ggagggtata taaccgcgag tgagccagcg aggagctcca ttttgcccgc gaattttgaa cgagcagcag cc |
| SEQ ID NO:13 | P5 | AAV5 | atgtgatgtg ttttatccaa taggaagaaa gcgcgcgtat gagttctcgc gagacttccg gggtataaaa gaccgagtga acgagcccgc cgccattctt tgctctggac tgctagagga ccctcgctgc c |
| SEQ ID NO:14 | P5 | AAV6 | ggtcctgtat tagaggtcac gtgagtgttt tgcgacattt tgcgacacca tgtggtcacg ctgggtattt aagcccgagt gagcacgcag ggtctccatt ttgaagcggg aggtttgaac gcgcagcgcc |
| SEQ ID NO:15 | P5 | AAV7 | ggtcctgtat tagctgtcac gtgagtgctt ttgcgacatt ttgcgacacc acgtggccat ttgaggtata tatggccgag tgagcgagca ggatctccat tttgaccgcg aaatttgaac gagcagcagc c |
| SEQ ID NO:16 | P5 | AAV8 | ggtcctgtat tagctgtcac gtgagtgctt ttgcggcatt ttgcgacacc acgtggccat ttgaggtata tatggccgag tgagcgagca ggatctccat tttgaccgcg aaatttgaac gagcagcagc c |
| SEQ ID NO:17 | P40 | AAV1 | ggtgacaaag caggaagtca aagagttctt ccgctgggcg caggatcacg tgaccgaggt ggcgcatgag ttctacgtca gaaagggtgg agccaacaaa agacccgccc ccgatgacgc |

TABLE 1-continued

| SEQ ID NO | AAV Promoter | Native Serotype | Sequence |
|---|---|---|---|
| | | | ggataaaagc gagcccaagc gggcctgccc ctcagtcgcg gatccatcga cgtcagacgc ggtcaccaag caggaagtca aagactttt |
| SEQ ID NO:18 | P40 | AAV2 | ccggtgggca aaggatcacg tggttgaggt ggagcatgaa ttctacgtca aaaagggtgg agccaagaaa agacccgccc ccagtgacgc agatataagt gagcccaaac gggtgcgcga gtcagttgcg cagccatcga cgtcagacgc ggtcaccaaa caggaagtaa aggactttt |
| SEQ ID NO:19 | P40 | AAV3 | ccggtgggct tccgatcacg tgactgacgt ggctcatgag ttctacgtca gaaagggtgg agctaagaaa cgccccgcct ccaatgacgc ggatgtaagc gagccaaaac gggagtgcac gtcacttgcg cagccgacaa cgtcagacgc |
| SEQ ID NO:20 | P40 | AAV4 | ggtcaccaag caggaagtca aagactttt ccggtgggcg tcagatcacg tgaccgaggt gactcacgag ttttacgtca gaaagggtgg agctagaaag aggcccgccc ccaatgacgc agatataagt gagcccaagc gggcctgtcc gtcagttgcg cagccatcga cgtcagacgc |
| SEQ ID NO:21 | P40 | AAV5 | gattactaag caggaagtca aggactttt tgcttgggca aaggtcaatc aggtgccggt gactcacgag tttaaagttc ccagggaatt ggcgggaact aaaggggcgg agaaatctct aaaacgccca ctgggtgacg tcaccaatac tagctataaa agtctggaga agcgggcctg gagcatgagg ctctcatttg ttcccgagac gcctcgcagt tcagacg |
| SEQ ID NO:22 | P40 | AAV6 | ggtgacaaag caggaagtca aagagttctt ccgctgggcg caggatcacg tgaccgaggt ggcgcatgag ttctacgtca gaaagggtgg agccaacaag agacccgccc ccgatgacgc ggataaaagc gagcccaagc gggcctgccc ctcagtcgcg gatccatcga cgtcagacgc |
| SEQ ID NO:23 | P40 | AAV7 | ggtgacgaag caggaagtca aagagttctt ccgctgggcc agtgatcacg tgaccgaggt ggcgcatgag ttctacgtca gaaagggcgg agccagcaaa agacccgccc ccgatgacgc ggatataagc gagcccaagc gggcctgccc ctcagtcgcg gatccatcga cgtcagacgc |
| SEQ ID NO:24 | P40 | AAV8 | ggtgacaaag caggaagtca aagagttctt ccgctgggcc agtgatcacg tgaccgaggt ggcgcatgag ttttacgtca gaaagggcgg agccagcaaa agacccgccc ccgatgacgc ggataaaagc gagcccaagc gggcctgccc ctcagtcgcg gatccatcga cgtcagacgc |

In contrast, the term "non-native AAV serotype promoter sequence" is intended to denote a promoter sequence that does not natively control a rep gene of an AAV and is not natively found within such rep gene. Illustrative, non-limiting examples of non-native AAV serotype promoter sequences include: the AAV1 P5 promoter when used to direct the expression of an AAV2, AAV5, AAV6, or AAV7 rep gene; the AAV2 P5 promoter when used to direct the expression of an AAV1, AAV5, AAV6, or AAV7 rep gene; the AAV5 P5 promoter when used to direct the expression of an AAV1, AAV2, AAV6, or AAV7 rep gene; the AAV6 P5 promoter when used to direct the expression of an AAV1, AAV2, AAV5, or AAV7 rep gene; the AAV7 P5 promoter when used to direct the expression of an AAV1, AAV2, AAV5, or AAV6 rep gene; the AAV1 P40 promoter, when present within an AAV2, AAV5, AAV6, or AAV7 rep gene; the AAV2 P40 promoter, when present within an AAV1, AAV5, AAV6, or AAV7 rep gene; the AAV5 P40 promoter, when present within an AAV1, AAV2, AAV6, or AAV7 rep gene; the AAV6 P40 promoter, when present within an AAV1, AAV2, AAV5, or AAV7 rep gene; the AAV7 P40 promoter, when present within an AAV1, AAV2, AAV5, or AAV6 rep gene, etc.

In one embodiment, one or more of such AAV serotype promoter sequences can be genetically engineered into recombinant AAV helper plasmids that are designed to provide the Rep and Cap proteins to replace or augment the existing P5 or P40 promoters of such plasmids. Such modification is preferably accomplished using well-known methods of recombinant DNA technology.

The identity of the serotype of promoter sequences is indicated herein by denoting the involved promoter (e.g., P5, P40, etc.), the serotype of the rep gene with which it is natively associated, and the name of the vector. Thus, for example, a pAAV-RC2 plasmid that comprises a P5 promoter sequence that is natively associated with AAV2 is denoted as P5(2)-RC2; a pAAV-RC2 plasmid that comprises a P5 promoter sequence that is natively associated with AAV3 is denoted as P5(3)-RC2; a pAAV-RC5 plasmid that comprises a P40 promoter sequence that is natively associated with AAV7 is denoted as P40(7)-RC5; a pAAV-RC2 plasmid that comprises a P5 promoter sequence that is natively associated with AAV3 and a P40 promoter sequence that is natively associated with AAV8 is denoted as P5(3)/P40(8)-RC2; etc.

In one embodiment, the introduced AAV serotype promoter sequence will replace an initially present AAV serotype promoter sequence. In other embodiments, the introduced AAV serotype promoter sequence will be present in addition to such initially present AAV serotype promoter sequence, and will be positioned 5' to, or 3' to, such initially present AAV serotype promoter sequence. The introduced nucleotide sequence may be positioned adjacent to, or apart from, such initially present AAV serotype promoter sequence.

The substitution or addition of one or more of such AAV serotype promoter sequences invention increases rAAV production titers. As used herein, the term "production titer" is intended to denote the amount of concentration of infectious rAAV in a preparation. Such amounts or concentrations are preferably determined by titering the AAV or rAAV in such preparation. The production titers of the rAAV preparations of the present invention are preferably titered after subjecting producing cells (e.g., HEK293 transformed with an rAAV plasmid vector, an AAV helper vector providing Rep and Cap proteins, and an Ad helper vector providing required adenovirus transcription and translation factors) to three rounds of freeze/thawing, followed by sonication to release the rAAV particles. The preparation is then centrifuged. The employed AAV helper vector is localized to the supernatant. An aliquot of the preparation is treated with proteinase K, and the number of AAV genomes is determined. An aliquot of the preparation is infected into HeLa-32C2 cells (which express AAV2 Rep and Cap proteins), and infectious titer is measured using the infectious center assay (ICA) (François, A. et al. (2018) "*Accurate Titration of Infectious AAV Particles Requires Measurement of Biologically Active Vector Genomes and Suitable Controls*," Molec. Ther. Meth. Clin. Develop. 10:223-236) or more preferably, as the median tissue culture infective dose (TCID50) (Zen, Z. et al. (2004) "*Infectious Titer Assay For Adeno-Associated Virus Vectors With Sensitivity Sufficient To Detect Single Infectious Events*," Hum. Gene Ther. 15:709-715).

As used herein, an rAAV production titer is said to be "increased" by the methods of the present invention if the production titer obtained from the use of the methods of the present invention is at least 10% greater, more preferably at least 20% greater, still more preferably at least 30% greater, still more preferably at least 40% greater, still more preferably at least 50% greater, still more preferably at least 60% greater, still more preferably at least 70% greater, still more preferably at least 80% greater, still more preferably at least 90% greater, still more preferably at least 2-fold greater, still more preferably at least 110% greater, still more preferably at least 120% greater, still more preferably at least 130% greater, still more preferably at least 140% greater, still more preferably at least 2.5-fold greater, still more preferably at least 160% greater, still more preferably at least 170% greater, still more preferably at least 180% greater, still more preferably at least 190% greater, and still more preferably at least 3-fold greater than the titer obtained from a similarly conducted production in which the additionally provided ions were not provided.

The rAAV whose production titer may be increased using the methods of the present invention may comprise any transgene cassette that permits the rAAV to be packaged into an rAAV plasmid vector that may be encapsidated within an AAV capsid particle. Without limitation, such transgene cassette(s) may be of human, primate (including chimpanzee, gibbon, gorilla, orangutan, etc.), cercopithecine (including baboon, cynomolgus monkey, velvet monkey, etc.), canine, glirine (including rat, mouse, hamster, guinea pig, etc.), feline, ovine, caprine, or equine origin.

In preferred embodiments, such an rAAV or rAAV plasmid vector will encode a protein (e.g., an enzyme, hormone, antibody, receptor, ligand, etc.), or comprise a transcribed nucleic acid, that is relevant to a genetic or heritable disease or condition, such that it may be used in gene therapy to treat such disease or condition.

The methods of the present invention may be used to increase the production titer of rAAV and rAAV plasmid vectors in cells that have been additionally transfected with:
(1) an AAD helper vector possessing a non-native AAV serotype promoter sequence and capable of expressing proteins or RNA molecules that are not natively provided by such rAAV or rAAV plasmid vectors, but are required for their production. As discussed above, such proteins or RNA molecules include the genes encoding the Rep52 and Rep78 proteins that are required for vector transcription control and replication, and for the packaging of viral genomes into the viral capsule, and cap genes that encode VP capsid proteins required to form infectious particles; and
(2) an Ad helper vector that can provide the non-AAV helper proteins (e.g., E1a, E1b, E2a, VA and E4) or RNA molecules that are not provided by such rAAV or rAAV plasmid vectors, but are required for their production.

In one embodiment for producing the rAAV of the present invention, all of such genes and RNA molecules are provided on the same helper virus (or more preferably, helper vector) so as to comprise, in concert with an rAAV, a double plasmid transfection system. More preferably, however, for producing the rAAV of the present invention, the AAV helper function-providing polynucleotide that provides the required rep and cap genes and such non-native AAV serotype promoter sequences are provided on a vector that is separate from the vector that comprises the non-AAV helper function-providing polynucleotide, so that such vectors or plasmids, in concert with the rAAV, comprise a triple plasmid transfection system.

The invention thus derives in part from the recognition that the production of rAAV may be increased by causing the expression of Rep and Cap proteins to be directed by promoter sequences that are not native promoter sequences. Thus, by modifying a particular rAAV to replace its native P5 and/or P40 AAV serotype promoter sequence(s) with a non-native P5 and/or P40 AAV serotype promoter sequence (or by incorporating a non-native P5 and/or P40 AAV serotype promoter sequence into such rAAV), the methods of the present invention may be employed to increase the production titer of rAAV belonging to any serotype, including the AAV1, AAV2, AAV5, AAV6, AAV7, AAV8, AAV9 and AAV10 serotypes, and including hybrid serotypes (e.g., AAV2/5 and rAAV2/5, which is a hybrid of AAV serotypes 2 and 5 and thus has the trophism of both such serotypes).

The methods of the present invention may be employed to increase the production titers of rAAV that are to be produced using "helper" RNA or proteins provided by an adenovirus, a herpes simplex virus, a cytomegalovirus, a vaccinia virus or a papillomavirus.

The methods of the present invention may be employed to increase the production titers of rAAV produced by cells in adherent monolayer culture or in suspension culture, and may be used with any method capable of producing rAAV. Preferably, however, rAAV is produced by transfecting baby hamster kidney (BHK) cells, or more preferably, human embryonic kidney (HEK) cells grown in tissue culture with the plasmid vectors described above. The BHK cell line BHK-21 (ATCC CCL-10), which lacks endogenous retroviruses is a preferred BHK cell line. The HEK cell line HEK293 (ATCC CRL-1573) and its derivatives, such as HEK293T (ATCC CRL-3216, which is a highly transfectable derivative of the HEK293 cell line into which the temperature-sensitive gene for SV40 T-antigen was inserted) or HEK293T/17 (ATCC® CRL-11268, which was selected for its ease of transfection) are particularly preferred. The HEK293T/17 SF cell line (ATCC ACS-4500) is a derivative of the 293T/17 cell line (ATCC CRL-11268), adapted to serum-free medium and suspension, and may be employed if desired.

The preferred base medium of the present invention for culturing such cells is Eagle's Minimum Essential Medium (ATCC Catalog No. 30-2003) or Dulbecco's Modified Eagle's Medium (DMEM; Mediatech, Manassas, Va.). Fetal bovine serum (e.g., FBS; HyClone Laboratories, South Logan, Utah) is added to a final concentration of 10% in order to make the complete growth medium. Eagle's Minimum Essential Medium and Dulbecco's Modified Eagle's Medium are complex media that contain amino acids, vitamins, and optionally glucose, in addition to various inorganic salts. The media differ in that Dulbecco's modified Eagle's medium contains approximately four times as much of the vitamins and amino acids present in the original formula of Eagle's Minimum Essential Medium, and two to four times as much glucose. Additionally, it contains iron in the form of ferric sulfate and phenol red for pH indication (Yao, T et al. (2017) "*Animal-Cell Culture Media: History, Characteristics, And Current Issues*," Reproduc. Med. Biol. 16(2): 99-117).

Cells to be used for such transfection are preferably passaged twice weekly to maintain them in exponential growth phase. For small-scale transfections, an aliquot of, for example, $1\times10^6$ HEK293 or BHK cells per well on a multi-well plate, or $1.5\times10^7$ HEK293 cells per 15-cm dish, may be employed. For large-scale production HEK293 or BHK cells may be collected from multiple confluent 15-cm plates, and split into two 10-layer cell stacks (Corning, Corning, N.Y.) containing 1 liter of complete culturing medium. In one embodiment, such cells are grown for 4 days in such medium before transfection. The day before transfection, the two cell stacks may be trypsinized and the cells (e.g., approximately $6\times10^8$ cells) may be resuspended in 200 ml of medium. Preferably, the cells are allowed to attach for 24 hours before transfection. Confluency of the cell stacks may be monitored using a Diaphot inverted microscope (Nikon, Melville, N.Y.) from which the phase-contrast hardware had been removed in order to accommodate the cell stack on the microscope stage.

In particular, the present invention thus provides a method for increasing the production titer of a recombinantly-modified adeno-associated virus (rAAV) that comprises a transgene cassette, wherein the method comprises culturing cells that have been transfected with:
 (1) the rAAV;
 (2) a recombinantly-modified adeno-associated virus (AAV) helper vector that comprises an AAV helper function-providing polynucleotide, wherein such polynucleotide comprises a non-native AAV serotype P5 or P40 promoter sequence in replacement of, or in addition to, a native AAV serotype promoter sequence; and
 (3) a vector that comprises a non-AAV helper function-providing polynucleotide;
wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

The present invention further provides a method for increasing the production titer of a recombinantly-modified adeno-associated virus (rAAV) that comprises a transgene cassette, wherein the method comprises culturing cells that have been transfected with:
 (1) the rAAV; and
 (2) a recombinantly-modified adeno-associated virus (AAV) helper vector that comprises:
  (a) an AAV helper function-providing polynucleotide, wherein such polynucleotide comprises a non-native AAV serotype P5 or P40 promoter sequence in replacement of, or in addition to, a native AAV serotype promoter sequence; and
  (b) a non-AAV helper function-providing polynucleotide;
wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

In preferred embodiments, the transgene cassette of such rAAV encodes a protein, or comprises a transcribed nucleic acid, that is therapeutic for a genetic or heritable disease or condition.

II. Pharmaceutical Compositions of the Present Invention

The invention additionally includes pharmaceutical compositions that comprise a pharmaceutically acceptable preparation of rAAV produced in accordance with the methods of the present invention, and a pharmaceutically acceptable carrier. The rAAV of such pharmaceutical compositions comprises a transgene cassette that encodes a protein, or comprises a transcribed nucleic acid, that is therapeutic for a genetic or heritable disease or condition, and is present in such pharmaceutical composition in an amount effective to ("effective amount")

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Suitable pharmaceutical excipients are described in U.S. Pat. Nos. 8,852,607; 8,192,975; 6,764,845; 6,759,050; and 7,598,070.

Generally, the ingredients of compositions of the invention are supplied either separately or mixed together in unit dosage form, for example, as a dry lyophilized powder or water-free concentrate, or as an aqueous solution in a hermetically sealed container such as a vial, an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline, or other diluent can be provided so that the ingredients may be mixed prior to administration.

The invention also provides a pharmaceutical pack or kit comprising one or more containers such pharmaceutical composition. Optionally associated with such container(s) can be a notice in the form prescribed by a governmental agency regulating the manufacture, use or sale of pharmaceuticals or biological products, which notice reflects approval by the agency of manufacture, use or sale for human administration.

The rAAV of such pharmaceutical compositions is preferably packaged in a hermetically sealed container, such as a vial, an ampoule or sachette indicating the quantity of the molecule, and optionally including instructions for use. In one embodiment, the rAAV of such kit is supplied as a dry sterilized lyophilized powder or water-free concentrate in a hermetically sealed container and can be reconstituted, e.g., with water, saline, or other diluent to the appropriate concentration for administration to a subject. The lyophilized material should be stored at between 2° C. and 8° C. in their original container and the material should be administered within 12 hours, preferably within 6 hours, within 5 hours, within 3 hours, or within 1 hour after being reconstituted. In another embodiment, the rAAV of such kit is supplied as an aqueous solution in a hermetically sealed container and can be diluted, e.g., with water, saline, or other diluent, to the appropriate concentration for administration to a subject. The kit can further comprise one or more other prophylactic and/or therapeutic agents useful for the treatment of the disease or condition, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

III. Uses of the Invention

The methods of the present invention may be used to facilitate the production of rAAV, and may particularly be used to facilitate the production of rAAV that comprise transgene cassettes that encode a protein (e.g., an enzyme, hormone, antibody, receptor, ligand, etc.), or of rAAV that comprise a transcribed nucleic acid, that is relevant to a genetic or heritable disease or condition, such that it may be used in gene therapy to treat such disease or condition. Examples of such diseases and conditions include: achromatopsia (ACHM); alpha-1 antitrypsin (AAT) deficiency; Alzheimer's Disease; aromatic L-amino acid decarboxylase (AADC) deficiency; choroideremia (CHM); cancer; Duchenne muscular dystrophy; dysferlin deficiency; follistatin gene deficiency (BMDSIBM); hemophilia A; hemophilia B; hepatitis A; hepatitis B; hepatitis C; Huntington's disease; idiopathic Parkinson's disease; late-infantile neuronal ceroid lipofuscinosis (LINCL, an infantile form of Batten disease); Leber congenital amaurosis (LCA); Leber's hereditary optic neuropathy (LHON); limb girdle muscular dystrophy 1B (LGMD1B); limb girdle muscular dystrophy 1C (LGMD1C); limb girdle muscular dystrophy 2A (LGMD2A); limb girdle muscular dystrophy 2B (LGMD2B); limb girdle muscular dystrophy 2I (LGMD2I); limb girdle muscular dystrophy 2L (LGMD2L); lipoprotein lipase (LPL) deficiency; metachromatic leukodystrophy; neurological disability; neuromotor deficit; neuroskeletal impairment; Parkinson's disease; rheumatoid arthritis; Sanfilippo A syndrome; spinal muscular atrophy (SMA); X-linked retinoschisis (XLRS); α-sarcoglycan deficiency (LGMD2D); β-sarcoglycan deficiency (LGMD2E); γ-sarcoglycan deficiency (LGMD2C) and δ-sarcoglycan deficiency (LGMD2F).

IV. Embodiments of the Invention

The invention concerns a recombinantly-modified adeno-associated virus (AAV) helper vector that comprises an AAV helper function-providing polynucleotide, and uses and compositions thereof. It is particularly directed to the following embodiments E1-E16:

E1. A recombinantly-modified adeno-associated virus (AAV) helper vector that comprises an AAV helper function-providing polynucleotide, wherein the polynucleotide comprises a non-native AAV serotype P5 or P40 promoter sequence.

E2. The recombinantly-modified adeno-associated virus (AAV) helper vector of E1, wherein the AAV helper function-providing polynucleotide vector comprises a non-native AAV serotype P5 promoter sequence.

E3. The recombinantly-modified adeno-associated virus (AAV) helper vector of any one of E1 or E2, wherein the AAV helper function-providing polynucleotide vector comprises a non-native AAV serotype P40 promoter sequence.

E4. The recombinantly-modified adeno-associated virus (AAV) helper vector of any one of E1-E3, wherein the vector is a plasmid vector.

E5. The recombinantly-modified adeno-associated virus (AAV) helper vector of E1, wherein the non-native AAV serotype P5 or P40 promoter sequence replaces a native AAV serotype promoter sequence.

E6. The recombinantly-modified adeno-associated virus (AAV) helper vector of any one of E1-E5, wherein the vector additionally comprises a non-AAV helper function-providing polynucleotide.

E7. A method for increasing the production titer of a recombinantly-modified adeno-associated virus (rAAV) that comprises a transgene cassette, wherein the method comprises culturing cells that have been transfected with:
(1) the rAAV;
(2) the recombinantly-modified adeno-associated virus (AAV) helper vector of E6;

wherein the culturing is conducted in a culture medium under conditions sufficient to permit the production of the rAAV and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

E8. A method for increasing the production titer of a recombinantly-modified adeno-associated virus (rAAV) that comprises a transgene cassette, wherein the method comprises culturing cells that have been transfected with:
(1) the rAAV;
(2) the recombinantly-modified adeno-associated virus (AAV) helper vector of any one of E1-E6; and
(3) an additional vector, especially a plasmid vector, that comprises a non-AAV helper function-providing polynucleotide;
wherein the culturing is conducted in a culture medium under conditions sufficient to permit the production of the rAAV, and wherein the presence of the non-native AAV serotype P5 or P40 promoter sequence causes the cells to produce the rAAV at an increased production titer relative to that which would be attained if the AAV helper function-providing polynucleotide contained native serotype P5 and P40 promoters.

E9. The method of any one of E7-E8, wherein:
(A) the AAV helper function-providing polynucleotide of the vector encodes an AAV1 Cap protein, and the non-native AAV serotype promoter sequence is a promoter sequence of an AAV of serotype AAV3, AAV4, AAV5, AAV6, AAV7 or AAV8, or a hybrid of one or more of the serotypes;
(B) the AAV helper function-providing polynucleotide of the vector encodes an AAV2 Cap protein, and the non-native AAV serotype promoter sequence is a promoter sequence of an AAV of serotype AAV1, AAV3, AAV4, AAV5, AAV6, AAV7 or AAV8, or a hybrid of one or more of the serotypes;
(C) the AAV helper function-providing polynucleotide of the vector encodes an AAV3 Cap protein, and the non-native AAV serotype promoter sequence is a promoter sequence of an AAV of serotype AAV1, AAV4, AAV5, AAV6, AAV7 or AAV8, or a hybrid of one or more of the serotypes;
(D) the AAV helper function-providing polynucleotide of the vector encodes an AAV4 Cap protein, and the non-native AAV serotype promoter sequence is a promoter sequence of an AAV of serotype AAV1, AAV3, AAV5, AAV6, AAV7 or AAV8, or a hybrid of one or more of the serotypes;
(E) the AAV helper function-providing polynucleotide of the vector encodes an AAV5 Cap protein, and the non-native AAV serotype promoter sequence is a promoter sequence of an AAV of serotype AAV1, AAV3, AAV4, AAV6, AAV7 or AAV8, or a hybrid of one or more of the serotypes;
(F) the AAV helper function-providing polynucleotide of the vector encodes an AAV6 Cap protein, and the non-native AAV serotype promoter sequence is a promoter sequence of an AAV of serotype AAV1, AAV3, AAV4, AAV5, AAV7 or AAV8, or a hybrid of one or more of the serotypes;
(G) the AAV helper function-providing polynucleotide of the vector encodes an AAV7 Cap protein, and the non-native AAV serotype promoter sequence is a promoter sequence of an AAV of serotype AAV1, AAV3, AAV4, AAV5, AAV6 or AAV8, or a hybrid of one or more of the serotypes; or
(H) the AAV helper function-providing polynucleotide of the vector encodes an AAV8 Cap protein, and the non-native AAV serotype promoter sequence is a promoter sequence of an AAV of serotype AAV1, AAV3, AAV4, AAV5, AAV6 or AAV7, or a hybrid of one or more of the serotypes.

E10. The method of any one of E7-E9, wherein the cells are human embryonic kidney cells, baby hamster kidney cells or sf9 insect cells.

E11. The method of E10, wherein the cells are HEK293 human embryonic kidney cells.

E12. The method of E10, wherein the cells are BHK21 baby hamster kidney cells.

E13. The method of any one of E7-E12, wherein the transgene cassette encodes a protein, or comprises a transcribed nucleic acid, that is therapeutic for a genetic or heritable disease or condition.

E14. A preparation of the recombinantly-modified adeno-associated virus (rAAV) produced by the method of E13.

E15. A pharmaceutical composition that comprises the recombinantly-modified adeno-associated virus (rAAV) produced by the method of E13, and a pharmaceutically acceptable carrier.

E16. The preparation of recombinantly-modified adeno-associated virus (rAAV) of E14, or the pharmaceutical composition of E15, for use in the treatment of the genetic or heritable disease or condition.

EXAMPLES

Having now generally described the invention, the same will be more readily understood through reference to the following examples, which are provided by way of illustration and are not intended to be limiting of the present invention unless specified.

Example 1

Comparison of rAAV Production Titers by Cells Transfected with AAV RC2 Helper Plasmid Vectors Having a Non-Native AAV Serotype P5 Promoter Sequence In order to demonstrate the ability of non-native AAV serotype promoter sequences to affect the production titer of rAAV, derivatives of AAV helper plasmid AAV RC2 (having an AAV2 rep gene and a cap gene that encodes Cap protein of the AAV2 serotype) were constructed that comprised a non-native AAV serotype promoter sequence (FIG. 11) in lieu of the native AAV2 serotype P5 promoter of such plasmid (FIG. 12A; downward striped rectangle). The P19 and P40 promoters of the constructs were not changed, and thus were both native AAV2 serotype promoter sequences (FIG. 12A; solid black rectangles).

The following constructs were employed; the sequences of the promoter regions are shown in Table 1:
(1) Parent-RC2—pAAV-RC2 (SEQ ID NO:2), which contains the AAV2 rep gene and a partial portion of the full AAV2 serotype P5 promoter sequence (SEQ ID NO:10), and the AAV2 cap gene, whose expression is controlled by a native AAV2 P40 promoter sequence (SEQ ID NO:18);

(2) P5(1)-RC2—a derivative of plasmid vector pAAV-RC2 in which native AAV serotype P5 promoter sequences had been replaced with the P5 promoter sequences of AAV serotype 1 (SEQ ID NO:9);
(3) P5(2)-RC2—a derivative of plasmid vector pAAV-RC2 in which the partial AAV2 serotype P5 promoter sequences of Parent-RC2 had been replaced with the full-length P5 promoter sequences of AAV serotype 2 (SEQ ID NO:10);
(4) P5(3)-RC2—a derivative of plasmid vector pAAV-RC2 in which native AAV2 serotype P5 promoter sequences had been replaced with the P5 promoter sequences of AAV serotype 3 (SEQ ID NO:11);
(5) P5(4)-RC2—a derivative of plasmid vector pAAV-RC2 in which native AAV2 serotype P5 promoter sequences had been replaced with the P5 promoter sequences of AAV serotype 4 (SEQ ID NO:12);
(6) P5(5)-RC2—a derivative of plasmid vector pAAV-RC2 in which native AAV2 serotype P5 promoter sequences had been replaced with the P5 promoter sequences of AAV serotype 5 (SEQ ID NO:13);
(7) P5(6)-RC2—a derivative of plasmid vector pAAV-RC2 in which native AAV2 serotype P5 promoter sequences had been replaced with the P5 promoter sequences of AAV serotype 6 (SEQ ID NO:14);
(8) P5(7)-RC2—a derivative of plasmid vector pAAV-RC2 in which native AAV2 serotype P5 promoter sequences had been replaced with the P5 promoter sequences of AAV serotype 7 (SEQ ID NO:15); and
(9) P5(8)-RC2—a derivative of plasmid vector pAAV-RC2 in which native AAV2 serotype P5 promoter sequences had been replaced with the P5 promoter sequences of AAV serotype 8 (SEQ ID NO:16).

FIG. 12B shows the production titers of rAAV obtained using such AAV helper plasmid vectors. The production titers of rAAV were obtained using a triple plasmid transfection system with an rAAV (pGOI; BBa K404119), and an Ad helper plasmid (pHelper) that provided the required adenoviral functions. Plasmid pGOI is an rAAV plasmid vector that comprises, in the 5' to 3' direction, a 5' ITR, a CMV promoter, a β-globin intron, a polynucleotide encoding the yellow fluorescent protein mVenus (Nagai, T. et al. (2002) "*A Variant Of Yellow Fluorescent Protein With Fast And Efficient Maturation For Cell-Biological Applications*," Nat. Biotechnol. 20(1):87-90), the polyA domain of human growth hormone and a 3' ITR. FIG. 12B reveals that the serotype of the P5 promoter affects rAAV production titers, and indicates that replacing the native AAV2 P5 promoter of the plasmid vector pAAV-RC2 with an AAV5 serotype P5 promoter greatly decreased rAAV production titer, whereas replacing the native AAV2 P5 promoter of the plasmid vector pAAV-RC2 with a P5 promoter of AAV serotype 1, 3, 5, 7 or 8 greatly increased rAAV production titer.

Example 2

Comparison of rAAV Production Titers by Cells Transfected with AAV RC2 Helper Plasmid Vectors Having a Non-Native AAV Serotype P40 Promoter Sequence In order to further demonstrate the ability of non-native AAV serotype promoter sequences to affect the production titer of rAAV, derivatives of AAV helper plasmid AAV RC2 (having an AAV2 rep gene and a cap gene that encodes Cap protein of the AAV2 serotype) were constructed that comprised a non-native AAV serotype promoter sequence (FIG. 11) in lieu of the native serotype P40 promoter of such plasmid (FIG. 13A; upward striped rectangle). The P5 and P19 promoters of the constructs were not changed, and thus were both native AAV2 serotype promoter sequences (FIG. 13A; solid black rectangles).

The following constructs were employed; the sequences of the promoter regions are shown in Table 1:
(1) Parent-RC2—pAAV-RC2 (SEQ ID NO:2), which contains the AAV2 rep gene and a partial portion of the full AAV2 serotype P5 promoter sequence (SEQ ID NO:10), and the AAV2 cap gene, whose expression is controlled by a native AAV2 P40 promoter sequence (SEQ ID NO:18);
(2) P40(1)-RC2—a derivative of plasmid vector pAAV-RC2 in which native AAV2 serotype P40 promoter sequences had been replaced with the P40 promoter sequences of AAV serotype 1 (SEQ ID NO:17);
(3) P40(2)-RC2—a derivative of plasmid vector pAAV-RC2 in which the AAV2 serotype P40 promoter sequences of Parent-RC2 had been replaced with the P40 promoter sequences of AAV serotype 2 (SEQ ID NO:18);
(4) P40(3)-RC2—a derivative of plasmid vector pAAV-RC2 in which native AAV2 serotype P40 promoter sequences had been replaced with the P40 promoter sequences of AAV serotype 3 (SEQ ID NO:19);
(5) P40(4)-RC2—a derivative of plasmid vector pAAV-RC2 in which native AAV2 serotype P40 promoter sequences had been replaced with the P40 promoter sequences of AAV serotype 4 (SEQ ID NO:20);
(6) P40(5)-RC2—a derivative of plasmid vector pAAV-RC2 in which native AAV2 serotype P40 promoter sequences had been replaced with the P40 promoter sequences of AAV serotype 5 (SEQ ID NO:21);
(7) P40(6)-RC2—a derivative of plasmid vector pAAV-RC2 in which native AAV2 serotype P40 promoter sequences had been replaced with the P40 promoter sequences of AAV serotype 6 (SEQ ID NO:22);
(8) P40(7)-RC2—a derivative of plasmid vector pAAV-RC2 in which native AAV2 serotype P40 promoter sequences had been replaced with the P40 promoter sequences of AAV serotype 7 (SEQ ID NO:23); and
(9) P40(8)-RC2—a derivative of plasmid vector pAAV-RC2 in which native AAV2 serotype P40 promoter sequences had been replaced with the P40 promoter sequences of AAV serotype 8 (SEQ ID NO:24).

FIG. 13B shows the production titers of rAAV obtained using such AAV helper plasmid vectors. Production titers of rAAV were obtained essentially as described in Example 1. The results of the investigation reveal that the serotype of the P40 promoter also affects rAAV production titers, and indicate that replacing the native AAV2 P40 promoter of the plasmid vector pAAV-RC2 with an AAV5 serotype P40 promoter greatly decreased rAAV production titer, whereas replacing the native AAV2 P40 promoter of the plasmid vector pAAV-RC2 with an AAV1 serotype P40 promoter or with an AAV8 serotype P40 promoter greatly increased rAAV production titer.

Example 3

Comparison of rAAV Production Titers by Cells Transfected with AAV RC2 Helper Plasmid Vectors Having Non-Native AAV Serotype P5 and P40 Promoter Sequences In order to further demonstrate the ability of non-native AAV serotype promoter sequences to affect the production titer of rAAV, derivatives of AAV helper plasmid AAV RC2 (having an AAV2 rep gene and a cap gene that encodes Cap protein of the AAV2 serotype) were constructed that comprised non-native AAV serotype promoter sequences (FIG. 11) in lieu of the native AAV2 serotype P5 (FIG. 14A; downward striped rectangle) and P40 (FIG. 14A; upward striped rectangle) promoters of such plasmid. The AAV2 P19 promoter of the constructs were not changed, and thus was the native AAV2 serotype promoter sequence (FIG. 14A; solid black rectangle).

The following constructs were employed; the sequences of the promoter regions are shown in Table 1:
(1) Parent-RC2—pAAV-RC2 (SEQ ID NO:2), which contains the AAV2 rep gene and a partial portion of the full AAV2 serotype P5 promoter sequence (SEQ ID NO:10), and the AAV2 cap gene, whose expression is controlled by a native AAV2 P40 promoter sequence (SEQ ID NO:18);
(2) P5(2)-RC2—a derivative of plasmid vector pAAV-RC2 in which the partial AAV2 serotype P5 promoter sequences of Parent-RC2 had been replaced with the full-length P5 promoter sequences of AAV serotype 2 (SEQ ID NO:10);
(3) P5(3)-RC2—a derivative of plasmid vector pAAV-RC2 in which native AAV2 serotype P5 promoter sequences had been replaced with the P5 promoter sequence of AAV3 (SEQ ID NO:11);
(4) P5(5)-RC2—a derivative of plasmid vector pAAV-RC2 in which native AAV2 serotype P5 promoter sequences had been replaced with the P5 promoter sequence of AAV5 (SEQ ID NO:13);
(5) P40(1)-RC2—a derivative of plasmid vector pAAV-RC2 in which native AAV2 serotype P40 promoter sequences had been replaced with the P40 promoter sequence of AAV1 (SEQ ID NO:17);
(6) P5(2)/P40(1)-RC2—a derivative of plasmid vector pAAV-RC2 in which native AAV2 serotype P5 promoter sequences had been replaced with the P5 promoter sequence of AAV2 (SEQ ID NO:10) and in which native P40 promoter sequences had been replaced with the P40 promoter sequence of AAV1 (SEQ ID NO:17);
(7) P5(3)/P40(1)-RC2—a derivative of plasmid vector pAAV-RC2 in which native AAV2 serotype P5 promoter sequences had been replaced with the P5 promoter sequence of AAV3 (SEQ ID NO:11) and in which native P40 promoter sequences had been replaced with the P40 promoter sequence of AAV1 (SEQ ID NO:17); and
(8) P5(5)/P40(1)-RC2—a derivative of plasmid vector pAAV-RC2 in which native AAV2 serotype P5 promoter sequences had been replaced with the P5 promoter sequence of AAV5 (SEQ ID NO:13) and in which native P40 promoter sequences had been replaced with the P40 promoter sequence of AAV1 (SEQ ID NO:17).

Production titers of rAAV were obtained essentially as described in Example 1. FIG. 14B shows the production titers of rAAV obtained using such AAV helper plasmid vectors. As shown in FIG. 14B, the replacement of the native P5 and P40 promoters of pAAV-RC2 with the P5 promoter sequence of AAV3 or AAV5 and the P40 promoter sequence of AAV1 synergistically increased rAAV production titers.

Example 4

Comparison of rAAV Production Titers by Cells Transfected with AAV RC6 Helper Plasmid Vectors Having Non-Native AAV Serotype P5 and P40 Promoter Sequences In order to further demonstrate the ability of non-native AAV serotype promoter sequences to affect the production titer of rAAV, derivatives of AAV helper plasmid AAV RC6 (having an AAV2 rep gene and a cap gene that encodes Cap protein of the AAV6 serotype) were constructed that comprised non-native AAV serotype promoter sequences (FIG. 11) in lieu of the native AAV2 serotype P5 (FIG. 15A; downward striped rectangle) and P40 (FIG. 15A; downward striped rectangle) promoters of such plasmid. The AAV2 P19 promoter of the constructs were not changed, and thus was the native AAV2 serotype promoter sequence (FIG. 15A; solid black rectangle).

The following constructions were employed; the sequences of the promoter regions are shown in Table 1:
(1) Parent-RC6—pAAV-RC6 (SEQ ID NO:4), which contains the AAV2 rep gene and its native AAV2 serotype P5 promoter sequence (SEQ ID NO:10), and the AAV6 cap gene, whose expression is controlled by a native AAV2 P40 promoter sequence (SEQ ID NO:18);
(2) P5(1)-RC6—a derivative of plasmid vector pAAV-RC6 in which native AAV2 serotype P5 promoter sequences had been replaced with the P5 promoter sequence of AAV1 (SEQ ID NO:9);
(3) P5(2)-RC6—a derivative of plasmid vector pAAV-RC6 in which native AAV2 serotype P5 promoter sequences had been replaced with the P5 promoter sequence of AAV2 (SEQ ID NO:10);
(4) P5(3)-RC6—a derivative of plasmid vector pAAV-RC6 in which native AAV2 serotype P5 promoter sequences had been replaced with the P5 promoter sequence of AAV3 (SEQ ID NO:11);
(5) P5(7)-RC6—a derivative of plasmid vector pAAV-RC6 in which native AAV2 serotype P5 promoter sequences had been replaced with the P5 promoter sequence of AAV7 (SEQ ID NO:15); and
(6) P5(8)-RC6—a derivative of plasmid vector pAAV-RC6 in which native AAV2 serotype P5 promoter sequences had been replaced with the P5 promoter sequence of AAV8 (SEQ ID NO:16).

FIG. 15B shows the production titers of rAAV obtained using such AAV helper plasmid vectors. Production titers of rAAV were obtained essentially as described in Example 1.

The results of the investigation are shown in FIGS. 15B and 15C, and reveal that the production titers of rAAV obtained using such AAV helper plasmid vectors. As shown in such Figures, the replacement of the native P5 and P40 promoters of pAAV-RC6 with the P5 promoter sequence of AAV serotype 1, 2, 3, 7 or 8 increased rAAV production titers.

Example 5

Comparison of rAAV Production Titers by Cells Transfected with AAV RC1, AAV RC5 or AAV RC7 Helper Plasmid Vectors Having Non-Native AAV Serotype P5 and P40 Promoter Sequences In order to further demonstrate the ability of non-native AAV serotype promoter sequences to affect the production titer of rAAV, derivatives of AAV helper plasmid AAV RC1 (having an AAV2 rep gene and a cap gene that encodes Cap protein of the AAV1 serotype), derivatives of AAV helper plasmid AAV RC5 (having an AAV2 rep gene and a cap gene that encodes Cap protein of the AAV5 serotype) and derivatives of AAV helper plasmid AAV RC7 (having an AAV2 rep gene and a cap gene that encodes Cap protein of the AAV7 serotype) were constructed that comprised non-native AAV serotype promoter sequences (FIG. 11) in lieu of the native AAV2 serotype P5 (FIG. 16A; downward striped rectangle) and/or P40 (FIG. 16A; upward striped rectangle) promoter sequences of such plasmids.

The following constructions were employed; the sequences of the promoter regions are shown in Table 1:
(1) Parent-RC1—pAAV-RC1 (SEQ ID NO:1), which contains the AAV2 rep gene and its native AAV2 serotype P5 promoter sequence (SEQ ID NO:10), and the AAV1 cap gene, whose expression is controlled by a native AAV2 P40 promoter sequence (SEQ ID NO:18);
(2) Parent-RC5—pAAV-RC5 (SEQ ID NO:3), which contains the AAV2 rep gene and its native AAV2 serotype P5 promoter sequence (SEQ ID NO:10), and the AAV5 cap gene, whose expression is controlled by a native AAV2 P40 promoter sequence (SEQ ID NO:18);
(3) Parent-RC7—pAAV-RC7 (SEQ ID NO:5), which contains the AAV2 rep gene and its native AAV2 serotype P5 promoter sequence (SEQ ID NO:10), and the AAV7 cap gene, whose expression is controlled by a native AAV2 P40 promoter sequence (SEQ ID NO:18);
(4) P5(2)-RC1—a derivative of plasmid vector pAAV-RC1 in which native AAV1 serotype P5 promoter sequences had been replaced with the P5 promoter sequence of AAV2 (SEQ ID NO:10);
(5) P5(7)-RC1—a derivative of plasmid vector pAAV-RC1 in which native AAV1 serotype P5 promoter sequences had been replaced with the P5 promoter sequence of AAV7 (SEQ ID NO:15);
(6) P5(8)-RC1—a derivative of plasmid vector pAAV-RC1 in which native AAV1 serotype P5 promoter sequences had been replaced with the P5 promoter sequence of AAV8 (SEQ ID NO:16);
(7) P5(7)-RC5—a derivative of plasmid vector pAAV-RC5 in which native AAV5 serotype P5 promoter sequences had been replaced with the P5 promoter sequence of AAV7 (SEQ ID NO:15);
(8) P5(2)-RC7—a derivative of plasmid vector pAAV-RC7 in which native AAV7 serotype P5 promoter sequences had been replaced with the P5 promoter sequence of AAV2 (SEQ ID NO:10).
(9) P5(7)-RC7—a derivative of plasmid vector pAAV-RC7 in which native AAV7 serotype P5 promoter sequences had been replaced with the P5 promoter sequence of AAV7 (SEQ ID NO:15); and
(10) P5(8)-RC7—a derivative of plasmid vector pAAV-RC7 in which native AAV7 serotype P5 promoter sequences had been replaced with the P5 promoter sequence of AAV8 (SEQ ID NO:16).

Production titers of rAAV were obtained essentially as described in Example 1. The results of the investigation are shown in FIG. 16B, and reveals that the replacement of the native P5 promoter sequences of pAAV-RC1, pAAV-RC5, and pAAV-RC7 with P5 promoter sequence of AAV serotype 2, 7 or 8 increased rAAV production titers.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A recombinantly-modified adeno-associated virus (AAV) helper vector that comprises an AAV helper function-providing polynucleotide, wherein said polynucleotide comprises a non-native AAV serotype P5 or P40 promoter sequence.

2. The recombinantly-modified adeno-associated virus (AAV) helper vector of claim 1, wherein said AAV helper function-providing polynucleotide vector comprises a non-native AAV serotype P5 promoter sequence.

3. The recombinantly-modified adeno-associated virus (AAV) helper vector of claim 1, wherein said AAV helper function-providing polynucleotide vector comprises a non-native AAV serotype P40 promoter sequence.

4. The recombinantly-modified adeno-associated virus (AAV) helper vector of claim 1, wherein said vector is a plasmid vector.

5. The recombinantly-modified adeno-associated virus (AAV) helper vector of claim 1, wherein said non-native AAV serotype P5 or P40 promoter sequence replaces a native AAV serotype promoter sequence.

6. The recombinantly-modified adeno-associated virus (AAV) helper vector of claim 1, wherein said vector additionally comprises a non-AAV helper function-providing polynucleotide.

7. A method for increasing the production titer of a recombinantly-modified adeno-associated virus (rAAV) that comprises a transgene cassette, wherein said method comprises culturing cells that have been transfected with:
 (1) said rAAV; and
 (2) the recombinantly-modified adeno-associated virus (AAV) helper vector of claim 6;
wherein said culturing is conducted in a culture medium under conditions sufficient to permit the production of said rAAV and wherein the presence of said non-native AAV serotype P5 or P40 promoter sequence causes said cells to produce said rAAV at an increased production titer relative to that which would be attained if said AAV helper function-providing polynucleotide contained native serotype P5 and P40 promoters.

8. The method of claim 7, wherein said transgene cassette encodes a protein, or comprises a polynucleotide domain that is transcribed into an RNA molecule, wherein said protein or said RNA molecule is therapeutic for a genetic or heritable disease or condition.

9. The method of claim 7, wherein said cells are human embryonic kidney cells, baby hamster kidney cells or sf9 insect cells.

10. The method of claim 9, wherein said cells are HEK293 human embryonic kidney cells.

11. The method of claim 9, wherein said cells are BHK21 baby hamster kidney cells.

12. A method for increasing the production titer of a recombinantly-modified adeno-associated virus (rAAV) that comprises a transgene cassette, wherein said method comprises culturing cells that have been transfected with:
 (1) said rAAV;
 (2) the recombinantly-modified adeno-associated virus (AAV) helper vector of claim 1; and
 (3) an additional vector that comprises a non-AAV helper function-providing polynucleotide;
wherein said culturing is conducted in a culture medium under conditions sufficient to permit the production of said rAAV and wherein the presence of said non-native AAV serotype P5 or P40 promoter sequence causes said cells to produce said rAAV at an increased production titer relative to that which would be attained if said AAV helper function-providing polynucleotide contained native serotype P5 and P40 promoters.

13. The method of claim 12, wherein said transgene cassette encodes a protein, or comprises a transcribed nucleic acid, that is therapeutic for a genetic or heritable disease or condition.

14. The method of claim 12, wherein said cells are human embryonic kidney cells, baby hamster kidney cells or sf9 insect cells.

15. The method of claim 14, wherein said cells are HEK293 human embryonic kidney cells.

16. The method of claim 14, wherein said cells are BHK21 baby hamster kidney cells.

* * * * *

SEQUENCE LISTING

```
<160> NUMBER OF SEQ ID NOS: 24

<210> SEQ ID NO 1
<211> LENGTH: 7431
<212> TYPE: DNA
<213> ORGANISM: Artificial Sequence
<220> FEATURE:
<223> OTHER INFORMATION: Coding Strand of Plasmid pAAV-RC1

<400> SEQUENCE: 1
catggttttg ggacgtttcc tgagtcagat tcgcgaaaaa ctgattcaga gaatttaccg      60
cgggatcgag ccgactttgc caaactggtt cgcggtcaca aagaccagaa atggcgccgg     120
aggcgggaac aaggtggtgg atgagtgcta catccccaat tacttgctcc ccaaaaccca     180
gcctgagctc cagtgggcgt ggactaatat ggaacagtat ttaagcgcct gtttgaatct     240
cacggagcgt aaacggttgg tggcgcagca tctgacgcac gtgtcgcaga cgcaggagca     300
gaacaaagag aatcagaatc ccaattctga tgcgccggtg atcagatcaa aaacttcagc     360
caggtacatg gagctggtcg ggtggctcgt ggacaagggg attacctcgg agaagcagtg     420
gatccaggag gaccaggcct catacatctc cttcaatgcg gcctccaact cgcggtccca     480
aatcaaggct gccttggaca atgcgggaaa gattatgagc ctgactaaaa ccgcccccga     540
ctacctggtg ggccagcagc ccgtggagga catttccagc aatcggattt ataaaatttt     600
ggaactaaac gggtacgatc cccaatatgc ggcttccgtc tttctgggat gggccacgaa     660
aaagttcggc aagaggaaca ccatctggct gtttgggcct gcaactaccg gaagaccaa     720
```

```
catcgcggag gccatagccc acactgtgcc cttctacggg tgcgtaaact ggaccaatga    780
gaactttccc ttcaacgact gtgtcgacaa gatggtgatc tggtgggagg aggggaagat    840
gaccgccaag gtcgtggagt cggccaaagc cattctcgga ggaagcaagg tgcgcgtgga    900
ccagaaatgc aagtcctcgg cccagataga cccgactccc gtgatcgtca cctccaacac    960
caacatgtgc gccgtgattg acgggaactc aacgaccttc gaacaccagc agccgttgca   1020
agaccggatg ttcaaatttg aactcacccg ccgtctggat catgactttg gaaggtcac    1080
caagcaggaa gtcaaagact ttttccggtg ggcaaaggat cacgtggttg aggtggagca   1140
tgaattctac gtcaaaaagg gtggagccaa gaaaagaccc gcccccagtg acgcagatat   1200
aagtgagccc aaacgggtgc gcgagtcagt tgcgcagcca tcgacgtcag acgcggaagc   1260
ttcgatcaac tacgcagaca ggtaccaaaa caaatgttct cgtcacgtgg gcatgaatct   1320
gatgctgttt ccctgcagac aatgcgagag aatgaatcag aattcaaata tctgcttcac   1380
tcacggacag aaagactgtt tagagtgctt cccgtgtca gaatctcaac ccgtttctgt    1440
cgtcaaaaag gcgtatcaga aactgtgcta cattcatcat atcatgggaa aggtgccaga   1500
cgcttgcact gcctgcgatc tggtcaatgt ggatttggat gactgcatct ttgaacaata   1560
aatgatttaa atcaggtatg gctgccgatg gttatcttcc agattggctc gaggacaacc   1620
tctctgaggg cattcgcgag tggtgggact gaaacctgg agccccgaag cccaaagcca    1680
accagcaaaa gcaggacgac ggccggggtc tggtgcttcc tggctacaag tacctcggac   1740
ccttcaacgg actcgacaag ggggagcccg tcaacgcggc ggacgcagcg gccctcgagc   1800
acgacaaggc ctacgaccag cagctcaaag cgggtgacaa tccgtacctg cggtataacc   1860
acgccgacgc cgagtttcag gagcgtctgc aagaagatac gtcttttggg ggcaacctcg   1920
ggcgagcagt cttccaggcc aagaagcggg ttctcgaacc tctcggtctg gttgaggaag   1980
gcgctaagac ggctcctgga aagaaacgtc cggtagagca gtcgccacaa gagccagact   2040
cctcctcggg catcggcaag acaggccagc agcccgctaa aaagagactc aattttggtc   2100
agactggcga ctcagagtca gtccccgatc cacaacctct cggagaacct ccagcaaccc   2160
ccgctgctgt gggacctact acaatggctt caggcggtgg cgcaccaatg gcagacaata   2220
acgaaggcgc cgacggagtg ggtaatgcct caggaaattg gcattgcgat tccacatggc   2280
tgggcgacag agtcatcacc accagcaccc gcacctgggc cttgcccacc tacaataacc   2340
acctctacaa gcaaatctcc agtgcttcaa cgggggccag caacgacaac cactacttcg   2400
gctacagcac ccctctgggg tattttgatt tcaacagatt ccactgccac ttttcaccac   2460
gtgactggca gcgactcatc aacaacaatt ggggattccg gcccaagaga ctcaacttca   2520
aactcttcaa catccaagtc aaggaggtca cgacgaatga tggcgtcaca accatcgcta   2580
ataaccttac cagcacggtt caagtcttct cggactcgga gtaccagctt ccgtacgtcc   2640
tcggctctgc gcaccaggc tgcctccctc cgttcccggc ggacgtgttc atgattccgc    2700
aatacggcta cctgacgctc aacaatggca gccaagccgt gggacgttca tccttttact   2760
gcctggaata tttcccttct cagatgctga gaacgggcaa caactttacc ttcagctaca   2820
cctttgagga agtgcctttc cacagcagct acgcgcacag ccagagcctg gaccggctga   2880
tgaatcctct catcgaccaa tacctgtatt acctgaacag aactcaaaat cagtccggaa   2940
gtgcccaaaa caaggacttg ctgtttagcc gtgggtctcc agctggcatg tctgttcagc   3000
ccaaaaactg gctacctgga ccctgttatc ggcagcagcg cgtttctaaa acaaaaacag   3060
```

```
acaacaacaa cagcaatttt acctggactg gtgcttcaaa atataacctc aatgggcgtg   3120
aatccatcat caaccctggc actgctatgg cctcacacaa agacgacgaa gacaagttct   3180
ttcccatgag cggtgtcatg attttttggaa aagagagcgc cggagcttca aacactgcat   3240
tggacaatgt catgattaca gacgaagagg aaattaaagc cactaaccct gtggccaccg   3300
aaagatttgg gaccgtggca gtcaatttcc agagcagcag cacagaccct gcgaccggag   3360
atgtgcatgc tatgggagca ttacctggca tggtgtggca agatagagac gtgtacctgc   3420
agggtcccat ttgggccaaa attcctcaca cagatggaca ctttcacccg tctcctctta   3480
tgggcggctt tggactcaag aacccgcctc ctcagatcct catcaaaaac acgcctgttc   3540
ctgcgaatcc tccggcggag ttttcagcta caaagtttgc ttcattcatc acccaatact   3600
ccacaggaca agtgagtgtg gaaattgaat gggagctgca gaaagaaaac agcaagcgct   3660
ggaatcccga agtgcagtac acatccaatt atgcaaaatc tgccaacgtt gattttactg   3720
tggacaacaa tggactttat actgagcctc gccccattgg cacccgttac cttaccegtc   3780 ccctgtaagg cgcgccaccg gttgcttgtt aatcaataaa ccgttaatt cgtttcagtt   3840 gaactttggt ctctgcgtat ttcttttctta tctagtttcc atgctctagg atccactagt   3900 aacgccgcc agtgtgctgg aattcggctt tgtagttaat gattaacccg ccatgctact   3960
tatctacgta gccatgctct agaggtcctg tattagaggt cacgtgagtg ttttgcgaca   4020
ttttgcgaca ccatgtggtc acgctgggta tttaagcccg agtgagcacg cagggtctcc   4080
attttgaagc gggaggtttg aacgcgcagc cgccaagccg aattctgcag atatccaaac   4140 actggcggc gctcgactag agcggccgcc accgcggtgg agctccagct tttgttccct   4200
ttagtgaggg ttaattgcgc gcttggcgta atcatggtca tagctgtttc ctgtgtgaaa   4260
ttgttatccg ctcacaattc cacacaacat acgagccgga agcataaagt gtaaagcctg   4320
gggtgcctaa tgagtgagct aactcacatt aattgcgttg cgctcactgc ccgctttcca   4380
gtcgggaaac ctgtcgtgcc agctgcatta atgaatcggc caacgcgcgg ggagaggcgg   4440
tttgcgtatt gggcgctctt ccgcttcctc gctcactgac tcgctgcgct cggtcgttcg   4500
gctgcggcga gcggtatcag ctcactcaaa ggcggtaata cggttatcca cagaatcagg   4560
ggataacgca ggaaagaaca tgtgagcaaa aggccagcaa aaggccagga accgtaaaaa   4620
ggccgcgttg ctggcgtttt tccataggct ccgccccccct gacgagcatc acaaaaatcg   4680
acgctcaagt cagaggtggc gaaacccgac aggactataa agataccagg cgtttccccc   4740
tggaagctcc ctcgtgcgct ctcctgttcc gaccctgccg cttaccggat acctgtccgc   4800 cttctccct tcgggaagcg tggcgctttc tcatagctca cgctgtaggt atctcagttc   4860
ggtgtaggtc gttcgctcca agctgggctg tgtgcacgaa ccccccgttc agcccgaccg   4920
ctgcgcctta tccggtaact atcgtcttga gtccaacccg gtaagacacg acttatcgcc   4980
actggcagca gccactggta acaggattag cagagcgagg tatgtaggcg gtgctacaga   5040
gttcttgaag tggtggccta actacggcta cactagaaga acagtatttg gtatctgcgc   5100
tctgctgaag ccagttacct tcggaaaaag agttggtagc tcttgatccg gcaaacaaac   5160
caccgctggt agcggtggtt ttttgttg caagcagcag attacgcgca gaaaaaaagg   5220
atctcaagaa gatcctttga tcttttctac ggggtctgac gctcagtgga acgaaaactc   5280
acgttaaggg attttggtca tgagattatc aaaaaggatc ttcacctaga tccttttaaa   5340
ttaaaaatga agttttaaat caatctaaag tatatatgag taaacttggt ctgacagtta   5400
ccaatgctta atcagtgagg cacctatctc agcgatctgt ctatttcgtt catccatagt   5460
```

```
tgcctgactc cccgtcgtgt agataactac gatacgggag ggcttaccat ctggccccag    5520
tgctgcaatg ataccgcgag acccacgctc accggctcca gatttatcag caataaacca    5580
gccagccgga agggccgagc gcagaagtgg tcctgcaact ttatccgcct ccatccagtc    5640
tattaattgt tgccgggaag ctagagtaag tagttcgcca gttaatagtt tgcgcaacgt    5700
tgttgccatt gctacaggca tcgtggtgtc acgctcgtcg tttggtatgg cttcattcag    5760
ctccggttcc caacgatcaa ggcgagttac atgatccccc atgttgtgca aaaaagcggt    5820
tagctccttc ggtcctccga tcgttgtcag aagtaagttg gccgcagtgt tatcactcat    5880
ggttatggca gcactgcata attctcttac tgtcatgcca tccgtaagat gcttttctgt    5940
gactggtgag tactcaacca agtcattctg agaatagtgt atgcggcgac cgagttgctc    6000
ttgcccggcg tcaatacggg ataataccgc gccacatagc agaactttaa aagtgctcat    6060
cattggaaaa cgttcttcgg ggcgaaaact ctcaaggatc ttaccgctgt tgagatccag    6120
ttcgatgtaa cccactcgtg cacccaactg atcttcagca tcttttactt tcaccagcgt    6180
ttctgggtga gcaaaaacag gaaggcaaaa tgccgcaaaa aagggaataa gggcgacacg    6240
gaaatgttga atactcatac tcttcctttt tcaatattat tgaagcattt atcagggtta    6300
ttgtctcatg agcggataca tatttgaatg tatttagaaa aataaacaaa tagggttcc    6360
gcgcacattt ccccgaaaag tgccacctaa attgtaagcg ttaatatttt gttaaaattc    6420
gcgttaaatt tttgttaaat cagctcattt tttaaccaat aggccgaaat cggcaaaatc    6480
ccttataaat caaagaata accgagata gggttgagtg ttgttccagt ttggaacaag    6540
agtccactat taagaacgt ggactccaac gtcaagggc gaaaaccgt ctatcagggc    6600
gatggcccac tacgtgaacc atcaccctaa tcaagttttt tggggtcgag gtgccgtaaa    6660
gcactaaatc ggaaccctaa agggagcccc cgatttagag cttgacgggg aaagccggcg    6720
aacgtggcga gaaaggaagg gaagaaagcg aaaggagcgg cgctagggc gctggcaagt    6780
gtagcggtca cgctgcgcgt aaccaccaca cccgccgcgc ttaatgcgcc gctacagggc    6840
gcgtcccatt cgccattcag gctgcgcaac tgttgggaag ggcgatcggt gcgggcctct    6900
tcgctattac gccagctggc gaaagggga tgtgctgcaa ggcgattaag ttgggtaacg    6960
ccagggtttt cccagtcacg acgttgtaaa acgacggcca gtgagcgcgc gtaatacgac    7020
tcactatagg gcgaattggg taccgggccc cccctcgagg tcgacggtat cggggagct    7080
cgcagggtct ccattttgaa gcgggaggtt tgaacgcgca gccgccatgc cgggttttta    7140
cgagattgtg attaaggtcc ccagcgacct tgacgagcat ctgcccggca tttctgacag    7200
ctttgtgaac tgggtggccg agaaggaatg ggagttgccg ccagattctg acatggatct    7260
gaatctgatt gagcaggcac ccctgaccgt ggccgagaag ctgcagcgcg actttctgac    7320
ggaatggcgc cgtgtgagta aggccccgga ggctcttttc tttgtgcaat tgagaaggg    7380
agagagctac ttccacatgc acgtgctcgt ggaaaccacc ggggtgaaat c    7431
```

<210> SEQ ID NO 2
<211> LENGTH: 7415
<212> TYPE: DNA
<213> ORGANISM: Artificial Sequence
<220> FEATURE:
<223> OTHER INFORMATION: Coding Strand of Plasmid pAAV-RC2

<400> SEQUENCE: 2

```
ccgggccccc cctcgaggtc gacggtatcg ggggagctcg cagggtctcc attttgaagc    60
```

```
gggaggtttg aacgcgcagc cgccatgccg gggttttacg agattgtgat taaggtcccc    120
agcgaccttg acgagcatct gcccggcatt tctgacagct ttgtgaactg ggtggccgag    180
aaggaatggg agttgccgcc agattctgac atggatctga atctgattga gcaggcaccc    240
ctgaccgtgg ccgagaagct gcagcgcgac tttctgacgg aatggcgccg tgtgagtaag    300
gccccggagg ctcttttctt tgtgcaattt gagaagggag agagctactt ccacatgcac    360
gtgctcgtgg aaaccaccgg ggtgaaatcc atggttttgg gacgtttcct gagtcagatt    420
cgcgaaaaac tgattcagag aatttaccgc gggatcgagc cgactttgcc aaactggttc    480
gcggtcacaa agaccagaaa tggcgccgga ggcgggaaca aggtggtgga tgagtgctac    540
atccccaatt acttgctccc caaaacccag cctgagctcc agtgggcgtg gactaatatg    600
gaacagtatt taagcgcctg tttgaatctc acggagcgta acggttggt ggcgcagcat    660 ctgacgcacg tgtcgcagac gcaggagcag aacaaagaga atcagaatcc caattctgat    720
gcgccggtga tcagatcaaa aacttcagcc aggtacatgg agctggtcgg gtggctcgtg    780
gacaagggga ttacctcgga gaagcagtgg atccaggagg accaggcctc atacatctcc    840
ttcaatgcgg cctccaactc gcggtcccaa atcaaggctg ccttggacaa tgcgggaaag    900
attatgagcc tgactaaaac cgccccccgac tacctggtgg ccagcagcc cgtggaggac    960 atttccagca atcggattta taaaattttg gaactaaacg ggtacgatcc ccaatatgcg   1020
gcttccgtct ttctgggatg ggccacgaaa agttcggca agaggaacac catctggctg   1080
tttgggcctg caactaccgg gaagaccaac atcgcggagg ccatagccca cactgtgccc   1140
ttctacgggt gcgtaaactg gaccaatgag aactttccct tcaacgactg tgtcgacaag   1200
atggtgatct ggtgggagga ggggaagatg accgccaagg tcgtggagtc ggccaaagcc   1260
attctcggag gaagcaaggt gcgcgtggac cagaaatgca gtcctcggc ccagatagac    1320 ccgactcccg tgatcgtcac ctccaacacc aacatgtgcg ccgtgattga cgggaactca   1380
acgaccttcg aacaccagca gccgttgcaa gaccggatgt tcaaatttga actcacccgc   1440
cgtctggatc atgactttgg gaaggtcacc aagcaggaag tcaaagactt tttccggtgg   1500
gcaaaggatc acgtggttga ggtggagcat gaattctacg tcaaaaaggg tggagccaag   1560
aaaagacccg cccccagtga cgcagatata agtgagccca acgggtgcg cgagtcagtt   1620 gcgcagccat cgacgtcaga gcggaagct tcgatcaact acgcagacag gtaccaaaac   1680
aaatgttctc gtcacgtggg catgaatctg atgctgtttc cctgcagaca atgcgagaga   1740
atgaatcaga attcaaatat ctgcttcact cacggacaga aagactgttt agagtgcttt   1800
cccgtgtcag aatctcaacc cgtttctgtc gtcaaaaagg cgtatcagaa actgtgctac   1860
attcatcata tcatgggaaa ggtgccagac gcttgcactg cctgcgatct ggtcaatgtg   1920
gatttggatg actgcatctt tgaacaataa atgatttaaa tcaggtatgg ctgccgatgg   1980
ttatcttcca gattggctcg aggacactct ctctgaagga ataagacagt ggtggaagct   2040
caaacctggc ccaccaccac caaagcccgc agagcggcat aaggacgaca gcaggggtct   2100
tgtgcttcct gggtacaagt acctcggacc cttcaacgga ctcgacaagg gagagccggt   2160
caacgaggca gacgccgcgg ccctcgagca cgacaaagcc tacgaccggc agctcgacag   2220
cggagacaac ccgtacctca gtacaaccca gccgacgcg gagtttcagg agcgccttaa   2280
agaagatacg tcttttgggg gcaacctcgg acgagcagtc ttccaggcga aaaagagggt   2340
tcttgaacct ctgggcctgg ttgaggaacc tgttaagacg gctccgggaa aaaagaggcc   2400
ggtagagcac tctcctgtgg agccagactc ctcctcggga accggaaagg cgggccagca   2460
```

```
gcctgcaaga aaaagattga attttggtca gactggagac gcagactcag tacctgaccc    2520
ccagcctctc ggacagccac cagcagcccc ctctggtctg ggaactaata cgatggctac    2580
aggcagtggc gcaccaatgg cagacaataa cgagggcgcc gacggagtgg gtaattcctc    2640
gggaaattgg cattgcgatt ccacatggat gggcgacaga gtcatcacca ccagcacccg    2700
aacctgggcc ctgcccacct acaacaacca cctctacaaa caaatttcca gccaatcagg    2760
agcctcgaac gacaatcact actttggcta cagcacccct tggggggtatt ttgacttcaa    2820 cagattccac tgccactttt caccacgtga ctggcaaaga ctcatcaaca caactgggg    2880 attccgaccc aagagactca acttcaagct ctttaacatt caagtcaaag aggtcacgca    2940
gaatgacggt acgacgacga ttgccaataa ccttaccagc acggttcagg tgtttactga    3000
ctcggagtac cagctcccgt acgtcctcgg ctcggcgcat caaggatgcc tcccgccgtt    3060
cccagcagac gtcttcatgg tgccacagta tggatacctc accctgaaca acgggagtca    3120
ggcagtagga cgctcttcat tttactgcct ggagtacttt ccttctcaga tgctgcgtac    3180
cggaaacaac tttaccttca gctacacttt tgaggacgtt cctttccaca gcagctacgc    3240
tcacagccag agtctggacc gtctcatgaa tcctctcatc gaccagtacc tgtattactt    3300
gagcagaaca aacactccaa gtggaaccac cacgcagtca aggcttcagt tttctcaggc    3360
cggagcgagt gacattcggg accagtctag gaactggctt cctggaccct gttaccgcca    3420
gcagcgagta tcaaagacat ctgcggataa caacaacagt gaatactcgt ggactggagc    3480
taccaagtac cacctcaatg gcagagactc tctggtgaat ccgggcccgg ccatggcaag    3540
ccacaaggac gatgaagaaa agttttttcc tcagagcggg gttctcatct tgggaagca    3600 aggctcagag aaaacaaatg tggacattga aaaggtcatg attacagacg aagaggaaat    3660
caggacaacc aatcccgtgg ctacggagca gtatggttct gtatctacca acctccagag    3720
aggcaacaga caagcagcta ccgcagatgt caacacacaa ggcgttcttc caggcatggt    3780
ctggcaggac agagatgtgt accttcaggg gcccatctgg gcaaagattc cacacacgga    3840
cggacatttt caccccctctc ccctcatggg tggattcgga cttaaacacc ctcctccaca    3900
gattctcatc aagaacaccc cggtacctgc gaatccttcg accaccttca gtgcggcaaa    3960
gtttgcttcc ttcatcacac agtactccac gggacaggtc agcgtggaga tcgagtggga    4020
gctgcagaag gaaaacagca aacgctggaa tcccgaaatt cagtacactt ccaactacaa    4080
caagtctgtt aatgtggact ttactgtgga cactaatggc gtgtattcag agcctcgccc    4140
cattggcacc agatacctga ctcgtaatct gtaattgctt gttaatcaat aaaccgttta    4200
attcgtttca gttgaacttt ggtctctgcg tatttctttc ttatctagtt tccatgctct    4260
aggatccact agtaacggcc gccagtgtgc tggaattcgg ctttgtagtt aatgattaac    4320
ccgccatgct acttatctac gtagccatgc tctagaggtc ctgtattaga ggtcacgtga    4380
gtgttttgcg acattttgcg acaccatgtg gtcacgctgg gtatttaagc ccgagtgagc    4440
acgcagggtc tccattttga agcgggaggt ttgaacgcgc agccgccaag ccgaattctg    4500
cagatatcca aacactggcg gccgctcgac tagagcggcc gccaccgcgg tggagctcca    4560
gcttttgttc cctttagtga gggttaattg cgcgcttggc gtaatcatgg tcatagctgt    4620
ttcctgtgtg aaattgttat ccgctcacaa ttccacacaa catacgagcc ggaagcataa    4680
agtgtaaagc ctggggtgcc taatgagtga gctaactcac attaattgcg ttgcgctcac    4740
tgcccgcttt ccagtcggga aacctgtcgt gccagctgca ttaatgaatc ggccaacgcg    4800
```

```
cggggagagg cggtttgcgt attgggcgct cttccgcttc ctcgctcact gactcgctgc    4860
gctcggtcgt tcggctgcgg cgagcggtat cagctcactc aaaggcggta atacggttat    4920
ccacagaatc aggggataac gcaggaaaga acatgtgagc aaaaggccag caaaaggcca    4980
ggaaccgtaa aaaggccgcg ttgctggcgt ttttccatag gctccgcccc cctgacgagc    5040
atcacaaaaa tcgacgctca agtcagaggt ggcgaaaccc gacaggacta taaagatacc    5100
aggcgtttcc ccctggaagc tccctcgtgc gctctcctgt tccgaccctg ccgcttaccg    5160
gatacctgtc cgcctttctc ccttcgggaa gcgtggcgct ttctcatagc tcacgctgta    5220
ggtatctcag ttcggtgtag gtcgttcgct ccaagctggg ctgtgtgcac gaaccccccg    5280
ttcagcccga ccgctgcgcc ttatccggta actatcgtct tgagtccaac ccggtaagac    5340
acgacttatc gccactggca gcagccactg gtaacaggat tagcagagcg aggtatgtag    5400
gcggtgctac agagttcttg aagtggtggc ctaactacgg ctacactaga agaacagtat    5460
ttggtatctg cgctctgctg aagccagtta ccttcggaaa aagagttggt agctcttgat    5520
ccggcaaaca aaccaccgct ggtagcggtg gtttttttgt ttgcaagcag cagattacgc    5580
gcagaaaaaa aggatctcaa gaagatcctt tgatcttttc tacggggtct gacgctcagt    5640
ggaacgaaaa ctcacgttaa gggattttgg tcatgagatt atcaaaaagg atcttcacct    5700
agatcctttt aaattaaaaa tgaagtttta aatcaatcta agtatatat gagtaaactt    5760 ggtctgacag ttaccaatgc ttaatcagtg aggcaccta t ctcagcgatc tgtctatttc    5820
gttcatccat agttgcctga ctccccgtcg tgtagataac tacgatacgg gagggcttac    5880
catctggccc cagtgctgca atgataccgc gagacccacg ctcaccggct ccagatttat    5940
cagcaataaa ccagccagcc ggaagggccg agcgcagaag tggtcctgca actttatccg    6000
cctccatcca gtctattaat tgttgccggg aagctagagt aagtagttcg ccagttaata    6060
gtttgcgcaa cgttgttgcc attgctacag gcatcgtggt gtcacgctcg tcgtttggta    6120
tggcttcatt cagctccggt tcccaacgat caaggcgagt tacatgatcc cccatgttgt    6180
gcaaaaaagc ggttagctcc ttcggtcctc cgatcgttgt cagaagtaag ttggccgcag    6240
tgttatcact catggttatg gcagcactgc ataattctct tactgtcatg ccatccgtaa    6300
gatgcttttc tgtgactggt gagtactcaa ccaagtcatt ctgagaatag tgtatgcggc    6360
gaccgagttg ctcttgcccg gcgtcaatac gggataatac cgcgccacat agcagaactt    6420
taaaagtgct catcattgga aaacgttctt cggggcgaaa actctcaagg atcttaccgc    6480
tgttgagatc cagttcgatg taacccactc gtgcacccaa ctgatcttca gcatctttta    6540
ctttcaccag cgtttctggg tgagcaaaaa caggaaggca aaatgccgca aaaagggaa    6600 taagggcgac acggaaatgt tgaatactca tactcttcct ttttcaatat tattgaagca    6660
tttatcaggg ttattgtctc atgagcggat acatatttga atgtatttag aaaaataaac    6720
aaataggggt tccgcgcaca tttccccgaa aagtgccacc taaattgtaa gcgttaatat    6780
tttgttaaaa ttcgcgttaa attttttgtta atcagctca ttttttaacc aataggccga    6840
aatcggcaaa atcccttata aatcaaaaga atagaccgag atagggttga gtgttgttcc    6900
agtttggaac aagagtccac tattaaagaa cgtggactcc aacgtcaaag ggcgaaaaac    6960
cgtctatcag ggcgatggcc cactacgtga accatcaccc taatcaagtt ttttggggtc    7020
gaggtgccgt aaagcactaa atcggaaccc taaagggagc ccccgattta gagcttgacg    7080
gggaaagccg gcgaacgtgg cgagaaagga agggaagaaa gcgaaaggag cgggcgctag    7140
ggcgctggca agtgtagcgg tcacgctgcg cgtaaccacc acacccgccg cgcttaatgc    7200
```

```
gccgctacag ggcgcgtccc attcgccatt caggctgcgc aactgttggg aagggcgatc    7260
ggtgcgggcc tcttcgctat tacgccagct ggcgaaaggg ggatgtgctg caaggcgatt    7320 aagtttgggta acgccagggt tttcccagtc acgacgttgt aaaacgacgg ccagtgagcg    7380
cgcgtaatac gactcactat agggcgaatt gggta                               7415

<210> SEQ ID NO 3
<211> LENGTH: 7395
<212> TYPE: DNA
<213> ORGANISM: Artificial Sequence
<220> FEATURE:
<223> OTHER INFORMATION: Coding Strand of Plasmid pAAV-RC5

<400> SEQUENCE: 3
catggttttg ggacgtttcc tgagtcagat tcgcgaaaaa ctgattcaga gaatttaccg      60
cgggatcgag ccgactttgc caaactggtt cgcggtcaca aagaccagaa atggcgccgg    120
aggcgggaac aaggtggtgg atgagtgcta catccccaat tacttgctcc ccaaaaccca    180
gcctgagctc cagtgggcgt ggactaatat ggaacagtat ttaagcgcct gtttgaatct    240
cacggagcgt aaacggttgg tggcgcagca tctgacgcac gtgtcgcaga cgcaggagca    300
gaacaaagag aatcagaatc ccaattctga tgcgccggtg atcagatcaa aaacttcagc    360
caggtacatg gagctggtcg ggtggctcgt ggacaagggg attacctcgg agaagcagtg    420
gatccaggag gaccaggcct catacatctc cttcaatgcg gcctccaact cgcggtccca    480
aatcaaggct gccttggaca atgcgggaaa gattatgagc ctgactaaaa ccgcccccga    540
ctacctggtg ggccagcagc ccgtggagga catttccagc aatcggattt ataaaatttt    600
ggaactaaac gggtacgatc cccaatatgc ggcttccgtc tttctgggat gggcacgaa    660 aaagttcggc aagaggaaca ccatctggct gtttgggcct gcaactaccg gaagaccaa    720 catcgcggag gccatagccc acactgtgcc cttctacggg tgcgtaaact ggaccaatga    780
gaactttccc ttcaacgact gtgtcgacaa gatggtgatc tggtgggagg aggggaagat    840
gaccgccaag gtcgtggagt cggccaaagc cattctcgga ggaagcaagg tgcgcgtgga    900
ccagaaatgc aagtcctcgg cccagataga cccgactccc gtgatcgtca cctccaacac    960
caacatgtgc gccgtgattg acgggaactc aacgaccttc gaacaccagc agccgttgca    1020
agaccggatg ttcaaatttg aactcacccg ccgtctggat catgactttg gaaaggtcac    1080
caagcaggaa gtcaaagact ttttccggtg gcaaaggat cacgtggttg aggtggagca    1140
tgaattctac gtcaaaaagg gtggagccaa gaaaagaccc gccccagtg acgcagatat    1200 aagtgagccc aaacgggtgc gcgagtcagt tgcgcagcca tcgacgtcag acgcggaagc    1260
ttcgatcaac tacgcagaca ggtaccaaaa caaatgttct cgtcacgtgg gcatgaatct    1320
gatgctgttt ccctgcagac aatgcgagag aatgaatcag aattcaaata tctgcttcac    1380
tcacggacag aaagactgtt tagagtgctt tcccgtgtca gaatctcaac ccgtttctgt    1440
cgtcaaaaag gcgtatcaga aactgtgcta cattcatcat atcatgggaa aggtgccaga    1500
cgcttgcact gcctgcgatc tggtcaatgt ggatttggat gactgcatct ttgaacaata    1560
aatgatttaa atcaggtatg tctttgttg atcaccctcc agattggttg gaagaagttg    1620
gtgaaggtct tcgcgagttt ttgggccttg aagcgggccc accgaaacca aacccaatc    1680 agcagcatca agatcaagcc cgtggtcttg tgctgcctgg ttataactat ctcggacccg    1740
gaaacggtct cgatcgagga gagcctgtca acagggcaga cgaggtcgcg cgagagcacg    1800
```

```
acatctcgta caacgagcag cttgaggcgg gagacaaccc ctacctcaag tacaaccacg    1860
cggacgccga gtttcaggag aagctcgccg acgacacatc cttcggggga aacctcggaa    1920
aggcagtctt tcaggccaag aaaagggttc tcgaacctt tggcctggtt gaagagggtg     1980
ctaagacggc ccctaccgga aagcggatag acgaccactt tccaaaaaga aagaaggctc    2040
ggaccgaaga ggactccaag ccttccacct cgtcagacgc cgaagctgga cccagcggat    2100
cccagcagct gcaaatccca gcccaaccag cctcaagttt gggagctgat acaatgtctg    2160
cgggaggtgg cggcccattg ggcgacaata accaaggtgc cgatggagtg ggcaatgcct    2220
cgggagattg gcattgcgat tccacgtgga tgggggacag agtcgtcacc aagtccaccc    2280
gaacctgggt gctgcccagc tacaacaacc accagtaccg agagatcaaa agcggctccg    2340
tcgacggaag caacgccaac gcctactttg atacagcac cccctggggg tactttgact     2400
ttaaccgctt ccacagccac tggagccccc gagactggca aagactcatc aacaactact    2460
ggggcttcag accccggtcc ctcagagtca aaatcttcaa cattcaagtc aaagaggtca    2520
cggtgcagga ctccaccacc accatcgcca acaacctcac ctccaccgtc caagtgttta    2580
cggacgacga ctaccagctg ccctacgtcg tcggcaacgg gaccgaggga tgcctgccgg    2640
ccttccctcc gcaggtcttt acgctgccgc agtacggtta cgcgacgctg aaccgcgaca    2700
acacagaaaa tcccaccgag aggagcagct tcttctgcct agagtacttt cccagcaaga    2760
tgctgagaac gggcaacaac tttgagttta cctacaactt tgaggaggtg cccttccact    2820
ccagcttcgc tcccagtcag aacctgttca agctggccaa cccgctggtg gaccagtact    2880
tgtaccgctt cgtgagcaca aataacactg gcggagtcca gttcaacaag aacctggccg    2940
ggagatacgc caacacctac aaaaactggt tcccggggcc catgggccga acccagggct    3000
ggaacctggg ctccggggtc aaccgcgcca gtgtcagcgc cttcgccacg accaatagga    3060
tggagctcga gggcgcgagt taccaggtgc ccccgcagcc gaacggcatg accaacaacc    3120
tccagggcag caacaccta tgccctggaga acactatgat cttcaacagc agccggcga    3180 acccgggcac caccgccacg tacctcgagg gcaacatgct catcaccagc gagagcgaga    3240
cgcagccggt gaaccgcgtg gcgtacaacg tcggcgggca gatggccacc aacaaccaga    3300
gctccaccac tgcccccgcg accggcacgt acaacctcca ggaaatcgtg cccggcagcg    3360
tgtggatgga gagggacgtg tacctccaag gacccatctg gccaagatc ccagagacgg     3420 gggcgcactt tcaccctct ccggccatgg gcggattcgg actcaaacac ccaccgccca     3480
tgatgctcat caagaacacg cctgtgcccg gaaatatcac cagcttctcg gacgtgcccg    3540
tcagcagctt catcacccag tacagcaccg ggcaggtcac cgtggagatg gagtgggagc    3600
tcaagaagga aaactccaag aggtggaacc cagagatcca gtacacaaac aactacaacg    3660
acccccagtt tgtggacttt gccccggaca gcaccgggga atacagaacc accagaccta    3720
tcggaacccg ataccttacc cgaccccttt aaggcgcgcc accggttgct tgttaatcaa    3780
taaaccgttt aattcgtttc agttgaactt tggtctctgc gtatttcttt cttatctagt    3840
ttccatgctc taggatccac tagtaacggc cgccagtgtg ctggaattcg ctttgtagt     3900 taatgattaa cccgccatgc tacttatcta cgtagccatg ctctagaggt cctgtattag    3960
aggtcacgtg agtgttttgc gacattttgc gacaccatgt ggtcacgctg gtatttaag    4020 cccgagtgag cacgcagggt ctcattttg aagcggagg tttgaacgcg cagccgccaa     4080
gccgaattct gcagatatcc aaacactggc ggccgctcga ctagagcggc cgccaccgcg    4140
gtggagctcc agcttttgtt ccctttagtg agggttaatt gcgcgcttgg cgtaatcatg    4200
```

```
gtcatagctg tttcctgtgt gaaattgtta tccgctcaca attccacaca acatacgagc   4260
cggaagcata aagtgtaaag cctggggtgc ctaatgagtg agctaactca cattaattgc   4320
gttgcgctca ctgcccgctt tccagtcggg aaacctgtcg tgccagctgc attaatgaat   4380
cggccaacgc gcggggagag gcggtttgcg tattgggcgc tcttccgctt cctcgctcac   4440
tgactcgctg cgctcggtcg ttcggctgcg gcgagcggta tcagctcact caaaggcggt   4500
aatacggtta tccacagaat cagggggataa cgcaggaaag aacatgtgag caaaaggcca   4560
gcaaaaggcc aggaaccgta aaaaggccgc gttgctggcg ttttccata ggctccgccc    4620 ccctgacgag catcacaaaa atcgacgctc aagtcagagg tggcgaaacc cgacaggact   4680
ataaagatac caggcgtttc cccctggaag ctccctcgtg cgctctcctg ttccgaccct   4740
gccgcttacc ggatacctgt ccgcctttct cccttcggga agcgtggcgc tttctcatag   4800
ctcacgctgt aggtatctca gttcggtgta ggtcgttcgc tccaagctgg gctgtgtgca   4860 cgaaccccc gttcagcccg accgctgcgc cttatccggt aactatcgtc ttgagtccaa    4920
cccggtaaga cacgacttat cgccactggc agcagccact ggtaacagga ttagcagagc   4980
gaggtatgta ggcggtgcta cagagttctt gaagtggtgg cctaactacg gctacactag   5040
aagaacagta tttggtatct gcgctctgct gaagccagtt accttcggaa aaagagttgg   5100
tagctcttga tccggcaaac aaaccaccgc tggtagcggt ggtttttttg tttgcaagca   5160
gcagattacg cgcagaaaaa aaggatctca agaagatcct ttgatctttt ctacggggtc   5220
tgacgctcag tggaacgaaa actcacgtta agggattttg gtcatgagat tatcaaaaag   5280
gatcttcacc tagatccttt taaattaaaa atgaagtttt aaatcaatct aaagtatata   5340
tgagtaaact tggtctgaca gttaccaatg cttaatcagt gaggcaccta tctcagcgat   5400
ctgtctattt cgttcatcca tagttgcctg actccccgtc gtgtagataa ctacgatacg   5460
ggagggctta ccatctggcc ccagtgctgc aatgataccg cgagacccac gctcaccggc   5520
tccagattta tcagcaataa accagccagc cggaagggcc gagcgcagaa gtggtcctgc   5580
aactttatcc gcctccatcc agtctattaa ttgttgccgg gaagctagag taagtagttc   5640
gccagttaat agtttgcgca acgttgttgc cattgctaca ggcatcgtgg tgtcacgctc   5700
gtcgtttggt atggcttcat tcagctccgg ttcccaacga tcaaggcgag ttacatgatc   5760
ccccatgttg tgcaaaaaag cggttagctc cttcggtcct ccgatcgttg tcagaagtaa   5820
gttggccgca gtgttatcac tcatggttat ggcagcactg cataattctc ttactgtcat   5880
gccatccgta agatgctttt ctgtgactgg tgagtactca accaagtcat tctgagaata   5940
gtgtatgcgg cgaccgagtt gctcttgccc ggcgtcaata cgggataata ccgcgccaca   6000
tagcagaact ttaaaagtgc tcatcattgg aaaacgttct cggggcgaa aactctcaag    6060 gatcttaccg ctgttgagat ccagttcgat gtaacccact cgtgcaccca actgatcttc   6120
agcatctttt actttcacca gcgtttctgg gtgagcaaaa acaggaaggc aaaatgccgc   6180
aaaaagggga ataagggcga cacggaaatg ttgaatactc atactcttcc ttttcaata    6240 ttattgaagc atttatcagg gttattgtct catgagcgga tacatatttg aatgtattta   6300
gaaaaataaa caaatagggg ttccgcgcac atttccccga aaagtgccac ctaaattgta   6360
agcgttaata ttttgttaaa attcgcgtta aattttgtt aaatcagctc attttttaac    6420
caataggccg aaatcggcaa aatcccttat aaatcaaaag aatagaccga gatagggttg   6480
agtgttgttc cagtttggaa caagagtcca ctattaaaga acgtggactc caacgtcaaa   6540
```

-continued

| | |
|---|---|
| gggcgaaaaa ccgtctatca gggcgatggc ccactacgtg aaccatcacc ctaatcaagt | 6600 |
| ttttgggt cgaggtgccg taaagcacta atcggaacc ctaaaggag cccccgattt | 6660 |
| agagcttgac ggggaaagcc ggcgaacgtg gcgagaaagg aagggaagaa agcgaaagga | 6720 |
| gcgggcgcta gggcgctggc aagtgtagcg gtcacgctgc gcgtaaccac cacacccgcc | 6780 |
| gcgcttaatg cgccgctaca gggcgcgtcc cattcgccat tcaggctgcg caactgttgg | 6840 |
| gaagggcgat cggtgcgggc ctcttcgcta ttacgccagc tggcgaaagg gggatgtgct | 6900 |
| gcaaggcgat taagttgggt aacgccaggg ttttcccagt cacgacgttg taaaacgacg | 6960 |
| gccagtgagc gcgcgtaata cgactcacta tagggcgaat tgggtaccgg ccccccctc | 7020 |
| gaggtcgacg gtatcggggg agctcgcagg gtctccattt tgaagcggga ggtttgaacg | 7080 |
| cgcagccgcc atgccggggt tttacgagat tgtgattaag gtcccagcg accttgacga | 7140 |
| gcatctgccc ggcatttctg acagctttgt gaactgggtg gccgagaagg aatgggagtt | 7200 |
| gccgccagat tctgacatgg atctgaatct gattgagcag gcaccctga ccgtggccga | 7260 |
| gaagctgcag cgcgactttc tgacggaatg gcgccgtgtg agtaaggccc cggaggctct | 7320 |
| tttctttgtg caatttgaga agggagagag ctacttccac atgcacgtgc tcgtggaaac | 7380 |
| caccggggtg aaatc | 7395 |

<210> SEQ ID NO 4
<211> LENGTH: 7431
<212> TYPE: DNA
<213> ORGANISM: Artificial Sequence
<220> FEATURE:
<223> OTHER INFORMATION: Coding Strand of Plasmid pAAV-RC6

<400> SEQUENCE: 4

| | |
|---|---|
| catggttttg gacgtttcc tgagtcagat tcgcgaaaaa ctgattcaga gaatttaccg | 60 |
| cgggatcgag ccgactttgc caaactggtt cgcggtcaca aagaccagaa atggcgccgg | 120 |
| aggcgggaac aagtggtgg atgagtgcta catccccaat tacttgctcc ccaaaaccca | 180 |
| gcctgagctc cagtgggcgt ggactaatat ggaacagtat ttaagcgcct gtttgaatct | 240 |
| cacgagcgt aaacggttgg tggcgcagca tctgacgcac gtgtcgcaga cgcaggagca | 300 |
| gaacaaagag aatcagaatc ccaattctga tgcgccggtg atcagatcaa aaacttcagc | 360 |
| caggtacatg gagctggtcg ggtggctcgt ggacaagggg attacctcgg agaagcagtg | 420 |
| gatccaggag gaccaggcct catacatctc cttcaatgcg gcctccaact cgcggtccca | 480 |
| aatcaaggct gccttggaca atgcgggaaa gattatgagc ctgactaaaa ccgcccccga | 540 |
| ctacctggtg ggccagcagc ccgtggagga catttccagc aatcggattt ataaaatttt | 600 |
| ggaactaaac gggtacgatc cccaatatgc ggcttccgtc tttctgggat gggcacgaa | 660 |
| aaagttcggc aagaggaaca ccatctggct gtttgggcct gcaactaccg ggaagaccaa | 720 |
| catcgcggag gccatagccc acactgtgcc cttctacggg tgcgtaaact ggaccaatga | 780 |
| gaactttccc ttcaacgact gtgtcgacaa gatggtgatc tggtgggagg aggggaagat | 840 |
| gaccgccaag gtcgtggagt cggccaaagc cattctcgga ggaagcaagg tgcgcgtgga | 900 |
| ccagaaatgc aagtcctcgg cccagataga cccgactccc gtgatcgtca cctccaacac | 960 |
| caacatgtgc gccgtgattg acgggaactc aacgaccttc gaacaccagc agccgttgca | 1020 |
| agaccggatg ttcaaattg aactcacccg ccgtctggat catgactttg gaaggtcac | 1080 |
| caagcaggaa gtcaaagact ttttccgtgt ggcaaaggat cacgtggttg aggtggcagca | 1140 |
| tgaattctac gtcaaaaagg gtggagccaa gaaaagaccc gcccccagtg acgcagatat | 1200 |

```
aagtgagccc aaacgggtgc gcgagtcagt tgcgcagcca tcgacgtcag acgcggaagc    1260
ttcgatcaac tacgcagaca ggtaccaaaa caaatgttct cgtcacgtgg gcatgaatct    1320
gatgctgttt ccctgcagac aatgcgagag aatgaatcag aattcaaata tctgcttcac    1380
tcacggacag aaagactgtt tagagtgctt cccgtgtca gaatctcaac ccgtttctgt     1440
cgtcaaaaag gcgtatcaga aactgtgcta cattcatcat atcatgggaa aggtgccaga    1500
cgcttgcact gcctgcgatc tggtcaatgt ggatttggat gactgcatct ttgaacaata    1560
aatgatttaa atcaggtatg gctgccgatg ttatcttcc agattggctc gaggacaacc     1620
tctctgaggg cattcgcgag tggtgggact tgaaacctgg agccccgaaa cccaaagcca    1680
accagcaaaa gcaggacgac ggccgggggtc tggtgcttcc tggctacaag tacctcggac   1740
ccttcaacgg actcgacaag ggggagcccg tcaacgcggc ggatgcagcg gccctcgagc    1800
acgacaaggc ctacgaccag cagctcaaag cgggtgacaa tccgtacctg cggtataacc    1860
acgccgacgc cgagtttcag gagcgtctgc aagaagatac gtcttttggg ggcaacctcg    1920
ggcgagcagt cttccaggcc aagaagaggg ttctcgaacc ttttggtctg gttgaggaag    1980
gtgctaagac ggctcctgga aagaaacgtc cggtagagca gtcgccacaa gagccagact    2040
cctcctcggg cattggcaag acaggccagc agcccgctaa aaagagactc aattttggtc    2100
agactggcga ctcagagtca gtccccgacc acaacctct cggagaacct ccagcaaccc     2160
ccgctgctgt gggacctact acaatggctt caggcggtgg cgcaccaatg gcagacaata    2220
acgaaggcgc cgacggagtg ggtaatgcct caggaaattg gcattgcgat tccacatggc    2280
tgggcgacag agtcatcacc accagcaccc gaacatgggc cttgcccacc tataacaacc    2340
acctctacaa gcaaatctcc agtgcttcaa cgggggccag caacgacaac cactacttcg    2400
gctacagcac cccctggggg tattttgatt tcaacagatt ccactgccat ttctcaccac    2460
gtgactggca gcgactcatc aacaacaatt ggggattccg gcccaagaga ctcaacttca    2520
agctcttcaa catccaagtc aaggaggtca cgacgaatga tggcgtcacg accatcgcta    2580
ataaccttac cagcacggtt caagtcttct cggactcgga gtaccagttg ccgtacgtcc    2640
tcggctctgc gcaccagggc tgcctccctc cgttcccggc ggacgtgttc atgattccgc    2700
agtacggcta cctaacgctc aacaatggca gccaggcagt gggacggtca tccttttact    2760
gcctggaata tttcccatcg cagatgctga gaacgggcaa taactttacc ttcagctaca    2820
ccttcgagga cgtgcctttc cacagcagct acgcgcacag ccagagcctg accggctga    2880
tgaatcctct catcgaccag tacctgtatt acctgaacag aactcagaat cagtccggaa    2940
gtgcccaaaa caaggacttg ctgtttagcc gggggtctcc agctggcatg tctgttcagc    3000
ccaaaaactg gctacctgga ccctgttacc ggcagcagcg cgtttctaaa acaaaaacag    3060
acaacaacaa cagcaacttt acctggactg gtgcttcaaa atataacctt aatgggcgtg    3120
aatctataat caaccctggc actgctatgg cctcacacaa agacgacaaa gacaagttct    3180
ttcccatgag cggtgtcatg atttttggaa aggagagcgc cggagcttca aacactgcat    3240
tggacaatgt catgatcaca gacgaagagg aaatcaaagc cactaacccc gtggccaccg    3300
aaagatttgg gactgtggca gtcaatctcc agagcagcag cacagaccct gcgaccggag    3360
atgtgcatgt tatgggagcc ttacctggaa tggtgtggca agacagagac gtatacctgc    3420
agggtcctat ttgggccaaa attcctcaca cggatgacac ctttcacccg tctcctctca    3480
tgggcggctt tggacttaag cacccgcctc ctcagatcct catcaaaaac acgcctgttc    3540
```

```
ctgcgaatcc tccggcagag ttttcggcta caaagtttgc ttcattcatc acccagtatt    3600
ccacaggaca agtgagcgtg gagattgaat gggagctgca gaaagaaaac agcaaacgct    3660
ggaatcccga agtgcagtat acatctaact atgcaaaatc tgccaacgtt gatttcactg    3720
tggacaacaa tggactttat actgagcctc gccccattgg cacccgttac ctcacccgtc    3780
ccctgtaagg cgcgccaccg gttgcttgtt aatcaataaa ccgtttaatt cgtttcagtt    3840
gaactttggt ctctgcgtat ttcttttctta tctagtttcc atgctctagg atccactagt    3900
aacggccgcc agtgtgctgg aattcggctt tgtagttaat gattaacccg ccatgctact    3960
tatctacgta gccatgctct agaggtcctg tattagaggt cacgtgagtg ttttgcgaca    4020
ttttgcgaca ccatgtggtc acgctgggta tttaagcccg agtgagcacg cagggtctcc    4080
attttgaagc gggaggtttg aacgcgcagc cgccaagccg aattctgcag atatccaaac    4140
actgcggcc gctcgactag agcggccgcc accgcggtgg agctccagct tttgttccct    4200
ttagtgaggg ttaattgcgc gcttggcgta atcatggtca tagctgtttc ctgtgtgaaa    4260
ttgttatccg ctcacaattc cacacaacat acgagccgga agcataaagt gtaaagcctg    4320
gggtgcctaa tgagtgagct aactcacatt aattgcgttg cgctcactgc ccgctttcca    4380
gtcgggaaac ctgtcgtgcc agctgcatta atgaatcggc caacgcgcgg ggagaggcgg    4440
tttgcgtatt gggcgctctt ccgcttcctc gctcactgac tcgctgcgct cggtcgttcg    4500
gctgcggcga gcggtatcag ctcactcaaa ggcggtaata cggttatcca cagaatcagg    4560
ggataacgca ggaaagaaca tgtgagcaaa aggccagcaa aaggccagga accgtaaaaa    4620
ggccgcgttg ctggcgtttt tccataggct ccgcccccct gacgagcatc acaaaaatcg    4680
acgctcaagt cagaggtggc gaaacccgac aggactataa agataccagg cgtttccccc    4740
tggaagctcc ctcgtgcgct ctcctgttcc gaccctgccg cttaccggat acctgtccgc    4800
ctttctccct tcgggaagcg tggcgctttc tcatagctca cgctgtaggt atctcagttc    4860
ggtgtaggtc gttcgctcca agctgggctg tgtgcacgaa ccccccgttc agcccgaccg    4920
ctgcgcctta tccggtaact atcgtcttga gtccaacccg gtaagacacg acttatcgcc    4980
actggcagca gccactggta acaggattag cagagcgagg tatgtaggcg gtgctacaga    5040
gttcttgaag tggtggccta actacggcta cactagaaga acagtatttg gtatctgcgc    5100
tctgctgaag ccagttacct tcggaaaaag agttggtagc tcttgatccg gcaaacaaac    5160
caccgctggt agcggtggtt tttttgtttg caagcagcag attacgcgca gaaaaaaagg    5220
atctcaagaa gatcctttga tcttttctac ggggtctgac gctcagtgga acgaaaactc    5280
acgttaaggg attttggtca tgagattatc aaaaaggatc ttcacctaga tccttttaaa    5340
ttaaaaatga agttttaaat caatctaaag tatatatgag taaacttggt ctgacagtta    5400
ccaatgctta atcagtgagg cacctatctc agcgatctgt ctatttcgtt catccatagt    5460
tgcctgactc cccgtcgtgt agataactac gatacgggag ggcttaccat ctggccccag    5520
tgctgcaatg ataccgcgag acccacgctc accggctcca gatttatcag caataaacca    5580
gccagccgga agggccgagc gcagaagtgg tcctgcaact ttatccgcct ccatccagtc    5640
tattaattgt tgccgggaag ctagagtaag tagttcgcca gttaatagtt tgcgcaacgt    5700
tgttgccatt gctacaggca tcgtggtgtc acgctcgtcg tttggtatgg cttcattcag    5760
ctccggttcc caacgatcaa ggcgagttac atgatccccc atgttgtgca aaaaagcggt    5820
tagctccttc ggtcctccga tcgttgtcag aagtaagttg gccgcagtgt tatcactcat    5880
ggttatggca gcactgcata attctcttac tgtcatgcca tccgtaagat gcttttctgt    5940
```

```
gactggtgag tactcaacca agtcattctg agaatagtgt atgcggcgac cgagttgctc      6000
ttgcccggcg tcaatacggg ataataccgc gccacatagc agaactttaa aagtgctcat      6060
cattggaaaa cgttcttcgg ggcgaaaact ctcaaggatc ttaccgctgt tgagatccag      6120
ttcgatgtaa cccactcgtg cacccaactg atcttcagca tcttttactt tcaccagcgt      6180
ttctgggtga gcaaaaacag gaaggcaaaa tgccgcaaaa aagggaataa gggcgacacg      6240
gaaatgttga atactcatac tcttcctttt tcaatattat tgaagcattt atcagggtta      6300
ttgtctcatg agcggataca tatttgaatg tatttagaaa aataaacaaa tagggggttcc    6360 gcgcacattt ccccgaaaag tgccacctaa attgtaagcg ttaatatttt gttaaaattc      6420
gcgttaaatt tttgttaaat cagctcattt tttaaccaat aggccgaaat cggcaaaatc      6480
ccttataaat caaagaata gaccgagata gggttgagtg ttgttccagt ttggaacaag       6540
agtccactat taagaacgt ggactccaac gtcaagggc gaaaaccgt ctatcagggc        6600 gatggcccac tacgtgaacc atcaccctaa tcaagttttt tggggtcgag gtgccgtaaa      6660
gcactaaatc ggaaccctaa agggagcccc cgatttagag cttgacgggg aaagccggcg      6720
aacgtggcga aaaggaagg gaagaaagcg aaaggagcgg gcgctagggc gctggcaagt      6780
gtagcggtca cgctgcgcgt aaccaccaca cccgccgcgc ttaatgcgcc gctacagggc      6840
gcgtcccatt cgccattcag gctgcgcaac tgttgggaag ggcgatcggt gcgggcctct      6900
tcgctattac gccagctggc gaaaggggga tgtgctgcaa ggcgattaag ttgggtaacg      6960
ccagggtttt cccagtcacg acgttgtaaa acgacggcca gtgagcgcgc gtaatacgac      7020
tcactatagg gcgaattggg taccgggccc cccctcgagg tcgacggtat cggggggagct    7080 cgcagggtct ccattttgaa gcgggaggtt tgaacgcgca gccgccatgc cggggtttta     7140
cgagattgtg attaaggtcc ccagcgacct tgacgagcat ctgcccggca tttctgacag    7200
ctttgtgaac tgggtggccg agaaggaatg ggagttgccg ccagattctg acatggatct     7260
gaatctgatt gagcaggcac ccctgaccgt ggccgagaag ctgcagcgcg actttctgac     7320
ggaatggcgc cgtgtgagta aggcccccgga ggctcttttc tttgtgcaat tgagaagggg    7380
agagagctac ttccacatgc acgtgctcgt ggaaaccacc ggggtgaaat c              7431

<210> SEQ ID NO 5
<211> LENGTH: 7434
<212> TYPE: DNA
<213> ORGANISM: Artificial Sequence
<220> FEATURE:
<223> OTHER INFORMATION: Coding Strand of Plasmid pAAV-RC7

<400> SEQUENCE: 5
catggttttg ggacgtttcc tgagtcagat tcgcgaaaaa ctgattcaga gaatttaccg       60
cgggatcgag ccgactttgc caaactggtt cgcggtcaca aagaccagaa atggcgccgg     120
aggcgggaac aagtggtgg atgagtgcta catccccaat tacttgctcc ccaaaaccca      180
gcctgagctc cagtgggcgt ggactaatat ggaacagtat ttaagcgcct gtttgaatct     240
cacggagcgt aaacggttgg tggcgcagca tctgacgcac gtgtcgcaga cgcaggagca    300
gaacaaagag aatcagaatc ccaattctga tgcgccggtg atcagatcaa aaacttcagc    360
caggtacatg gagctggtcg ggtggctcgt ggacaagggg attacctcgg agaagcagtg    420
gatccaggag gaccaggcct catacatctc cttcaatgcg gcctccaact cgcggtccca    480
aatcaaggct gccttggaca atgcgggaaa gattatgagc ctgactaaaa ccgcccccga     540
```

-continued

```
ctacctggtg ggccagcagc ccgtggagga catttccagc aatcggattt ataaaatttt    600
ggaactaaac gggtacgatc cccaatatgc ggcttccgtc tttctgggat gggccacgaa    660
aaagttcggc aagaggaaca ccatctggct gtttgggcct gcaactaccg ggaagaccaa    720
catcgcggag gccatagccc acactgtgcc cttctacggg tgcgtaaact ggaccaatga    780
gaactttccc ttcaacgact gtgtcgacaa gatggtgatc tggtgggagg aggggaagat    840
gaccgccaag gtcgtggagt cggccaaagc cattctcgga ggaagcaagg tgcgcgtgga    900
ccagaaatgc aagtcctcgg cccagataga cccgactccc gtgatcgtca cctccaacac    960
caacatgtgc gccgtgattg acgggaactc aacgaccttc gaacaccagc agccgttgca   1020
agaccggatg ttcaaatttg aactcacccg ccgtctggat catgactttg ggaaggtcac   1080
caagcaggaa gtcaaagact ttttccggtg ggcaaaggat cacgtggttg aggtggagca   1140
tgaattctac gtcaaaaagg gtggagccaa gaaaagaccc gcccccagtg acgcagatat   1200
aagtgagccc aaacgggtgc gcgagtcagt tgcgcagcca tcgacgtcag acgcggaagc   1260
ttcgatcaac tacgcagaca ggtaccaaaa caaatgttct cgtcacgtgg gcatgaatct   1320
gatgctgttt ccctgcagac aatgcgagag aatgaatcag aattcaaata tctgcttcac   1380
tcacggacag aaagactgtt tagagtgctt cccgtgtca gaatctcaac ccgtttctgt    1440
cgtcaaaaag gcgtatcaga aactgtgcta cattcatcat atcatgggaa aggtgccaga   1500
cgcttgcact gcctgcgatc tggtcaatgt ggatttggat gactgcatct ttgaacaata   1560
aatgatttaa atcaggtatg gctgccgatg ttatcttcc agattggctc gaggacaacc   1620
tctctgaggg cattcgcgag tggtgggacc tgaaacctgg agccccgaaa cccaaagcca   1680
accagcaaaa gcaggacaac ggccgggtc tggtgcttcc tggctacaag tacctcggac   1740
ccttcaacgg actcgacaag ggggagcccg tcaacgcggc ggacgcagcg gccctcgagc   1800
acgacaaggc ctacgaccag cagctcaaag cgggtgacaa tccgtacctg cggtataacc   1860
acgccgacgc cgagtttcag gagcgtctgc aagaagatac gtcatttggg ggcaacctcg   1920
ggcgagcagt cttccaggcc aagaagcggg ttctcgaacc tctcggtctg gttgaggaag   1980
gcgctaagac ggctcctgca aagaagagac cggtagagcc gtcacctcag cgttcccccg   2040
actcctccac gggcatcggc aagaaaggcc agcagcccgc cagaaagaga ctcaatttcg   2100
gtcagactgg cgactcagag tcagtccccg accctcaacc tctcggagaa cctccagcag   2160
cgccctctag tgtgggatct ggtacagtgg ctgcaggcgg tggcgcacca atggcagaca   2220
ataacgaagg tgccgacgga gtgggtaatg cctcaggaaa ttggcattgc gattccacat   2280
ggctgggcga cagagtcatt accaccagca cccgaacctg ggcccctgccc acctacaaca   2340
accacctcta caagcaaatc tccagtgaaa ctgcaggtag taccaacgac aacacctact   2400
tcggctacag caccccctgg ggtattttg actttaacag attccactgc cacttctcac   2460
cacgtgactg gcagcgactc atcaacaaca actgggggatt ccggcccaag aagctgcggt   2520
tcaagctctt caacatccag gtcaaggagg tcacgacgaa tgacggcgtt acgaccatcg   2580
ctaataacct taccagcacg attcaggtat tctcggactc ggaataccag ctgccgtacg   2640
tcctcggctc tgcgcaccag ggctgcctgc ctccgttccc ggcggacgtc ttcatgattc   2700
ctcagtacgg ctacctgact ctcaacaatg gcagtcagtc tgtgggacgt tcctccttct   2760
actgcctgga gtacttcccc tctcagatgc tgagaacggg caacaacttt gagttcagct   2820
acagcttcga ggacgtgcct ttccacagca gctacgcaca cagccagagc ctggaccggc   2880
tgatgaatcc cctcatcgac cagtacttgt actacctggc cagaacacag agtaacccag   2940
```

```
gaggcacagc tggcaatcgg gaactgcagt tttaccaggg cgggccttca actatggccg   3000
aacaagccaa gaattggtta cctggacctt gcttccggca acaaagagtc tccaaaacgc   3060
tggatcaaaa caacaacagc aactttgctt ggactggtgc caccaaatat cacctgaacg   3120
gcagaaactc gttggttaat cccggcgtcg ccatggcaac tcacaaggac gacgaggacc   3180 gcttttccc  atccagcgga gtcctgattt ttggaaaaac tggagcaact aacaaaacta   3240
cattggaaaa tgtgttaatg acaaatgaag aagaaattcg tcctactaat cctgtagcca   3300
cggaagaata cgggatagtc agcagcaact acaagcggc  taatactgca gcccagacac   3360
aagttgtcaa caaccaggga gccttacctg gcatggtctg gcagaaccgg gacgtgtacc   3420
tgcagggtcc catctgggcc aagattcctc acacggatgg caactttcac ccgtctcctt   3480
tgatgggcgg ctttggactt aaacatccgc ctcctcagat cctgatcaag aacactcccg   3540
ttcccgctaa tcctccggag gtgtttactc ctgccaagtt tgcttcgttc atcacacagt   3600
acagcaccgg acaagtcagc gtggaaatcg agtgggagct gcagaaggaa acagcaagc    3660 gctggaaccc ggagattcag tacacctcca actttgaaaa gcagactggt gtggactttg   3720
ccgttgacag ccagggtgtt tactctgagc ctcgccctat tggcactcgt tacctcaccc   3780
gtaatctgta aggcgcgcca ccggttgctt gttaatcaat aaaccgttta attcgtttca   3840
gttgaacttt ggtctctgcg tatttctttc ttatctagtt tccatgctct aggatccact   3900
agtaacggcc gccagtgtgc tggaattcgg ctttgtagtt aatgattaac cgccatgct   3960 acttatctac gtagccatgc tctagaggtc ctgtattaga ggtcacgtga gtgttttgcg   4020
acattttgcg acaccatgtg gtcacgctgg gtatttaagc ccgagtgagc acgcagggtc   4080
tccattttga agcgggaggt ttgaacgcgc agccgccaag ccgaattctg cagatatcca   4140
aacactggcg gccgctcgac tagagcggcc gccaccgcgg tggagctcca gcttttgttc   4200
cctttagtga gggttaattg cgcgcttggc gtaatcatgg tcatagctgt ttcctgtgtg   4260
aaattgttat ccgctcacaa ttccacacaa catacgagcc ggaagcataa agtgtaaagc   4320
ctggggtgcc taatgagtga gctaactcac attaattgcg ttgcgctcac tgcccgcttt   4380
ccagtcggga aacctgtcgt gccagctgca ttaatgaatc ggccaacgcg cggggagagg   4440
cggtttgcgt attgggcgct cttccgcttc ctcgctcact gactcgctgc gctcggtcgt   4500
tcggctgcgg cgagcggtat cagctcactc aaaggcggta atacggttat ccacagaatc   4560
aggggataac gcaggaaaga acatgtgagc aaaaggccag caaaaggcca ggaaccgtaa   4620
aaaggccgcg ttgctggcgt ttttccatag gctccgcccc cctgacgagc atcacaaaaa   4680
tcgacgctca agtcagaggt ggcgaaaccc gacaggacta taaagatacc aggcgtttcc   4740
ccctggaagc tccctcgtgc gctctcctgt tccgaccctg ccgcttaccg gatacctgtc   4800
cgcctttctc ccttcgggaa gcgtggcgct ttctcatagc tcacgctgta ggtatctcag   4860
ttcggtgtag tcgttcgctc caagctggg  ctgtgtgcac gaaccccccg ttcagcccga   4920
ccgctgcgcc ttatccggta actatcgtct tgagtccaac ccggtaagac acgacttatc   4980
gccactggca gcagccactg gtaacaggat tagcagagcg aggtatgtag gcggtgctac   5040
agagttcttg aagtggtggc ctaactacgg ctacactaga agaacagtat ttggtatctg   5100
cgctctgctg aagccagtta ccttcggaaa aagagttggt agctcttgat ccggcaaaca   5160
aaccaccgct ggtagcggtg gtttttttgt ttgcaagcag cagattacgc gcagaaaaaa   5220
aggatctcaa gaagatcctt tgatctttc  tacggggtct gacgctcagt ggaacgaaaa   5280
```

```
ctcacgttaa gggattttgg tcatgagatt atcaaaaagg atcttcacct agatccttt   5340
aaattaaaaa tgaagtttta aatcaatcta aagtatatat gagtaaactt ggtctgacag   5400
ttaccaatgc ttaatcagtg aggcacctat ctcagcgatc tgtctatttc gttcatccat   5460
agttgcctga ctccccgtcg tgtagataac tacgatacgg gagggcttac catctggccc   5520
cagtgctgca atgataccgc gagacccacg ctcaccggct ccagatttat cagcaataaa   5580
ccagccagcc ggaagggccg agcgcagaag tggtcctgca actttatccg cctccatcca   5640
gtctattaat tgttgccggg aagctagagt aagtagttcg ccagttaata gtttgcgcaa   5700
cgttgttgcc attgctacag gcatcgtggt gtcacgctcg tcgtttggta tggcttcatt   5760
cagctccggt tcccaacgat caaggcgagt tacatgatcc cccatgttgt gcaaaaaagc   5820
ggttagctcc ttcggtcctc cgatcgttgt cagaagtaag ttggccgcag tgttatcact   5880
catggttatg gcagcactgc ataattctct tactgtcatg ccatccgtaa gatgcttttc   5940
tgtgactggt gagtactcaa ccaagtcatt ctgagaatag tgtatgcggc gaccgagttg   6000
ctcttgcccg gcgtcaatac gggataatac cgcgccacat agcagaactt taaaagtgct   6060
catcattgga aaacgttctt cggggcgaaa actctcaagg atcttaccgc tgttgagatc   6120
cagttcgatg taacccactc gtgcacccaa ctgatcttca gcatctttta ctttcaccag   6180
cgtttctggg tgagcaaaaa caggaaggca aaatgccgca aaaaagggaa taagggcgac   6240
acggaaatgt tgaatactca tactcttcct ttttcaatat tattgaagca tttatcaggg   6300
ttattgtctc atgagcggat acatatttga atgtatttag aaaaataaac aaataggggt   6360
tccgcgcaca tttccccgaa aagtgccacc taaattgtaa gcgttaatat tttgttaaaa   6420
ttcgcgttaa attttgtta aatcagctca ttttttaacc aataggccga atcggcaaa   6480
atcccttata aatcaaaaga atagaccgag atagggttga gtgttgttcc agtttggaac   6540
aagagtccac tattaaagaa cgtggactcc aacgtcaaag ggcgaaaaac cgtctatcag   6600
ggcgatggcc cactacgtga accatcaccc taatcaagtt ttttggggtc gaggtgccgt   6660
aaagcactaa atcggaaccc taaagggagc ccccgattta gagcttgacg gggaaagccg   6720
gcgaacgtgg cgagaaagga agggaagaaa gcgaaaggag cgggcgctag gcgctggca   6780
agtgtagcgg tcacgctgcg cgtaaccacc acacccgccg cgcttaatgc gccgctacag   6840
ggcgcgtccc attcgccatt caggctcgcg aactgtggg aagggcgatc ggtgcgggcc   6900
tcttcgctat tacgccagct ggcgaaaggg ggatgtgctg caaggcgatt aagttgggta   6960
acgccagggt tttcccagtc acgacgttgt aaaacgacgg ccagtgagcg cgcgtaatac   7020
gactcactat agggcgaatt gggtaccggg cccccctcg aggtcgacgg tatcggggga   7080
gctcgcaggg tctccatttt gaagcgggag gtttgaacgc gcagccgcca tgccggggtt   7140
ttacgagatt gtgattaagg tccccagcga ccttgacgag catctgcccg gcatttctga   7200
cagctttgtg aactgggtgg ccgagaagga atgggagttg ccgccagatt ctgacatgga   7260
tctgaatctg attgagcagg cacccctgac cgtggccgag aagctgcagc gcgactttct   7320
gacggaatgg cgccgtgtga gtaaggcccc ggaggctctt ttctttgtgc aatttgagaa   7380
gggagagagc tacttccaca tgcacgtgct cgtggaaacc accggggtga aatc          7434
```

<210> SEQ ID NO 6
<211> LENGTH: 11569
<212> TYPE: DNA
<213> ORGANISM: Artificial Sequence
<220> FEATURE:
<223> OTHER INFORMATION: Coding Strand of Plasmid pHelper-Kan

<400> SEQUENCE: 6

```
ggtacccaac tccatgctta acagtcccca ggtacagccc accctgcgtc gcaaccagga      60
acagctctac agcttcctgg agcgccactc gccctacttc cgcagccaca gtgcgcagat     120
taggagcgcc acttcttttt gtcacttgaa aaacatgtaa aaataatgta ctaggagaca     180
cttttcaataa aggcaaatgt ttttatttgt acactctcgg gtgattattt acccccccacc  240
cttgccgtct gcgccgttta aaatcaaag gggttctgcc gcgcatcgct atgcgccact     300
ggcagggaca cgttgcgata ctggtgttta gtgctccact taaactcagg cacaaccatc    360
cgcggcagct cggtgaagtt ttcactccac aggctgcgca ccatcaccaa cgcgtttagc    420
aggtcgggcg ccgatatctt gaagtcgcag ttggggcctc cgccctgcgc gcgcgagttg    480
cgatacacag ggttgcagca ctggaacact atcagcgccg ggtggtgcac gctgccagc     540
acgctcttgt cggagatcag atccgcgtcc aggtcctccg cgttgctcag ggcgaacgga    600
gtcaactttg gtagctgcct tcccaaaaag ggtgcatgcc caggctttga gttgcactcg    660
caccgtagtg gcatcagaag gtgaccgtgc ccggtctggg cgttaggata cagcgcctgc    720
atgaaagcct tgatctgctt aaaagccacc tgagcctttg cgccttcaga gaagaacatg    780
ccgcaagact tgccggaaaa ctgattggcc ggacaggccg cgtcatgcac gcagcacctt    840
gcgtcggtgt tggagatctg caccacattt cggcccacc ggttcttcac gatcttggcc     900
ttgctagact gctccttcag cgcgcgctgc ccgttttcgc tcgtcacatc catttcaatc    960
acgtgctcct tatttatcat aatgctcccg tgtagacact taagctcgcc ttcgatctca   1020
gcgcagcggt gcagccacaa cgcgcagccc gtgggctcgt ggtgcttgta ggttacctct   1080
gcaaacgact gcaggtacgc ctgcaggaat cgccccatca tcgtcacaaa ggtcttgttg   1140
ctggtgaagg tcagctgcaa cccgcggtgc tcctcgttta gccaggtctt gcatacggcc   1200
gccagagctt ccacttggtc aggcagtagc ttgaagtttg cctttagatc gttatccacg   1260
tggtacttgt ccatcaacgc gcgcgcagcc tccatgccct tctcccacgc agacacgatc   1320
ggcaggctca gcgggtttat caccgtgctt tcactttccg cttcactgga ctcttccttt   1380
tcctcttgcg tccgcatacc ccgcgccact gggtcgtctt cattcagccg ccgcaccgtg   1440
cgcttacctc ccttgccgtg cttgattagc accggtgggt tgctgaaacc caccatttgt   1500
agcgccacat cttctctttc ttcctcgctg tccacgatca cctctgggga tggcgggcgc   1560
tcgggcttgg gagaggggcg cttctttttc tttttggacg caatggccaa atccgccgtc   1620
gaggtcgatg gccgcgggct gggtgtgcgc ggcaccagcg catcttgtga cgagtcttct   1680
tcgtcctcgg actcgagacg ccgcctcagc cgcttttttg ggggcgcgcg gggaggcggc   1740
ggcgacggcg acgggacga cacgtcctcc atggttggtg gacgtcgcgc cgcaccgcgt    1800
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
```

```
tcaccgcgcg tacccccaa  acgccaagaa aacggcacat gcgagcccaa cccgcgcctc   2340
aacttctacc ccgtatttgc cgtgccagag gtgcttgcca cctatcacat cttttttccaa  2400 aactgcaaga taccctatc  ctgccgtgcc aaccgcagcc gagcggacaa gcagctggcc   2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt cacccacttt gcctacccgg cacttaacct acccccaag   2700 gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg ggcaaaacgt gcttcattca acgctcaagg gcgaggcgcg ccgcgactac   3120
gtccgcgact gcgtttactt atttctgtgc tacacctggc aaacggccat gggcgtgtgg   3180
cagcaatgcc tggaggagcg caacctaaag gagctgcaga gctgctaaa  gcaaaacttg   3240 aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa cttatcccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgccaaga gtttctgcta   3900
cgaaagggac gggggggttta cctggacccc cagtccggcg aggagctcaa cccaatcccc   3960
ccgccgccgc agcccctatca gcagccgcgg gcccttgctt cccaggatgg cacccaaaaa   4020
gaagctgcag ctgccgccgc cgccaccac ggacgaggag gaatactggg acagtcaggc   4080
agaggaggtt ttggacgagg aggaggagat gatggaagac tggacagcc tagacgaagc   4140 ttccgaggcc gaagaggtgt cagacgaaac accgtcaccc tcggtcgcat tcccctcgcc   4200
ggcgccccag aaattggcaa ccgttccag  catcgctaca acctccgctc ctcaggcgcc   4260
gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgcttttcttc tctaccatca cggcgtggcc ttccccgta  acatcctgca   4500 ttactaccgt catctctaca gccccctactg caccggcggc agcggcagcg gcagcaacag   4560
cagcggtcac acagaagcaa aggcgaccgg atagcaagac tctgacaaag cccaagaaat   4620
ccacagcggc ggcagcagca ggaggaggag cgctgcgtct ggcgcccaac gaacccgtat   4680
```

| | |
|---|---|
| cgacccgcga gcttagaaat aggattttc ccactctgta tgctatattt caacaaagca | 4740 |
| ggggccaaga acaagagctg aaaataaaaa acaggtctct gcgctccctc acccgcagct | 4800 |
| gcctgtatca caaagcgaa gatcagcttc ggcgcacgct ggaagacgcg gaggctctct | 4860 |
| tcagcaaata ctgcgcgctg actcttaagg actagtttcg cgccctttct caaatttaag | 4920 |
| cgcgaaaact acgtcatctc cagcggccac acccggcgcc agcacctgtc gtcagcgcca | 4980 |
| ttatgagcaa ggaaattccc acgccctaca tgtggagtta ccagccacaa atgggacttg | 5040 |
| cggctggagc tgcccaagac tactcaaccc gaataaacta catgagcgcg gaccccaca | 5100 |
| tgatatcccg ggtcaacgga atccgcgccc accgaaaccg aattctcctc gaacaggcgg | 5160 |
| ctattaccac cacacctcgt aataaccta atcccgtag ttggcccgct gccctggtgt | 5220 |
| accaggaaag tcccgctccc accactgtgg tacttcccag agacgcccag gccgaagttc | 5280 |
| agatgactaa ctcaggggcg cagcttgcgg gcggctttcg tcacagggtg cggtcgcccg | 5340 |
| ggcgttttag ggcggagtaa cttgcatgta ttgggaattg tagttttttt aaaatgggaa | 5400 |
| gtgacgtatc gtgggaaaac ggaagtgaag atttgaggaa gttgtgggtt ttttggctt | 5460 |
| cgtttctggg cgtaggttcg cgtgcggttt tctgggtgtt ttttgtggac tttaaccgtt | 5520 |
| acgtcatttt ttagtcctat atatactcgc tctgtacttg gccctttta cactgtgact | 5580 |
| gattgagctg gtgccgtgtc gagtggtgtt ttttaatagg ttttttttact ggtaaggctg | 5640 |
| actgttatgg ctgccgctgt ggaagcgctg tatgttgttc tggagcggga gggtgctatt | 5700 |
| ttgcctaggc aggagggttt ttcaggtgtt tatgtgtttt tctctcctat taattttgtt | 5760 |
| atacctccta tgggggctgt aatgttgtct ctacgcctgc gggtatgtat tccccgggc | 5820 |
| tatttcggtc gcttttagc actgaccgat gttaaccaac ctgatgtgtt taccgagtct | 5880 |
| tacattatga ctccggacat gaccgaggaa ctgtcggtgg tgcttttaa tcacggtgac | 5940 |
| cagttttttt acgtcacgc cggcatggcc gtagtccgtc ttatgcttat aagggttgtt | 6000 |
| tttcctgttg taagacaggc ttctaatgtt taaatgtttt ttttttgtt attttatttt | 6060 |
| gtgtttaatg caggaacccg cagacatgtt tgagagaaaa atggtgtctt tttctgtggt | 6120 |
| ggttccggaa cttacctgcc tttatctgca tgagcatgac tacgatgtgc ttgcttttt | 6180 |
| gcgcgaggct ttgcctgatt ttttgagcag caccttgcat tttatatcgc cgcccatgca | 6240 |
| acaagcttac ataggggcta cgctggttag catagctccg agtatgcgtg tcataatcag | 6300 |
| tgtgggttct tttgtcatgg ttcctggcgg ggaagtggcc gcgctggtcc gtgcagacct | 6360 |
| gcacgattat gttcagctgg ccctgcgaag ggacctacgg gatcgcggta ttttgttaa | 6420 |
| tgttccgctt ttgaatctta tacaggtctg tgaggaacct gaattttgc aatcatgatt | 6480 |
| cgctgcttga ggctgaaggt ggagggcgct ctggagcaga ttttacaat ggccggactt | 6540 |
| aatattcggg atttgcttag agacatattg ataaggtggc gagatgaaaa ttatttgggc | 6600 |
| atggttgaag gtgctggaat gtttatagag gagattcacc ctgaagggtt tagcctttac | 6660 |
| gtccacttgg acgtgagggc agtttgcctt ttggaagcca ttgtgcaaca tcttacaaat | 6720 |
| gccattatct gttctttggc tgtagagttt gaccacgcca ccggagggga gcgcgttcac | 6780 |
| ttaatagatc ttcattttga ggttttggat aatcttttgg aataaaaaaa aaaaacatg | 6840 |
| gttcttccag ctcttcccgc tcctcccgtg tgtgactcgc agaacgaatg tgtaggttgg | 6900 |
| ctgggtgtgg cttattctgc ggtggtggat gttatcaggg cagcggcgca tgaaggagtt | 6960 |
| tacatagaac ccgaagccag ggggcgcctg gatgctttga gagagtggat atactacaac | 7020 |

```
tactacacag agcgagctaa gcgacgagac cggagacgca gatctgtttg tcacgcccgc    7080
acctggtttt gcttcaggaa atatgactac gtccggcgtt ccatttggca tgacactacg    7140
accaacacga tctcggttgt ctcggcgcac tccgtacagt agggatcgcc tacctccttt    7200
tgagacagag acccgcgcta ccatactgga ggatcatccg ctgctgcccg aatgtaacac    7260
tttgacaatg cacaacgtga gttacgtgcg aggtcttccc tgcagtgtgg gatttacgct    7320
gattcaggaa tgggttgttc cctgggatat ggttctgacg cgggaggagc ttgtaatcct    7380
gaggaagtgt atgcacgtgt gcctgtgttg tgccaacatt gatatcatga cgagcatgat    7440
gatccatggt tacgagtcct gggctctcca ctgtcattgt tccagtcccg gttccctgca    7500
gtgcatagcc ggcgggcagg ttttggccag ctggtttagg atggtggtgg atggcgccat    7560
gtttaatcag aggtttatat ggtaccggga ggtggtgaat tacaacatgc caaaagaggt    7620
aatgtttatg tccagcgtgt ttatgagggg tcgccactta atctacctgc gcttgtggta    7680
tgatggccac gtgggttctg tggtccccgc catgagcttt ggatacagcg ccttgcactg    7740
tgggattttg aacaatattg tggtgctgtg ctgcagttac tgtgctgatt taagtgagat    7800
cagggtgcgc tgctgtgccc ggaggacaag gcgtctcatg ctgcgggcgg tgcgaatcat    7860
cgctgaggag accactgcca tgttgtattc ctgcaggacg gagcggcggc ggcagcagtt    7920
tattcgcgcg ctgctgcagc accaccgccc tatcctgatg cacgattatg actctacccc    7980
catgtaggcg tggacttccc cttcgccgcc cgttgagcaa ccgcaagttg gacagcagcc    8040
tgtggctcag cagctggaca gcgacatgaa cttaagcgag ctgcccgggg agtttattaa    8100
tatcactgat gagcgtttgg ctcgacagga aaccgtgtgg aatataacac ctaagaatat    8160
gtctgttacc catgatatga tgcttttttaa ggccagccgg ggagaaagga ctgtgtactc    8220
tgtgtgttgg gagggaggtg gcaggttgaa tactagggtt ctgtgagttt gattaaggta    8280
cggtgatcaa tataagctat gtggtggtgg ggctatacta ctgaatgaaa aatgacttga    8340
aattttctgc aattgaaaaa taaacacgtt gaaacataac atgcaacagg ttcacgattc    8400
tttattcctg ggcaatgtag gagaaggtgt aagagttggt agcaaaagtt tcagtggtgt    8460
attttccact ttcccaggac catgtaaaag acatagagta agtgcttacc tcgctagttt    8520
ctgtggattc actagaatcg atgtaggatg ttgcccctcc tgacgcggta ggagaagggg    8580
agggtgccct gcatgtctgc cgctgctctt gctcttgccg ctgctgagga gggggcgca    8640 tctgccgcag caccggatgc atctgggaaa agcaaaaaag gggctcgtcc ctgtttccgg    8700
aggaatttgc aagcggggtc ttgcatgacg gggaggcaaa cccccgttcg ccgcagtccg    8760
gccggcccga gactcgaacc gggggtcctg cgactcaacc cttggaaaat aaccctccgg    8820
ctacagggag cgagccactt aatgctttcg ctttccagcc taaccgctta cgccgcgcgc    8880
ggccagtggc caaaaaagct agcgcagcag ccgccgcgcc tggaaggaag ccaaaaggag    8940
cgctcccccg ttgtctgacg tcgcacacct gggttcgaca cgcgggcggt aaccgcatgg    9000
atcacggcgg acgccggat ccggggttcg aaccccggtc gtccgccatg atacccttgc    9060
gaatttatcc accagaccac ggaagagtgc ccgcttacag gctctccttt tgcacggtct    9120
agagcgtcaa cgactgcgca cgcctcaccg gccagagcgt cccgaccatg gagcactttt    9180
tgccgctgcg caacatctgg aaccgcgtcc gcgactttcc gcgcgcctcc accaccgccg    9240
ccggcatcac ctgatgtgtcc aggtacatct acggattacg tcgacgttta aaccatatga    9300
tcagctcact caaaggcggt aatacggtta tccacagaat caggggataa cgcaggaaag    9360
aacatgtgag caaaaggcca gcaaaaggcc aggaaccgta aaaaggccgc gttgctggcg    9420
```

```
tttttccata ggctccgccc ccctgacgag catcacaaaa atcgacgctc aagtcagagg    9480
tggcgaaacc cgacaggact ataaagatac caggcgtttc ccctggaag ctccctcgtg     9540
cgctctcctg ttccgaccct gccgcttacc ggatacctgt ccgcctttct cccttcggga    9600
agcgtggcgc tttctcatag ctcacgctgt aggtatctca gttcggtgta ggtcgttcgc    9660
tccaagctgg gctgtgtgca cgaaccccc gttcagcccg accgctgcgc cttatccggt      9720
aactatcgtc ttgagtccaa cccggtaaga cacgacttat cgccactggc agcagccact    9780
ggtaacagga ttagcagagc gaggtatgta ggcggtgcta cagagttctt gaagtggtgg    9840
cctaactacg gctacactag aagaacagta tttggtatct gcgctctgct gaagccagtt    9900
accttcggaa aaagagttgg tagctcttga tccggcaaac aaaccaccgc tggtagcggt    9960
ggtttttttg tttgcaagca gcagattacg cgcagaaaaa aaggatctca agaagatcct   10020
ttgatctttt ctacggggtc tgacgctcag tggaacgaaa actcacgtta agggattttg   10080
gtcatgagat tatcaaaaag gatcttcacc tagatccttt taaattaaaa atgaagtttt   10140
aaatcaatct aaagtatata tgagtaaact tggtctgaca gtcagaagaa ctcgtcaaga   10200
aggcgataga aggcgatgcg ctgcgaatcg ggagcggcga taccgtaaag cacgaggaag   10260
cggtcagccc attcgccgcc aagctcttca gcaatatcac gggtagccaa cgctatgtcc   10320
tgatagcggt ccgccacacc cagccggcca cagtcgatga atccagaaaa gcggccattt   10380
tccaccatga tattcggcaa gcaggcatcg ccatgggtca cgacgagatc ctcgccgtcg   10440
ggcatgctcg ccttgagcct ggcgaacagt tcggctggcg cgagccctg atgctcttcg    10500
tccagatcat cctgatcgac aagaccggct tccatccgag tacgtgctcg ctcgatgcga   10560
tgtttcgctt ggtggtcgaa tgggcaggta gccggatcaa gcgtatgcag ccgccgcatt   10620
gcatcagcca tgatggatac tttctcggca ggagcaaggt gagatgacag gagatcctgc   10680
cccggcactt cgcccaatag cagccagtcc cttcccgctt cagtgacaac gtcgagtaca   10740
gctgcgcaag gaacgcccgt cgtggccagc cacgatagcc gcgctgcctc gtcttgcagt   10800
tcattcaggg caccggacag gtcggtcttg acaaaaagaa ccgggcgccc ctgcgctgac   10860
agccggaaca cggcggcatc agagcagccg attgtctgtt gtgcccagtc atagccgaat   10920
agcctctcca cccaagcggc cggagaacct gcgtgcaatc catcttgttc aatcatactc   10980
ttcctttttc aatattattg aagcatttat cagggttatt gtctcatgag cggatacata   11040
tttgaatgta tttagaaaaa taaacaaata ggggttccgc gcacatttcc ccgaaaagtg   11100
ccacctaaat tgtaagcgtt aatattttgt aaaattcgc gttaaatttt tgttaaatca    11160
gctcattttt taaccaatag gccgaaatcg gcaaaatccc ttataaatca aagaatagac  11220
ccgagatagg gttgagtgtt gttccagttt ggaacaagag tccactatta agaacgtgg    11280
actccaacgt caaagggcga aaaccgtct atcagggcga tggcccacta cgtgaaccat   11340
caccctaatc aagttttttg gggtcgaggt gccgtaaagc actaaatcgg aaccctaaag   11400
ggagccccg atttagagct tgacggggaa agccggcgaa cgtggcgaga aaggaaggga    11460
agaaagcgaa aggagcgggc gctagggcgc tggcaagtgt agcggtcacg ctgcgcgtaa   11520
ccaccacacc cgccgcgctt aatgcgccgc tacagggcgc gatggatcc                11569
```

<210> SEQ ID NO 7
<211> LENGTH: 5030
<212> TYPE: DNA
<213> ORGANISM: Artificial Sequence
<220> FEATURE:

<223> OTHER INFORMATION: Coding Strand of Plasmid pAV-CMV-EGFP

<400> SEQUENCE: 7

```
cctgcaggca gctgcgcgct cgctcgctca ctgaggccgc ccgggcgtcg ggcgaccttt      60
ggtcgcccgg ccctccagtg agcgagcgcg cagagaggga gtggccaact ccatcactag     120
gggttcctgc ggccgcacgc gtctagttat taatagtaat cgaattcgtg ttactcataa     180
ctagtaaggt cgggcaggaa gagggcctat ttcccatgat tccttcatat ttgcatatac     240
gatacaaggc tgttagagag ataattagaa ttaatttgac tgtaaacaca agatattag      300
tacaaaatac gtgacgtaga agtaataat ttcttgggta gtttgcagtt ttaaaattat      360
gttttaaaat ggactatcat atgcttaccg taacttgaaa gtatttcgat ttcttgggtt     420
tatatatctt gtggaaagga cgcgggatcc actggaccag gcagcagcgt cagaagactt     480
ttttggaaaa gcttgactag taatactgta atagtaatca attacggggt cattagttca     540
tagcccatat atggagttcc gcgttacata acttacggta aatggcccgc ctggctgacc     600
gcccaacgac ccccgcccat tgacgtcaat aatgacgtat gttcccatag taacgccaat     660
agggactttc cattgacgtc aatgggtgga gtatttacgg taaactgccc acttggcagt     720
acatcaagtg tatcatatgc caagtacgcc ccctattgac gtcaatgacg gtaaatggcc     780
cgcctggcat tatgcccagt acatgacctt atgggacttt cctacttggc agtacatcta     840
cgtattagtc atcgctatta ccatggtgat gcggttttgg cagtacatca atgggcgtgg     900
atagcggttt gactcacggg gatttccaag tctccacccc attgacgtca atgggagttt     960
gttttgcacc aaaatcaacg ggactttcca aaatgtcgta acaactccgc cccattgacg    1020
caaatgggcg gtaggcgtgt acggtgggag gtctatataa gcagagctgg tttagtgaac    1080
cgtcagatcc gctagagatc cggtaccgag gagatctgcc gccgcgatcg ccggcgcgcc    1140
agatctcacg cttaactagc tagcggaccg acgcgtacgc ggccgctcga gatggtgagc    1200
aagggcgagg agctgttcac cggggtggtg cccatcctgg tcgagctgga cggcgacgta    1260
aacggccaca gttcagcgt gtccggcgag ggcgagggcg atgccaccta cggcaagctg    1320
accctgaagt tcatctgcac caccggcaag ctgcccgtgc cctggcccac cctcgtgacc    1380
accctgacct acggcgtgca gtgcttcagc cgctaccccg accacatgaa gcagcacgac    1440
ttcttcaagt ccgccatgcc cgaaggctac gtccaggagc gcaccatctt cttcaaggac    1500
gacggcaact acaagacccg cgccgaggtg aagttcgagg gcgacaccct ggtgaaccgc    1560
atcgagctga agggcatcga cttcaaggag gacggcaaca tcctggggca caagctggag    1620
tacaactaca acagccacaa cgtctatatc atggccgaca agcagaagaa cggcatcaag    1680
gtgaacttca agatccgcca caacatcgag gacggcagcg tgcagctcgc cgaccactac    1740
cagcagaaca cccccatcgg cgacggcccc gtgctgctgc ccgacaacca ctacctgagc    1800
acccagtccg ccctgagcaa agaccccaac gagaagcgcg atcacatggt cctgctggag    1860
ttcgtgaccg ccgccgggat cactctcggc atggacgagc tgtacaagta agtcgaggat    1920
tataaggatg acgacgataa attcgtcgag caccaccacc accaccacta ataaggttta    1980
tccgatccac cggatctaga taagatatcc gatccaccgg atctagataa ctgatcataa    2040
tcagccatac cacatttgta gaggttttac ttgctttaaa aaacctccca cacctccccc    2100
tgaacctgaa acataaaatg aatgcaattg ttgttgttaa cttgtttatt gcagcttata    2160
atggttacaa ataaagcaat agcatcacaa atttcacaaa taaagcattt ttttcactgc    2220
attctagttg tggtttgtcc aaactcatca atgtatctta acgcggtaac cacgtgcgga    2280
```

```
ccgagcggcc gcaggaaccc ctagtgatgg agttggccac tccctctctg cgcgctcgct    2340
cgctcactga ggccgggcga ccaaaggtcg cccgacgccc gggctttgcc cgggcggcct    2400
cagtgagcga gcgagcgcgc agctgcctgc aggggcgcct gatgcggtat tttctcctta    2460
cgcatctgtg cggtatttca caccgcatac gtcaaagcaa ccatagtacg cgccctgtag    2520
cggcgcatta agcgcggcgg gtgtggtggt tacgcgcagc gtgaccgcta cacctgccag    2580
cgccttagcg cccgctcctt tcgctttctt cccttccttt ctcgccacgt tcgccggctt    2640
tccccgtcaa gctctaaatc gggggctccc tttagggttc cgatttagtg ctttacggca    2700
cctcgacccc aaaaaacttg atttgggtga tggttcacgt agtgggccat cgccctgata    2760
gacggttttt cgccctttga cgttggagtc cacgttcttt aatagtggac tcttgttcca    2820
aactggaaca cactcaacc ctatctcggg ctattctttt gatttataag gattttgcc    2880
gatttcggcc tattggttaa aaatgagct gatttaacaa aaatttaacg cgaattttaa    2940
caaaatatta cgtttacaa ttttatggtg cactctcagt acaatctgct ctgatgccgc    3000
atagttaagc cagccccgac acccgccaac acccgctgac gcgccctgac gggcttgtct    3060
gctcccggca tccgcttaca gacaagctgt gaccgtctcc gggagctgca tgtgtcagag    3120
gttttcaccg tcatcaccga aacgcgcgag acgaaagggc ctcgtgatac gcctattttt    3180
ataggttaat gtcatgataa taatggtttc ttagacgtca ggtggcactt ttcggggaaa    3240
tgtgcgcgga accctatttt gtttattttt ctaaatacat tcaaatatgt atccgctcat    3300
gagacaataa ccctgataaa tgcttcaata atattgaaaa aggaagagta tgagtattca    3360
acatttccgt gtcgccctta ttccctttt tgcggcattt tgccttcctg tttttgctca    3420
cccagaaacg ctggtgaaag taaaagatgc tgaagatcag ttgggtgcac gagtgggtta    3480
catcgaactg gatctcaaca gcggtaagat ccttgagagt tttcgccccg aagaacgttt    3540
tccaatgatg agcacttta aagttctgct atgtggcgcg gtattatccc gtattgacgc    3600
cgggcaagag caactcggtc gccgcataca ctattctcag aatgacttgg ttgagtactc    3660
accagtcaca gaaaagcatc ttacggatgg catgacagta agagaattat gcagtgctgc    3720
cataaccatg agtgataaca ctgcggccaa cttacttctg acaacgatcg gaggaccgaa    3780
ggagctaacc gcttttttgc acaacatggg ggatcatgta actcgccttg atcgttggga    3840
accggagctg aatgaagcca taccaaacga cgagcgtgac accacgatgc ctgtagcaat    3900
ggcaacaacg ttgcgcaaac tattaactgg cgaactactt actctagctt cccggcaaca    3960
attaatagac tggatggagg cggataaagt tgcaggacca cttctgcgct cggcccttcc    4020
ggctggctgg tttattgctg ataaatctgg agccggtgag cgtgggtctc gcggtatcat    4080
tgcagcactg gggccagatg gtaagccctc ccgtatcgta gttatctaca cgacggggag    4140
tcaggcaact atggatgaac gaaatagaca gatcgctgag ataggtgcct cactgattaa    4200
gcattggtaa ctgtcagacc aagtttactc atatatactt tagattgatt taaaacttca    4260
tttttaattt aaaaggatct aggtgaagat cctttttgat aatctcatga ccaaaatccc    4320
ttaacgtgag ttttcgttcc actgagcgtc agaccccgta gaaaagatca aaggatcttc    4380
ttgagatcct ttttttctgc gcgtaatctg ctgcttgcaa acaaaaaaac caccgctacc    4440
agcggtggtt tgtttgccgg atcaagagct accaactctt tttccgaagg taactggctt    4500
cagcagagcg cagataccaa atactgtcct tctagtgtag ccgtagttag gccaccactt    4560
caagaactct gtagcaccgc ctacatacct cgctctgcta atcctgttac cagtggctgc    4620
```

| | |
|---|---:|
| tgccagtggc gataagtcgt gtcttaccgg gttggactca agacgatagt taccggataa | 4680 |
| ggcgcagcgg tcgggctgaa cggggggttc gtgcacacag cccagcttgg agcgaacgac | 4740 |
| ctacaccgaa ctgagatacc tacagcgtga gctatgagaa agcgccacgc ttcccgaagg | 4800 |
| gagaaaggcg gacaggtatc cggtaagcgg cagggtcgga acaggagagc gcacgaggga | 4860 |
| gcttccaggg ggaaacgcct ggtatcttta tagtcctgtc gggtttcgcc acctctgact | 4920 |
| tgagcgtcga ttttttgtgat gctcgtcagg ggggcggagc ctatggaaaa acgccagcaa | 4980 |
| cgcggccttt ttacggttcc tggccttttg ctggccttttt gctcacatgt | 5030 |

<210> SEQ ID NO 8
<211> LENGTH: 4742
<212> TYPE: DNA
<213> ORGANISM: Artificial Sequence
<220> FEATURE:
<223> OTHER INFORMATION: Coding Strand of Plasmid pAV-TBG-EGFP

<400> SEQUENCE: 8

| | |
|---|---:|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccggtc gcgtctagta ctagtaggtt aatttttaaa aagcagtcaa | 180 |
| aagtccaagt ggcccttggc agcatttact ctctctgttt gctctggtta ataatctcag | 240 |
| gagcacaaac attccagatc caggttaatt tttaaaaagc agtcaaaagt ccaagtggcc | 300 |
| cttggcagca tttactctct ctgtttgctc tggttaataa tctcaggagc acaaacattc | 360 |
| cagatccggc gcgccagggc tggaagctac ctttgacatc atttcctctg cgaatgcatg | 420 |
| tataatttct acagaaccta ttagaaagga tcacccagcc tctgcttttg tacaactttc | 480 |
| ccttaaaaaa ctgccaattc cactgctgtt tggcccaata gtgagaactt tttcctgctg | 540 |
| cctcttggtg cttttgccta tggcccctat tctgcctgct gaagacactc ttgccagcat | 600 |
| ggacttaaac ccctccagct ctgacaatcc tctttctctt ttgttttaca tgaagggtct | 660 |
| ggcagccaaa gcaatcactc aaagttcaaa ccttatcatt ttttgctttg ttcctcttgg | 720 |
| ccttggtttt gtacatcagc tttgaaaata ccatcccagg gttaatgctg gggttaattt | 780 |
| ataactaaga gtgctctagt tttgcaatac aggacatgct ataaaaatgg aaagatgttg | 840 |
| ctttctgaga gacaggtacc gaggagatct gccgccgcga tcgccaccat ggtgagcaag | 900 |
| ggcgaggagc tgttcaccgg ggtggtgccc atcctggtcg agctggacgg cgacgtaaac | 960 |
| ggccacaagt tcagcgtgtc cggcgagggc gagggcgatg ccacttacgg caagctgacc | 1020 |
| ctgaagttca tctgcaccac cggcaagctg cccgtgccct ggcccaccct cgtgaccacc | 1080 |
| ctgacctacg gcgtgcagtg cttcagccgc taccccgacc acatgaagca gcacgacttc | 1140 |
| ttcaagtccg ccatgcccga aggctacgtc caggagcgca ccatcttctt caaggacgac | 1200 |
| ggcaactaca agacccgcgc cgaggtgaag ttcgagggcg acaccctggt gaaccgcatc | 1260 |
| gagctgaagg gcatcgactt caaggaggac ggcaacatcc tggggcacaa gctggagtac | 1320 |
| aactacaaca gccacaacgt ctatatcatg gccgacaagc agaagaacgg catcaaggtg | 1380 |
| aacttcaaga tccgccacaa catcgaggac ggcagcgtgc agctcgccga ccactaccag | 1440 |
| cagaacaccc ccatcggcga cggccccgtg ctgctgcccg acaaccacta cctgagcacc | 1500 |
| cagtccgccc tgagcaaaga ccccaacgag aagcgcgatc acatggtcct gctggagttc | 1560 |
| gtgaccgccg ccgggatcac tctcggcatg gacgagctgt acaagtagac gcgtacgcgg | 1620 |
| ccgctcgagg attataagga tgacgacgat aaattcgtcg agcaccacca ccaccaccac | 1680 |

```
taataaggtt tatccgatcc accggatcta gataagatat ccgatccacc ggatctagat   1740
aactgatcat aatcagccat accacatttg tagaggtttt acttgcttta aaaaacctcc   1800
cacacctccc cctgaacctg aaacataaaa tgaatgcaat tgttgttgtt aacttgttta   1860
ttgcagctta taatggttac aaataaagca atagcatcac aaatttcaca aataaagcat   1920 tttttttcact gcattctagt tgtggtttgt ccaaactcat caatgtatct taacgcggta   1980
accacgtgcg gacccaacgg ccgcaggaac ccctagtgat ggagttggcc actccctctc   2040
tgcgcgctcg ctcgctcact gaggccgggc gaccaaaggt cgcccgacgc ccgggctttg   2100
cccgggcggc ctcagtgagc gagcgagcgc gcagctgcct gcaggggcgc ctgatgcggt   2160
attttctcct tacgcatctg tgcggtattt cacaccgcat acgtcaaagc aaccatagta   2220
cgcgccctgt agcggcacat taagcgcggc gggtgtggtg gttacgcgca gcgtgaccgc   2280
tacacctgcc agcgccttag cgcccgctcc tttcgctttc ttcccttcct ttctcgccac   2340
gttcgccggc tttccccgtc aagctctaaa tcggggggctc cctttagggt tccgatttag   2400
tgctttacgg cacctcgacc ccaaaaaact tgatttgggt gatggttcac gtagtgggcc   2460
atcgccctga tagacggttt ttcgcccttt gacgttggag tccacgttct ttaatagtgg   2520
actcttgttc caaactggaa caacactcaa ctctatctcg ggctattctt ttgatttata   2580
agggattttg ccgatttcgg tctattggtt aaaaaatgag ctgatttaac aaaaatttaa   2640
cgcgaatttt aacaaaatat taacgtttac aattttatgg tgcactctca gtacaatctg   2700
ctctgatgcc gcatagttaa gccagccccg acacccgcca cacccgctg acgcgccctg   2760 acgggcttgt ctgctcccgg catccgctta cagacaagct gtgaccgtct ccgggagctg   2820
catgtgtcag aggttttcac cgtcatcacc gaaacgcgcg agacgaaagg gcctcgtgat   2880
acgcctattt ttataggtta atgtcatgat aataatggtt tcttagacgt caggtggcac   2940
ttttcgggga atgtgcgcg gaaccccctat ttgtttattt ttctaaatac attcaaatat   3000
gtatccgctc atgagacaat aaccctgata aatgcttcaa taatattgaa aaaggaagag   3060
tatgagtatt caacatttcc gtgtcgccct tattcccttt tttgcggcat tttgccttcc   3120
tgtttttgct cacccagaaa cgctggtgaa agtaaaagat gctgaagatc agttgggtgc   3180
acgagtgggt tacatcgaac tggatctcaa cagcggtaag atccttgaga gttttcgccc   3240
cgaagaacgt tttccaatga tgagcacttt taaagttctg ctatgtggcg cggtattatc   3300
ccgtattgac gccgggcaag agcaactcgg tcgccgcata cactattctc agaatgactt   3360
ggttgagtac tcaccagtca cagaaaagca tcttacggat ggcatgacag taagagaatt   3420
atgcagtgct gccataacca tgagtgataa cactgcggcc aacttacttc tgacaacgat   3480
cggaggaccg aaggagctaa ccgcttttttt gcacaacatg ggggatcatg taactcgcct   3540
tgatcgttgg gaaccggagc tgaatgaagc cataccaaac gacgagcgtg acaccacgat   3600
gcctgtagca atggcaacaa cgttgcgcaa actattaact ggcgaactac ttactctagc   3660
ttcccggcaa caattaatag actggatgga ggcggataaa gttgcaggac cacttctgcg   3720
ctcggccctt ccggctggct ggtttattgc tgataaatct ggagccggtg agcgtgggtc   3780
tcgcggtatc attgcagcac tggggccaga tggtaagccc tcccgtatcg tagttatcta   3840
cacgacgggg agtcaggcaa ctatggatga acgaaataga cagatcgctg agataggtgc   3900
ctcactgatt aagcattggt aactgtcaga ccaagtttac tcatatatac tttagattga   3960
tttaaaactt cattttttaat ttaaaaggat ctaggtgaag atccttttttg ataatctcat   4020
```

-continued

```
gaccaaaatc ccttaacgtg agttttcgtt ccactgagcg tcagaccccg tagaaaagat    4080
caaaggatct tcttgagatc ctttttttct gcgcgtaatc tgctgcttgc aaacaaaaaa    4140
accaccgcta ccagcggtgg tttgtttgcc ggatcaagag ctaccaactc ttttccgaa     4200 ggtaactggc ttcagcagag cgcagatacc aaatactgtt cttctagtgt agccgtagtt    4260
aggccaccac ttcaagaact ctgtagcacc gcctacatac ctcgctctgc taatcctgtt    4320
accagtggct gctgccagtg gcgataagtc gtgtcttacc gggttggact caagacgata    4380
gttaccggat aaggcgcagc ggtcgggctg aacggggggt tcgtgcacac agcccagctt    4440
ggagcgaacg acctacaccg aactgagata cctacagcgt gagctatgag aaagcgccac    4500
gcttcccgaa gggagaaagg cggacaggta tccggtaagc ggcagggtcg aacaggaga    4560 gcgcacgagg gagcttccag ggggaaacgc ctggtatctt tatagtcctg tcgggtttcg    4620
ccacctctga cttgagcgtc gatttttgtg atgctcgtca gggggggcgga gcctatggaa    4680 aaacgccagc aacgcggcct ttttacggtt cctggccttt tgctggcctt ttgctcacat    4740
gt                                                                   4742
```

<210> SEQ ID NO 9
<211> LENGTH: 131
<212> TYPE: DNA
<213> ORGANISM: adeno-associated virus 1
<220> FEATURE:
<221> NAME/KEY: misc_feature
<222> LOCATION: (1)..(131)
<223> OTHER INFORMATION: P5 Promoter of AAV1

<400> SEQUENCE: 9

```
ggtcctgtat tagctgtcac gtgagtgctt ttgcgacatt ttgcgacacc acgtggccat    60
ttagggtata tatggccgag tgagcgagca ggatctccat tttgaccgcg aaatttgaac   120
gagcagcagc c                                                        131
```

<210> SEQ ID NO 10
<211> LENGTH: 131
<212> TYPE: DNA
<213> ORGANISM: adeno-associated virus 2
<220> FEATURE:
<221> NAME/KEY: misc_feature
<222> LOCATION: (1)..(131)
<223> OTHER INFORMATION: P5 Promoter of AAV2

<400> SEQUENCE: 10

```
ggtcctgtat tagaggtcac gtgagtgttt tgcgacattt tgcgacacca tgtggtcacg    60
ctgggtattt aagcccgagt gagcacgcag ggtctccatt ttgaagcggg aggtttgaac   120
gcgcagccgc c                                                        131
```

<210> SEQ ID NO 11
<211> LENGTH: 131
<212> TYPE: DNA
<213> ORGANISM: adeno-associated virus 3
<220> FEATURE:
<221> NAME/KEY: 'misc_feature
<222> LOCATION: (1)..(131)
<223> OTHER INFORMATION: P5 Promoter of AAV3

<400> SEQUENCE: 11

```
ccagctgcgt cagcagtcag gtgacccttt tgcgacagtt tgcgacacca cgtggccgct    60
gagggtatat attctcgagt gagcgaacca ggagctccat tttgaccgcg aaatttgaac   120
gagcagcagc c                                                        131
```

<210> SEQ ID NO 12
<211> LENGTH: 192
<212> TYPE: DNA
<213> ORGANISM: adeno-associated virus 4
<220> FEATURE:
<221> NAME/KEY: misc_feature
<222> LOCATION: (1)..(192)
<223> OTHER INFORMATION: P5 Promoter of AAV4

<400> SEQUENCE: 12

```
ggtccctgta ttagcagtca cgtgagtgtc gtatttcgcg gagcgtagcg gagcgcatac    60
caagctgcca cgtcacagcc acgtggtccg tttgcgacag tttgcgacac catgtggtca   120
ggagggtata taaccgcgag tgagccagcg aggagctcca ttttgcccgc gaattttgaa   180
cgagcagcag cc                                                       192
```

<210> SEQ ID NO 13
<211> LENGTH: 131
<212> TYPE: DNA
<213> ORGANISM: adeno-associated virus 5
<220> FEATURE:
<221> NAME/KEY: misc_feature
<222> LOCATION: (1)..(131)
<223> OTHER INFORMATION: P5 Promoter of AAV5

<400> SEQUENCE: 13

```
atgtgatgtg ttttatccaa taggaagaaa gcgcgcgtat gagttctcgc gagacttccg    60
gggtataaaa gaccgagtga acgagcccgc cgccattctt tgctctggac tgctagagga   120
ccctcgctgc c                                                        131
```

<210> SEQ ID NO 14
<211> LENGTH: 130
<212> TYPE: DNA
<213> ORGANISM: adeno-associated virus 6
<220> FEATURE:
<221> NAME/KEY: misc_feature
<222> LOCATION: (1)..(130)
<223> OTHER INFORMATION: P5 Promoter of AAV6

<400> SEQUENCE: 14

```
ggtcctgtat tagaggtcac gtgagtgttt tgcgacattt tgcgacacca tgtggtcacg    60
ctgggtattt aagcccgagt gagcacgcag ggtctccatt ttgaagcggg aggttttgaac  120 gcgcagcgcc                                                         130
```

<210> SEQ ID NO 15
<211> LENGTH: 131
<212> TYPE: DNA
<213> ORGANISM: adeno-associated virus 7
<220> FEATURE:
<221> NAME/KEY: misc_feature
<222> LOCATION: (1)..(131)
<223> OTHER INFORMATION: P5 Promoter of AAV7

<400> SEQUENCE: 15

```
ggtcctgtat tagctgtcac gtgagtgctt ttgcgacatt ttgcgacacc acgtggccat    60
ttgaggtata tatggccgag tgagcgagca ggatctccat tttgaccgcg aaatttgaac   120
gagcagcagc c                                                        131
```

<210> SEQ ID NO 16
<211> LENGTH: 131
<212> TYPE: DNA

```
<213> ORGANISM: adeno-associated virus 8
<220> FEATURE:
<221> NAME/KEY: misc_feature
<222> LOCATION: (1)..(131)
<223> OTHER INFORMATION: P5 Promoter of AAV8

<400> SEQUENCE: 16
ggtcctgtat tagctgtcac gtgagtgctt ttgcggcatt ttgcgacacc acgtggccat      60
ttgaggtata tatggccgag tgagcgagca ggatctccat tttgaccgcg aaatttgaac     120
gagcagcagc c                                                          131

<210> SEQ ID NO 17
<211> LENGTH: 180
<212> TYPE: DNA
<213> ORGANISM: adeno-associated virus 1
<220> FEATURE:
<221> NAME/KEY: misc_feature
<222> LOCATION: (1)..(180)
<223> OTHER INFORMATION: P40 Promoter of AAV1

<400> SEQUENCE: 17
ggtgacaaag caggaagtca aagagttctt ccgctgggcg caggatcacg tgaccgaggt      60
ggcgcatgag ttctacgtca gaaagggtgg agccaacaaa agacccgccc ccgatgacgc     120
ggataaaagc gagcccaagc gggcctgccc ctcagtcgcg gatccatcga cgtcagacgc     180

<210> SEQ ID NO 18
<211> LENGTH: 180
<212> TYPE: DNA
<213> ORGANISM: adeno-associated virus 2
<220> FEATURE:
<221> NAME/KEY: misc_feature
<222> LOCATION: (1)..(180)
<223> OTHER INFORMATION: P40 Promoter of AAV2

<400> SEQUENCE: 18
ggtcaccaag caggaagtca aagacttttt ccggtgggca aaggatcacg tggttgaggt      60
ggagcatgaa ttctacgtca aaagggtgg agccaagaaa agacccgccc ccagtgacgc     120
agatataagt gagcccaaac gggtgcgcga gtcagttgcg cagccatcga cgtcagacgc     180

<210> SEQ ID NO 19
<211> LENGTH: 180
<212> TYPE: DNA
<213> ORGANISM: adeno-associated virus 3
<220> FEATURE:
<221> NAME/KEY: misc_feature
<222> LOCATION: (1)..(180)
<223> OTHER INFORMATION: P40 Promoter of AAV3

<400> SEQUENCE: 19
ggtcaccaaa caggaagtaa aggacttttt ccggtgggct tccgatcacg tgactgacgt      60
ggctcatgag ttctacgtca gaaagggtgg agctaagaaa cgccccgcct ccaatgacgc     120
ggatgtaagc gagccaaaac gggagtgcac gtcacttgcg cagccgacaa cgtcagacgc     180

<210> SEQ ID NO 20
<211> LENGTH: 180
<212> TYPE: DNA
<213> ORGANISM: adeno-associated virus 4
<220> FEATURE:
<221> NAME/KEY: misc_feature
<222> LOCATION: (1)..(180)
<223> OTHER INFORMATION: P40 Promoter of AAV4

<400> SEQUENCE: 20
```

```
ggtcaccaag caggaagtca aagactttt ccggtgggcg tcagatcacg tgaccgaggt    60
gactcacgag ttttacgtca gaaagggtgg agctagaaag aggcccgccc ccaatgacgc   120
agatataagt gagcccaagc gggcctgtcc gtcagttgcg cagccatcga cgtcagacgc   180
```

<210> SEQ ID NO 21
<211> LENGTH: 227
<212> TYPE: DNA
<213> ORGANISM: adeno-associated virus 5
<220> FEATURE:
<221> NAME/KEY: misc_feature
<222> LOCATION: (1)..(227)
<223> OTHER INFORMATION: P40 Promoter of AAV5

<400> SEQUENCE: 21

```
gattactaag caggaagtca aggactttt tgcttgggca aaggtcaatc aggtgccggt    60
gactcacgag tttaaagttc ccagggaatt ggcgggaact aaaggggcgg agaaatctct   120
aaaacgccca ctgggtgacg tcaccaatac tagctataaa agtctggaga gcgggcctg   180 gagcatgagg ctctcatttg ttcccgagac gcctcgcagt tcagacg                227
```

<210> SEQ ID NO 22
<211> LENGTH: 180
<212> TYPE: DNA
<213> ORGANISM: adeno-associated virus 6
<220> FEATURE:
<221> NAME/KEY: misc_feature
<222> LOCATION: (1)..(180)
<223> OTHER INFORMATION: P40 Promoter of AAV6

<400> SEQUENCE: 22

```
ggtgacaaag caggaagtca aagagttctt ccgctgggcg caggatcacg tgaccgaggt    60
ggcgcatgag ttctacgtca gaaagggtgg agccaacaag agacccgccc ccgatgacgc   120
ggataaaagc gagcccaagc gggcctgccc ctcagtcgcg gatccatcga cgtcagacgc   180
```

<210> SEQ ID NO 23
<211> LENGTH: 180
<212> TYPE: DNA
<213> ORGANISM: adeno-associated virus 7
<220> FEATURE:
<221> NAME/KEY: misc_feature
<222> LOCATION: (1)..(180)
<223> OTHER INFORMATION: P40 Promoter of AAV7

<400> SEQUENCE: 23

```
ggtgacgaag caggaagtca aagagttctt ccgctgggcc agtgatcacg tgaccgaggt    60
ggcgcatgag ttctacgtca gaaagggcgg agccagcaaa agacccgccc ccgatgacgc   120
ggatataagc gagcccaagc gggcctgccc ctcagtcgcg gatccatcga cgtcagacgc   180
```

<210> SEQ ID NO 24
<211> LENGTH: 180
<212> TYPE: DNA
<213> ORGANISM: adeno-associated virus 8
<220> FEATURE:
<221> NAME/KEY: misc_feature
<222> LOCATION: (1)..(180)
<223> OTHER INFORMATION: P40 Promoter of AAV8

```
<400> SEQUENCE: 24
ggtgacaaag caggaagtca aagagttctt ccgctgggcc agtgatcacg tgaccgaggt      60
ggcgcatgag ttttacgtca gaaagggcgg agccagcaaa agacccgccc ccgatgacgc     120
ggataaaagc gagcccaagc gggcctgccc ctcagtcgcg gatccatcga cgtcagacgc     180
```